(12) United States Patent
Kikuchi et al.

(10) Patent No.: US 7,972,829 B2
(45) Date of Patent: Jul. 5, 2011

(54) PROCESS FOR PRODUCING TRANSGLUTAMINASE

(75) Inventors: Yoshimi Kikuchi, Kawasaki (JP); Masayo Date, Kawasaki (JP); Yukiko Umezawa, Kawasaki (JP); Keiichi Yokoyama, Kawasaki (JP); Hiroshi Matsui, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/714,151

(22) Filed: Feb. 26, 2010

(65) Prior Publication Data

US 2010/0297729 A1 Nov. 25, 2010

Related U.S. Application Data

(60) Division of application No. 10/112,488, filed on Apr. 1, 2002, now Pat. No. 7,723,067, which is a continuation of application No. PCT/JP00/06780, filed on Sep. 29, 2000.

(30) Foreign Application Priority Data

Sep. 30, 1999 (JP) .................................... 11-280098
Jun. 28, 2000 (JP) ................................. 2000-194043

(51) Int. Cl.
   C12N 9/10 (2006.01)
   C12N 1/20 (2006.01)
   C12N 15/00 (2006.01)
   C12P 21/04 (2006.01)
   A61K 38/00 (2006.01)
   C07H 21/04 (2006.01)
   C07H 21/02 (2006.01)
   C07K 1/00 (2006.01)
   C12Q 1/68 (2006.01)
   C12Q 1/00 (2006.01)

(52) U.S. Cl. ............... 435/193; 435/4; 435/6; 435/71.1; 435/69.1; 435/252.3; 435/320.1; 435/440; 536/23.2; 536/23.4; 430/350; 430/300

(58) Field of Classification Search .................. None
See application file for complete search history.

(56) References Cited

FOREIGN PATENT DOCUMENTS

| | | |
|---|---|---|
| EP | 0 198 645 | 10/1986 |
| JP | 06-253838 | 9/1994 |
| JP | 09-316095 | 12/1997 |
| JP | 10-108675 | 4/1998 |
| JP | 05-244947 | 9/1998 |
| JP | 05-244974 | 9/1998 |
| RU | 2091490 | 9/1997 |
| WO | WO 88/09821 | 12/1988 |

OTHER PUBLICATIONS

D. Baker, et al., "The role of pro regions in protein folding", Current Opinion in Cell Biology, 1993, vol. 5, No. 6, pp. 966-970.
J. Eder, et al., "Pro-sequence-assisted protein folding", Molecular Microbiology, 1995, vol. 16, No. 4, pp. 609-614.
K. Washizu, et al., "Molecular cloning of the gene for microbial transglutaminase from Streptoverticillium and its expression in Streptomyces lividans", Bios. Biotech. Biochem., 1994, vol. 58, No. 1, pp. 82-87.
I. Kim, et al., "The deduced sequence of the novel protransglutaminase E (TGase3) of human and mouse", The Journal of Biological Chemistry, Jun. 15, 1993, vol. 268, No. 17, pp. 12682-12690.
R. Duran, et al., Purification, characterization, and gene cloning of transglutaminase from Streptoverticillium cinnamoneum CBS 683.68, Biochimie, Apr. 4, 1998, vol. 80, No. 4, pp. 313-319.
K. Salim, et al., "Heterologous expression of the Mycobacterium tuberculosis gene encoding antigen 85a in Corynebacterium glutamicum", Applied and Environmental Microbiology, Nov. 1997, vol. 63, No. 11, pp. 4392-4400.
H. Billman-Jacobe, et al., "Expression and secretion of heterologous proteases by cornebacterium glutamicum", Applied and Environmental Microbiology, Apr. 1995, vol. 61, No. 4, pp. 1610-1613.
G. Joliff, et al., "Cloning and nucleotide sequence of the csp1 gene encoding PS1, one of the two major secreted proteins of Corynebacterium glutamicum: the deduced N-terminal region of PS1 is similar to the Mycobacterium antigen 85 complex", Molecular Microbiology, 1992, vol. 6, No. 16, pp. 2349-2362, XP-00981993.
Y. Kikuchi, et al., "Secretio of active-form Streptoverticillium mobaraense transglutaminase by Corynebacterium glutamicum: Processing of the pro-transglutaminase by a cosecreted subtilisin-like protease from Streptomyces albogiseolus", Applied and Environmental Microbiology, Jan. 2003, vol. 69, No. 1, pp. 358-366.

*Primary Examiner* — Yong D Pak
(74) *Attorney, Agent, or Firm* — Oblon, Spivak, McClelland, Maier & Neustadt, L.L.P.

(57) ABSTRACT

The present invention relates to a process for secretory production of a foreign protein, in particular, transglutaminase by a coryneform bacterium.
According to the present invention, a process is provided for the secretory production of a foreign protein, in particular, transglutaminase, by making a coryneform bacterium to produce an industrially useful foreign protein, in particular, transglutaminase and efficiently release the product extracellularly (i.e., secretory production).
An intended foreign protein, in particular, transglutaminase, is produced by using an expression construct wherein the gene sequence of the intended foreign protein containing the pro-structure part, in particular, pro-transglutaminase gene sequence, is ligated to the downstream of a sequence encoding the signal peptide region from a coryneform bacterium, introducing this expressional genetic construct into a coryneform bacterium, culturing the thus transformed coryneform bacterium, and treating the extracellularly released protein with a protease, etc. to cleave and eliminate the pro-part.

4 Claims, No Drawings

SEQUENCE LISTING

```
<160> NUMBER OF SEQ ID NOS: 70

<210> SEQ ID NO 1
<211> LENGTH: 30
<212> TYPE: PRT
<213> ORGANISM: Corynebacterium glutamicum

<400> SEQUENCE: 1

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala
            20                  25                  30

<210> SEQ ID NO 2
<211> LENGTH: 25
<212> TYPE: PRT
<213> ORGANISM: Corynebacterium ammoniagenes

<400> SEQUENCE: 2

Met Lys Arg Met Lys Ser Leu Ala Ala Ala Leu Thr Val Ala Gly Ala
1               5                   10                  15

Met Leu Ala Ala Pro Val Ala Thr Ala
            20                  25

<210> SEQ ID NO 3
<211> LENGTH: 45
<212> TYPE: PRT
<213> ORGANISM: Streptoverticillium mobaraense

<400> SEQUENCE: 3

Asp Asn Gly Ala Gly Glu Glu Thr Lys Ser Tyr Ala Glu Thr Tyr Arg
1               5                   10                  15

Leu Thr Ala Asp Asp Val Ala Asn Ile Asn Ala Leu Asn Glu Ser Ala
            20                  25                  30

Pro Ala Ala Ser Ser Ala Gly Pro Ser Phe Arg Ala Pro
        35                  40                  45

<210> SEQ ID NO 4
<211> LENGTH: 54
<212> TYPE: PRT
<213> ORGANISM: Streptoverticillium cinnamoneum

<400> SEQUENCE: 4

Gly Asp Gly Glu Glu Lys Gly Ser Tyr Ala Glu Thr His Gly Leu Thr
1               5                   10                  15

Ala Asp Asp Val Glu Ser Ile Asn Ala Leu Asn Glu Arg Ala Leu Thr
            20                  25                  30

Leu Gly Gln Pro Gly Lys Pro Pro Lys Glu Leu Pro Pro Ser Ala Ser
        35                  40                  45
```

Ala Pro Ser Arg Ala Pro
            50

<210> SEQ ID NO 5
<211> LENGTH: 331
<212> TYPE: PRT
<213> ORGANISM: Streptoverticillium mobaraense

<400> SEQUENCE: 5

Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Lys Gly Phe Gln Arg Ala Arg Glu
            115                 120                 125

Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330

<210> SEQ ID NO 6
<211> LENGTH: 782
<212> TYPE: DNA
<213> ORGANISM: Corynebacterium glutamicum
<220> FEATURE:

<221> NAME/KEY: CDS
<222> LOCATION: (579)..(782)
<223> OTHER INFORMATION:

<400> SEQUENCE: 6

```
aaattcctgt gaattagctg atttagtact tttcggaggt gtctattctt accaaatcgt      60
caagttgtgg gtagagtcac ctgaatatta attgcaccgc acgggtgata tatgcttatt     120
tgctcaagta gttcgaggtt aagtgtattt taggtgaaca aatttcagct tcgggtagaa     180
gactttcgat gcgcttcaga gcttctattg ggaaatctga caccacttga ttaaatagcc     240 taccccgaa ttgggggatt ggtcattttt tgctgtgaag gtagttttga tgcatatgac      300
ctgcgtttat aaagaaatgt aaacgtgatc agatcgatat aaaagaaaca gtttgtactc     360
aggtttgaag cattttctcc gattcgcctg gcaaaaatct caattgtcgc ttacagtttt     420
tctcaacgac aggctgctaa gctgctagtt cggtggccta gtgagtggcg tttacttgga     480
taaaagtaat cccatgtcgt gatcagccat tttgggttgt ttccatagca atccaaaggt     540
ttcgtctttc gatacctatt caaggagcct tcgcctct atg ttt aac aac cgt atc     596
                                         Met Phe Asn Asn Arg Ile
                                         1               5 cgc act gca gct ctc gct ggt gca atc gca atc tcc acc gca gct tcc       644
Arg Thr Ala Ala Leu Ala Gly Ala Ile Ala Ile Ser Thr Ala Ala Ser
            10                  15                  20 ggc gta gct atc cca gca ttc gct cag gag acc aac cca acc ttc aac       692
Gly Val Ala Ile Pro Ala Phe Ala Gln Glu Thr Asn Pro Thr Phe Asn
        25                  30                  35 atc aac aac ggc ttc aac gat gct gat gga tcc acc atc cag cca gtt       740
Ile Asn Asn Gly Phe Asn Asp Ala Asp Gly Ser Thr Ile Gln Pro Val
    40                  45                  50 gag cca gtt aac cac acc gag gaa acc ctc cgc gac ctg act             782
Glu Pro Val Asn His Thr Glu Glu Thr Leu Arg Asp Leu Thr
55                  60                  65
```

<210> SEQ ID NO 7
<211> LENGTH: 68
<212> TYPE: PRT
<213> ORGANISM: Corynebacterium glutamicum

<400> SEQUENCE: 7

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Asn Pro Thr Phe Asn Ile Asn Asn Gly Phe Asn Asp Ala Asp Gly
        35                  40                  45

Ser Thr Ile Gln Pro Val Glu Pro Val Asn His Thr Glu Glu Thr Leu
    50                  55                  60

Arg Asp Leu Thr
65
```

<210> SEQ ID NO 8
<211> LENGTH: 30
<212> TYPE: DNA
<213> ORGANISM: Artificial Sequence
<220> FEATURE:
<223> OTHER INFORMATION: synthetic DNA

<400> SEQUENCE: 8

```
gactccgacg acagggtcac ccctcccgcc                                       30
```

```
<210> SEQ ID NO 9
<211> LENGTH: 30
<212> TYPE: DNA
<213> ORGANISM: Artificial Sequence
<220> FEATURE:
<223> OTHER INFORMATION: synthetic DNA

<400> SEQUENCE: 9
cgctcacatc acggccagcc ctgctttacc                              30

<210> SEQ ID NO 10
<211> LENGTH: 20
<212> TYPE: DNA
<213> ORGANISM: Artificial Sequence
<220> FEATURE:
<223> OTHER INFORMATION: synthetic DNA

<400> SEQUENCE: 10
gtgaccctgt cgtcggagtc                                         20

<210> SEQ ID NO 11
<211> LENGTH: 20
<212> TYPE: DNA
<213> ORGANISM: Artificial Sequence
<220> FEATURE:
<223> OTHER INFORMATION: synthetic DNA

<400> SEQUENCE: 11
ggcatcctgt cgagcggctc                                         20

<210> SEQ ID NO 12
<211> LENGTH: 1809
<212> TYPE: DNA
<213> ORGANISM: Stretoverticullium mobaraense
<220> FEATURE:
<221> NAME/KEY: CDS
<222> LOCATION: (578)..(1798)
<223> OTHER INFORMATION:

<400> SEQUENCE: 12
gtcgacgcgg gccgggaggg ggtgcggcgg cgcccttcgg ctgtgtggac gaagcgtcgg    60
gtcggagggg cggccggata tcgtccttgg ggcggggtgg ccggaattgc cgccatggtg   120
ttgccgggga atcgacccga agacatgatc acttctcgta tccacccgat cacgtatccg   180
ggagtcgaga agtgttacgc cgtgcccctg tccgcgtcct caccccctgtc gccgtgacag   240 cgacccgcgt tcttccactc gcacggacgg ccccacagga cctttcggcc cgggctcgcc   300
ccgccgcctc ggtgacggcc tccgaataac gcggccgccg gggcctcggc cggttgaccg   360
atccgggtca cgcgcccgcc cgggcgggcg gccacgtccg gtctcgcccc gcccgacatc   420
ggctgcgact gccttcgctc gcacttcttc ccgcctcccg gccgcgtttt tccgccgccg   480
aaggtgcggc gacgcgtacc gaatccccct tcatcgcgac gtgcttccgc acggccgcgt   540
tcaacgatgt tccacgacaa aggagttgca ggtttcc atg cgc ata cgc cgg aga    595
                                         Met Arg Ile Arg Arg Arg
                                         1               5 gct ctc gtc ttc gcc act atg agt gcg gtg tta tgc acc gcc gga ttc    643
Ala Leu Val Phe Ala Thr Met Ser Ala Val Leu Cys Thr Ala Gly Phe
            10                  15                  20 atg ccg tcg gcc ggc gag gcc gcc gcc gac aat ggc gcg ggg gaa gag    691
Met Pro Ser Ala Gly Glu Ala Ala Ala Asp Asn Gly Ala Gly Glu Glu
        25                  30                  35 acg aag tcc tac gcc gaa acc tac cgc ctc acg gcg gat gac gtc gcg    739
Thr Lys Ser Tyr Ala Glu Thr Tyr Arg Leu Thr Ala Asp Asp Val Ala
    40                  45                  50
```

-continued

| | |
|---|---|
| aac atc aac gcg ctc aac gaa agc gct ccg gcc gct tcg agc gcc ggc<br>Asn Ile Asn Ala Leu Asn Glu Ser Ala Pro Ala Ala Ser Ser Ala Gly<br>55                   60                   65                   70 | 787 |
| ccg tcg ttc cgg gcc ccc gac tcc gac gac agg gtc acc cct ccc gcc<br>Pro Ser Phe Arg Ala Pro Asp Ser Asp Asp Arg Val Thr Pro Pro Ala<br>                  75                   80                   85 | 835 |
| gag ccg ctc gac agg atg ccc gac ccg tac cgt ccc tcg tac ggc agg<br>Glu Pro Leu Asp Arg Met Pro Asp Pro Tyr Arg Pro Ser Tyr Gly Arg<br>          90                   95                  100 | 883 |
| gcc gag acg gtc gtc aac aac tac ata cgc aag tgg cag cag gtc tac<br>Ala Glu Thr Val Val Asn Asn Tyr Ile Arg Lys Trp Gln Gln Val Tyr<br>105                  110                  115 | 931 |
| agc cac cgc gac ggc agg aag cag cag atg acc gag gag cag cgg gag<br>Ser His Arg Asp Gly Arg Lys Gln Gln Met Thr Glu Glu Gln Arg Glu<br>120                  125                  130 | 979 |
| tgg ctg tcc tac ggc tgc gtc ggt gtc acc tgg gtc aat tcg ggt cag<br>Trp Leu Ser Tyr Gly Cys Val Gly Val Thr Trp Val Asn Ser Gly Gln<br>135                  140                  145                  150 | 1027 |
| tac ccg acg aac aga ctg gcc ttc gcg tcc ttc gac gag gac agg ttc<br>Tyr Pro Thr Asn Arg Leu Ala Phe Ala Ser Phe Asp Glu Asp Arg Phe<br>                  155                  160                  165 | 1075 |
| aag aac gag ctg aag aac ggc agg ccc cgg tcc ggc gag acg cgg gcg<br>Lys Asn Glu Leu Lys Asn Gly Arg Pro Arg Ser Gly Glu Thr Arg Ala<br>          170                  175                  180 | 1123 |
| gag ttc gag ggc cgc gtc gcg aag gag agc ttc gac gag gag aag ggc<br>Glu Phe Glu Gly Arg Val Ala Lys Glu Ser Phe Asp Glu Glu Lys Gly<br>185                  190                  195 | 1171 |
| ttc cag cgg gcg cgt gag gtg gcg tcc gtc atg aac agg gcc ctg gag<br>Phe Gln Arg Ala Arg Glu Val Ala Ser Val Met Asn Arg Ala Leu Glu<br>200                  205                  210 | 1219 |
| aac gcc cac gac gag agc gct tac ctc gac aac ctc aag aag gaa ctg<br>Asn Ala His Asp Glu Ser Ala Tyr Leu Asp Asn Leu Lys Lys Glu Leu<br>215                  220                  225                  230 | 1267 |
| gcg aac ggc aac gac gcc ctg cgc aac gag gac gcc cgt tcc ccg ttc<br>Ala Asn Gly Asn Asp Ala Leu Arg Asn Glu Asp Ala Arg Ser Pro Phe<br>                  235                  240                  245 | 1315 |
| tac tcg gcg ctg cgg aac acg ccg tcc ttc aag gag cgg aac gga ggc<br>Tyr Ser Ala Leu Arg Asn Thr Pro Ser Phe Lys Glu Arg Asn Gly Gly<br>          250                  255                  260 | 1363 |
| aat cac gac ccg tcc agg atg aag gcc gtc atc tac tcg aag cac ttc<br>Asn His Asp Pro Ser Arg Met Lys Ala Val Ile Tyr Ser Lys His Phe<br>265                  270                  275 | 1411 |
| tgg agc ggc cag gac cgg tcg agt tcg gcc gac aag agg aag tac ggc<br>Trp Ser Gly Gln Asp Arg Ser Ser Ser Ala Asp Lys Arg Lys Tyr Gly<br>280                  285                  290 | 1459 |
| gac ccg gac gcc ttc cgc ccc gcc ccg ggc acc ggc ctg gtc gac atg<br>Asp Pro Asp Ala Phe Arg Pro Ala Pro Gly Thr Gly Leu Val Asp Met<br>295                  300                  305                  310 | 1507 |
| tcg agg gac agg aac att ccg cgc agc ccc acc agc ccc ggt gag gga<br>Ser Arg Asp Arg Asn Ile Pro Arg Ser Pro Thr Ser Pro Gly Glu Gly<br>                  315                  320                  325 | 1555 |
| ttc gtc aat ttc gac tac ggc tgg ttc ggc gcc cag acg gaa gcg gac<br>Phe Val Asn Phe Asp Tyr Gly Trp Phe Gly Ala Gln Thr Glu Ala Asp<br>          330                  335                  340 | 1603 |
| gcc gac aag acc gtc tgg acc cac gga aat cac tat cac gcg ccc aat<br>Ala Asp Lys Thr Val Trp Thr His Gly Asn His Tyr His Ala Pro Asn<br>345                  350                  355 | 1651 |
| ggc agc ctg ggt gcc atg cat gtc tac gag agc aag ttc cgc aac tgg<br>Gly Ser Leu Gly Ala Met His Val Tyr Glu Ser Lys Phe Arg Asn Trp<br>360                  365                  370 | 1699 |

```
tcc gag ggt tac tcg gac ttc gac cgc gga gcc tat gtg atc acc ttc    1747
Ser Glu Gly Tyr Ser Asp Phe Asp Arg Gly Ala Tyr Val Ile Thr Phe
375                 380                 385                 390 atc ccc aag agc tgg aac acc gcc ccc gac aag gta aag cag ggc tgg    1795
Ile Pro Lys Ser Trp Asn Thr Ala Pro Asp Lys Val Lys Gln Gly Trp
            395                 400                 405 ccg tgatgtgagc g                                                    1809
Pro
```

<210> SEQ ID NO 13
<211> LENGTH: 407
<212> TYPE: PRT
<213> ORGANISM: Stretoverticullium mobaraense

<400> SEQUENCE: 13

```
Met Arg Ile Arg Arg Ala Leu Val Phe Ala Thr Met Ser Ala Val
1               5                   10                  15

Leu Cys Thr Ala Gly Phe Met Pro Ser Ala Gly Glu Ala Ala Asp
                20                  25                  30

Asn Gly Ala Gly Glu Glu Thr Lys Ser Tyr Ala Glu Thr Tyr Arg Leu
            35                  40                  45

Thr Ala Asp Asp Val Ala Asn Ile Asn Ala Leu Asn Glu Ser Ala Pro
50                  55                  60

Ala Ala Ser Ser Ala Gly Pro Ser Phe Arg Ala Pro Asp Ser Asp Asp
65                  70                  75                  80

Arg Val Thr Pro Pro Ala Glu Pro Leu Asp Arg Met Pro Asp Pro Tyr
                85                  90                  95

Arg Pro Ser Tyr Gly Arg Ala Glu Thr Val Val Asn Asn Tyr Ile Arg
            100                 105                 110

Lys Trp Gln Gln Val Tyr Ser His Arg Asp Gly Arg Lys Gln Gln Met
        115                 120                 125

Thr Glu Glu Gln Arg Glu Trp Leu Ser Tyr Gly Cys Val Gly Val Thr
    130                 135                 140

Trp Val Asn Ser Gly Gln Tyr Pro Thr Asn Arg Leu Ala Phe Ala Ser
145                 150                 155                 160

Phe Asp Glu Asp Arg Phe Lys Asn Glu Leu Lys Asn Gly Arg Pro Arg
                165                 170                 175

Ser Gly Glu Thr Arg Ala Glu Phe Glu Gly Arg Val Ala Lys Glu Ser
            180                 185                 190

Phe Asp Glu Glu Lys Gly Phe Gln Arg Ala Arg Glu Val Ala Ser Val
        195                 200                 205

Met Asn Arg Ala Leu Glu Asn Ala His Asp Glu Ser Ala Tyr Leu Asp
    210                 215                 220

Asn Leu Lys Lys Glu Leu Ala Asn Gly Asn Asp Ala Leu Arg Asn Glu
225                 230                 235                 240

Asp Ala Arg Ser Pro Phe Tyr Ser Ala Leu Arg Asn Thr Pro Ser Phe
                245                 250                 255

Lys Glu Arg Asn Gly Gly Asn His Asp Pro Ser Arg Met Lys Ala Val
            260                 265                 270

Ile Tyr Ser Lys His Phe Trp Ser Gly Gln Asp Arg Ser Ser Ser Ala
        275                 280                 285

Asp Lys Arg Lys Tyr Gly Asp Pro Asp Ala Phe Arg Pro Ala Pro Gly
    290                 295                 300

Thr Gly Leu Val Asp Met Ser Arg Asp Arg Asn Ile Pro Arg Ser Pro
305                 310                 315                 320
```

-continued

```
Thr Ser Pro Gly Glu Gly Phe Val Asn Phe Asp Tyr Gly Trp Phe Gly
            325                 330                 335

Ala Gln Thr Glu Ala Asp Ala Asp Lys Thr Val Trp Thr His Gly Asn
            340                 345                 350

His Tyr His Ala Pro Asn Gly Ser Leu Gly Ala Met His Val Tyr Glu
        355                 360                 365

Ser Lys Phe Arg Asn Trp Ser Glu Gly Tyr Ser Asp Phe Asp Arg Gly
    370                 375                 380

Ala Tyr Val Ile Thr Phe Ile Pro Lys Ser Trp Asn Thr Ala Pro Asp
385                 390                 395                 400

Lys Val Lys Gln Gly Trp Pro
                405

<210> SEQ ID NO 14
<211> LENGTH: 26
<212> TYPE: DNA
<213> ORGANISM: Artificial Sequence
<220> FEATURE:
<223> OTHER INFORMATION: synthetic DNA

<400> SEQUENCE: 14
aaattcctgt gaattagctg atttag                                    26

<210> SEQ ID NO 15
<211> LENGTH: 44
<212> TYPE: DNA
<213> ORGANISM: Artificial Sequence
<220> FEATURE:
<223> OTHER INFORMATION: synthetic DNA

<400> SEQUENCE: 15
gagctctccg gcgtatgcgc atagaggcga aggctccttg aata                44

<210> SEQ ID NO 16
<211> LENGTH: 30
<212> TYPE: DNA
<213> ORGANISM: Artificial Sequence
<220> FEATURE:
<223> OTHER INFORMATION: synthetic DNA

<400> SEQUENCE: 16
atgcgcatac gccggagagc tctcgtcttc                                30

<210> SEQ ID NO 17
<211> LENGTH: 47
<212> TYPE: DNA
<213> ORGANISM: Artificial Sequence
<220> FEATURE:
<223> OTHER INFORMATION: synthetic DNA

<400> SEQUENCE: 17
ggggtgaccc tgtcgtcgga gtcgttgaag ccgttgttga tgttgaa             47

<210> SEQ ID NO 18
<211> LENGTH: 51
<212> TYPE: DNA
<213> ORGANISM: Artificial Sequence
<220> FEATURE:
<223> OTHER INFORMATION: synthetic DNA

<400> SEQUENCE: 18
cttcgtctct tccccgcgc cattgtcagc gaatgctggg atagcaacgc c          51

<210> SEQ ID NO 19
```

-continued

<210> SEQ ID NO 19
<211> LENGTH: 51
<212> TYPE: DNA
<213> ORGANISM: Artificial Sequence
<220> FEATURE:
<223> OTHER INFORMATION: synthetic DNA

<400> SEQUENCE: 19
cttcgtctct tccccgcgc cattgtcctg agcgaatgct gggatagcta c        51

<210> SEQ ID NO 20
<211> LENGTH: 51
<212> TYPE: DNA
<213> ORGANISM: Artificial Sequence
<220> FEATURE:
<223> OTHER INFORMATION: synthetic DNA

<400> SEQUENCE: 20
cttcgtctct tccccgcgc cattgtcgtt gaagccgttg ttgatgttga a        51

<210> SEQ ID NO 21
<211> LENGTH: 51
<212> TYPE: DNA
<213> ORGANISM: Artificial Sequence
<220> FEATURE:
<223> OTHER INFORMATION: synthetic DNA

<400> SEQUENCE: 21
cttcgtctct tccccgcgc cattgtcagt caggtcgcgg agggtttcct c        51

<210> SEQ ID NO 22
<211> LENGTH: 30
<212> TYPE: DNA
<213> ORGANISM: Artificial Sequence
<220> FEATURE:
<223> OTHER INFORMATION: synthetic DNA

<400> SEQUENCE: 22
gacaatggcg cggggaaga gacgaagtcc                                 30

<210> SEQ ID NO 23
<211> LENGTH: 25
<212> TYPE: DNA
<213> ORGANISM: Artificial Sequence
<220> FEATURE:
<223> OTHER INFORMATION: synthetic DNA

<400> SEQUENCE: 23
gcccagaagc ccaaaattga gattt                                     25

<210> SEQ ID NO 24
<211> LENGTH: 52
<212> TYPE: DNA
<213> ORGANISM: Artificial Sequence
<220> FEATURE:
<223> OTHER INFORMATION: synthetic DNA

<400> SEQUENCE: 24
cttcgtctct tccccgcgc cattgtctgc cgttgccaca ggtgcggcca gc        52

<210> SEQ ID NO 25
<211> LENGTH: 52
<212> TYPE: DNA
<213> ORGANISM: Artificial Sequence
<220> FEATURE:
<223> OTHER INFORMATION: synthetic DNA

<400> SEQUENCE: 25

```
cgcagccagc gatttcatgc gtttcataga ggcgaaggct ccttgaatag gt    52
```

<210> SEQ ID NO 26
<211> LENGTH: 30
<212> TYPE: DNA
<213> ORGANISM: Artificial Sequence
<220> FEATURE:
<223> OTHER INFORMATION: synthetic DNA

<400> SEQUENCE: 26

```
atgaaacgca tgaaatcgct ggctgcggcg                              30
```

<210> SEQ ID NO 27
<211> LENGTH: 25
<212> TYPE: DNA
<213> ORGANISM: Artificial Sequence
<220> FEATURE:
<223> OTHER INFORMATION: synthetic DNA

<400> SEQUENCE: 27

```
ggatccggag cttatcgact gcacg                                   25
```

<210> SEQ ID NO 28
<211> LENGTH: 52
<212> TYPE: DNA
<213> ORGANISM: Artificial Sequence
<220> FEATURE:
<223> OTHER INFORMATION: synthetic DNA

<400> SEQUENCE: 28

```
cgcagccagc gatttcatgc gtttcataat tctgtttcct gtgtgaaatt gt    52
```

<210> SEQ ID NO 29
<211> LENGTH: 43
<212> TYPE: PRT
<213> ORGANISM: Corynebacterium glutamicum

<400> SEQUENCE: 29

```
Met Arg Asp Thr Ala Phe Arg Ser Ile Lys Ala Lys Ala Gln Ala Lys
1               5                   10                  15
Arg Arg Ser Leu Trp Ile Ala Ala Gly Ala Val Pro Thr Ala Ile Ala
            20                  25                  30
Leu Thr Met Ser Leu Ala Pro Met Ala Ser Ala
        35                  40
```

<210> SEQ ID NO 30
<211> LENGTH: 43
<212> TYPE: PRT
<213> ORGANISM: Streptoverticillium mobaraense

<400> SEQUENCE: 30

```
Asp Asn Gly Ala Gly Glu Glu Thr Lys Ser Tyr Ala Glu Thr Tyr Arg
1               5                   10                  15
Leu Thr Ala Asp Asp Val Ala Asn Ile Asn Ala Leu Asn Glu Ser Ala
            20                  25                  30
Pro Ala Ala Ser Ser Ala Gly Pro Ser Phe Arg
        35                  40
```

<210> SEQ ID NO 31
<211> LENGTH: 41
<212> TYPE: PRT
<213> ORGANISM: Streptoverticillium mobaraense

<400> SEQUENCE: 31

```
Asp Asn Gly Ala Gly Glu Glu Thr Lys Ser Tyr Ala Glu Thr Tyr Arg
1               5                   10                  15

Leu Thr Ala Asp Asp Val Ala Asn Ile Asn Ala Leu Asn Glu Ser Ala
            20                  25                  30

Pro Ala Ala Ser Ser Ala Gly Pro Ser
        35                  40
```

<210> SEQ ID NO 32
<211> LENGTH: 44
<212> TYPE: PRT
<213> ORGANISM: Streptoverticillium mobaraense

<400> SEQUENCE: 32

```
Asn Gly Ala Gly Glu Glu Thr Lys Ser Tyr Ala Glu Thr Tyr Arg Leu
1               5                   10                  15

Thr Ala Asp Asp Val Ala Asn Ile Asn Ala Leu Asn Glu Ser Ala Pro
            20                  25                  30

Ala Ala Ser Ser Ala Gly Pro Ser Phe Arg Ala Pro
        35                  40
```

<210> SEQ ID NO 33
<211> LENGTH: 39
<212> TYPE: PRT
<213> ORGANISM: Streptoverticillium mobaraense

<400> SEQUENCE: 33

```
Glu Thr Lys Ser Tyr Ala Glu Thr Tyr Arg Leu Thr Ala Asp Asp Val
1               5                   10                  15

Ala Asn Ile Asn Ala Leu Asn Glu Ser Ala Pro Ala Ala Ser Ser Ala
            20                  25                  30

Gly Pro Ser Phe Arg Ala Pro
        35
```

<210> SEQ ID NO 34
<211> LENGTH: 45
<212> TYPE: PRT
<213> ORGANISM: Artificial Sequence
<220> FEATURE:
<223> OTHER INFORMATION: synthetic peptide: modified pro-region of
      Streptverticullium mobaraense transglutaminase pro-region

<400> SEQUENCE: 34

```
Asp Asn Gly Ala Gly Glu Glu Thr Lys Ser Tyr Ala Glu Thr Tyr Arg
1               5                   10                  15

Leu Thr Ala Asp Asp Val Ala Asn Ile Asn Ala Leu Asn Glu Ser Ala
            20                  25                  30

Pro Ala Ala Ser Ser Ala Gly Pro Ser Phe Gly Pro Lys
        35                  40                  45
```

<210> SEQ ID NO 35
<211> LENGTH: 45
<212> TYPE: PRT
<213> ORGANISM: Artificial Sequence
<220> FEATURE:
<223> OTHER INFORMATION: synthetic peptide-modified Streptoverticillium
      mobaraense transglutaminase pro-region

<400> SEQUENCE: 35

```
Asp Asn Gly Ala Gly Glu Glu Thr Lys Ser Tyr Ala Glu Thr Tyr Arg
1               5                   10                  15

Leu Thr Ala Asp Asp Val Ala Asn Ile Asn Ala Leu Asn Glu Ser Ala
            20                  25                  30
```

```
Pro Ala Ala Ser Ser Ala Gly Pro Ser Phe Gly Pro Arg
            35                  40                  45

<210> SEQ ID NO 36
<211> LENGTH: 41
<212> TYPE: PRT
<213> ORGANISM: Artificial Sequence
<220> FEATURE:
<223> OTHER INFORMATION: synthetic peptide-modified Streptoverticillium
      mobaraense transglutaminase pro-region

<400> SEQUENCE: 36

Asp Asn Gly Ala Gly Glu Glu Thr Lys Ser Tyr Ala Glu Thr Tyr Arg
1               5                   10                  15

Leu Thr Ala Asp Asp Val Ala Asn Ile Asn Ala Leu Asn Glu Ser Ala
            20                  25                  30

Pro Ala Ala Ser Ser Ala Gly Pro Lys
            35                  40

<210> SEQ ID NO 37
<211> LENGTH: 41
<212> TYPE: PRT
<213> ORGANISM: Artificial Sequence
<220> FEATURE:
<223> OTHER INFORMATION: synthetic peptide-modified Streptoverticillium
      mobaraense transglutaminase pro-region

<400> SEQUENCE: 37

Asp Asn Gly Ala Gly Glu Glu Thr Lys Ser Tyr Ala Glu Thr Tyr Arg
1               5                   10                  15

Leu Thr Ala Asp Asp Val Ala Asn Ile Asn Ala Leu Asn Glu Ser Ala
            20                  25                  30

Pro Ala Ala Ser Ser Ala Gly Pro Arg
            35                  40

<210> SEQ ID NO 38
<211> LENGTH: 56
<212> TYPE: PRT
<213> ORGANISM: Artificial Sequence
<220> FEATURE:
<223> OTHER INFORMATION: synthetic peptide-chimera of
      Streptoverticillium mobaraenseand Streptoverticillium cinnamoneum
      transglutaminase pro-regions

<400> SEQUENCE: 38

Asp Asn Gly Ala Gly Glu Glu Thr Lys Ser Tyr Ala Glu Thr Tyr Arg
1               5                   10                  15

Leu Thr Ala Asp Asp Val Glu Ser Ile Asn Ala Leu Asn Glu Arg Ala
            20                  25                  30

Leu Thr Leu Gly Gln Pro Gly Lys Pro Pro Lys Glu Leu Pro Pro Ser
            35                  40                  45

Ala Ser Ala Pro Ser Arg Ala Pro
    50                  55

<210> SEQ ID NO 39
<211> LENGTH: 1079
<212> TYPE: PRT
<213> ORGANISM: Streptomyces albogriseolus

<400> SEQUENCE: 39

Asn Gly Glu Asn Ser Thr Ala Ala Gly Ser Ser Ala Ser Ala Thr Ala
1               5                   10                  15

Leu Lys Gly Lys His Arg Val Thr Leu Ile Thr Gly Asp Arg Val Ala
            20                  25                  30
```

```
Leu Asp Ala Lys Gly Arg Val Gly Leu Glu Pro Ala Glu Gly Arg
         35                  40                  45
Glu His Ile Pro Val Gln Ile Arg Arg Ser Asp Gly His Thr Leu Val
 50                  55                  60
Val Pro Ala Asp Ala Ala Arg Leu Val Ala Ser Gly Lys Leu Asp Gln
 65                  70                  75                  80
Arg Leu Phe Asp Val Thr Glu Leu Asn Lys Ala Ala Thr Arg Thr Ala
                 85                  90                  95
His Arg Gly Gly Leu Lys Val Ile Val Gly Tyr Arg Gly Ala Ala Lys
            100                 105                 110
Ala Ala Lys Ala Asp Val Arg Asp Ala Gly Thr Val Arg Arg Thr Leu
            115                 120                 125
Thr Ser Leu Asn Ala Asp Ala Val Gln Thr Pro Gln Glu Ala Gly Ala
        130                 135                 140
Glu Leu Trp Glu Ala Val Thr Asp Gly Asp Arg Thr Ala Ser Gly Val
145                 150                 155                 160
Ala Arg Val Trp Leu Asp Gly Val Arg Lys Ala Ser Leu Asp Thr Ser
                165                 170                 175
Val Gly Gln Ile Gly Thr Pro Lys Ala Trp Glu Ala Gly Tyr Asp Gly
            180                 185                 190
Lys Gly Val Lys Ile Ala Val Leu Asp Thr Gly Val Asp Ala Thr His
            195                 200                 205
Pro Asp Leu Lys Gly Gln Val Thr Ala Ser Lys Asn Phe Thr Ser Ala
        210                 215                 220
Pro Thr Thr Gly Asp Val Val Gly His Gly Thr His Val Ala Ser Ile
225                 230                 235                 240
Ala Ala Gly Thr Gly Ala Gln Ser Lys Gly Thr Tyr Lys Gly Val Ala
                245                 250                 255
Pro Gly Ala Lys Ile Leu Asn Gly Lys Val Leu Asp Asp Ala Gly Phe
            260                 265                 270
Gly Asp Asp Ser Gly Ile Leu Ala Gly Met Glu Trp Ala Ala Ala Gln
        275                 280                 285
Gly Ala Asp Ile Val Asn Met Ser Leu Gly Gly Met Asp Thr Pro Glu
        290                 295                 300
Thr Asp Pro Leu Glu Ala Ala Val Asp Lys Leu Ser Ala Glu Lys Gly
305                 310                 315                 320
Ile Leu Phe Ala Ile Ala Ala Gly Asn Glu Gly Pro Gln Ser Ile Gly
                325                 330                 335
Ser Pro Gly Ser Ala Asp Ser Ala Leu Thr Val Gly Ala Val Asp Asp
            340                 345                 350
Lys Asp Lys Leu Ala Asp Phe Ser Ser Thr Gly Pro Arg Leu Gly Asp
        355                 360                 365
Gly Ala Val Lys Pro Asp Leu Thr Ala Pro Gly Val Asp Ile Thr Ala
        370                 375                 380
Ala Ser Ala Lys Gly Asn Asp Ile Ala Lys Glu Val Gly Glu Lys Pro
385                 390                 395                 400
Ala Gly Tyr Met Thr Ile Ser Gly Thr Ser Met Ala Thr Pro His Val
                405                 410                 415
Ala Gly Ala Ala Ala Leu Leu Lys Gln Gln His Pro Glu Trp Lys Tyr
            420                 425                 430
Ala Glu Leu Lys Gly Ala Leu Thr Ala Ser Thr Lys Asp Gly Lys Tyr
        435                 440                 445
Thr Pro Phe Glu Gln Gly Ser Gly Arg Val Gln Val Asp Lys Ala Ile
```

-continued

```
            450                 455                 460
Thr Gln Thr Val Ile Ala Glu Pro Val Ser Leu Ser Phe Gly Val Gln
465                 470                 475                 480

Gln Trp Pro His Ala Asp Asp Lys Pro Val Thr Lys Lys Leu Thr Tyr
                485                 490                 495

Arg Asn Leu Gly Thr Glu Asp Val Thr Leu Lys Leu Thr Ser Thr Ala
                500                 505                 510

Thr Gly Pro Lys Gly Lys Ala Pro Ala Gly Phe Phe Thr Leu Gly
                515                 520                 525

Ala Ser Thr Leu Thr Val Pro Ala Asn Gly Thr Ala Ser Val Asp Val
530                 535                 540

Thr Ala Asp Thr Arg Leu Gly Ala Val Asp Gly Thr Tyr Ser Ala
545                 550                 555                 560

Tyr Val Ala Thr Gly Ala Gly Gln Ser Val Arg Thr Ala Ala Ala
                565                 570                 575

Val Glu Arg Glu Val Glu Ser Tyr Asn Val Thr Leu Lys Val Leu Asp
                580                 585                 590

Arg Ser Gly Lys Ala Thr Ala Asn Tyr Met Ala Tyr Leu Ser Gly Leu
                595                 600                 605

Thr Gly Leu Gly Lys Asp Arg Ser Tyr Ala Pro Tyr Glu Ala Asp Gly
                610                 615                 620

Ala Val Ser Val Arg Val Pro Lys Gly Gly Tyr Val Leu Asp Ala Ser
625                 630                 635                 640

Val Leu Val Gly Ala Asp Pro Glu Thr Trp Arg Gly Ala Asp Trp Leu
                645                 650                 655

Ala Gln Pro Lys Leu Asp Val Thr Arg Asn Thr Thr Val Thr Val Asp
                660                 665                 670

Ala Arg Lys Ala Lys Pro Val Lys Val Thr Pro Gly Lys Ala Ala
                675                 680                 685

Lys Ala Gln Phe Ala Ser Ala Asp Tyr Thr Ile Glu Thr Asn Asp Ser
                690                 695                 700

Ala Val Ser Tyr Gly Trp Trp Leu Glu Asn Tyr Ser Gly Phe Arg Ser
705                 710                 715                 720

Ala His Leu Gly Pro Gln Ile Thr Asn Gly Thr Leu Ser Gln Gln Trp
                725                 730                 735

Asn Thr His Phe Ser Asn Gly Ala Lys Ala Gln Tyr Thr Ala Ile Ser
                740                 745                 750

Gly Gly Lys Val Lys Lys Leu Ala Thr Gly Tyr Thr Arg Ala Phe Lys
                755                 760                 765

Ala Lys Glu Phe Ala Thr Val Gln Val Gly Met Gly Ala Ala Ala Ser
770                 775                 780

Gly Lys Lys Gly Ala Val Thr Ala Phe Gly Trp Leu Pro Gly Ser Ser
785                 790                 795                 800

Gly Ala Ser Gly Phe Ser Gln Glu Gln Lys Leu Pro Ser Thr Arg Thr
                805                 810                 815

Leu Tyr Leu Ser Thr Val Asn Gly Val Thr Trp Asp Leu Asp Phe Glu
                820                 825                 830

Gln Leu Gly Gly Val Asp Asn Glu Gly Trp Pro Ile Tyr Asp Ala Val
                835                 840                 845

Tyr Thr Ile Gly Val Gly Lys Thr Lys Gly Gly Lys Thr Tyr Lys
                850                 855                 860

Glu Thr Val Asn Thr Ala Val Phe Gly Pro Arg Leu Thr Ser Ser Tyr
865                 870                 875                 880
```

-continued

Gly Val Phe Arg Asp Gly Asn Ser Ile Tyr Gly Val Ile Pro Leu Phe
            885                 890                 895

Ala Asp Gly Lys Gly His Ala Gly Ser Ser Glu Phe Ser Ser Ala Val
            900                 905                 910

Thr Thr Leu Tyr Arg Asn Gly Lys Lys Val Gly Ser Asn Asn Asp Pro
            915                 920                 925

Leu Phe Gly Glu Glu Gly Phe Thr Val Pro Ser Gly Asp Ala Ala Tyr
            930                 935                 940

Arg Leu Thr Thr Ser Val Lys Arg Ser Ala Lys Val Ala Ala Ala Ser
945                 950                 955                 960

Thr Arg Ile Asp Ala Ser Trp Thr Phe Arg Ser Lys Lys Thr Ser Gly
            965                 970                 975

Glu Lys Gln Leu Pro Val Ser Ser Ala Arg Phe Ala Val Thr Gly
            980                 985                 990

Leu Asp Ser Lys Val Ala Ala Gly Lys Lys Ala Thr Phe Pro Val Val
            995                 1000                1005

Val Glu Gly Ala Ala Gln Gly Lys Asn Leu Lys Ser Leu Ala Val
            1010                1015                1020

Tyr Val Ser Tyr Asn Gly Gly Lys Thr Trp Lys Lys Thr Thr Val
            1025                1030                1035

Thr Lys Gly Lys Ile Thr Val Lys Asn Pro Ala Lys Gly Lys Ala
            1040                1045                1050

Ile Ser Phe Arg Ala Lys Ile Thr Asp Lys Lys Gly Asn Ala Ser
            1055                1060                1065

Leu Ile Thr Ile His Asn Ala Tyr Tyr Gly Lys
            1070                1075

<210> SEQ ID NO 40
<211> LENGTH: 444
<212> TYPE: PRT
<213> ORGANISM: Streptoverticillium mobaraense

<400> SEQUENCE: 40

Gln Ala Asp Ile Lys Asp Arg Ile Leu Lys Ile Pro Gly Met Lys Phe
1               5                   10                  15

Val Glu Glu Lys Pro Tyr Gln Gly Tyr Arg Tyr Leu Val Met Thr Tyr
                20                  25                  30

Arg Gln Pro Val Asp His Arg Asn Pro Gly Lys Gly Thr Phe Glu Gln
            35                  40                  45

Arg Phe Thr Leu Leu His Lys Asp Thr Asp Arg Pro Thr Val Phe Phe
        50                  55                  60

Thr Ser Gly Tyr Asn Val Ser Thr Asn Pro Ser Arg Ser Glu Pro Thr
65                  70                  75                  80

Arg Ile Val Asp Gly Asn Gln Val Ser Met Glu Tyr Arg Phe Phe Thr
                85                  90                  95

Pro Ser Arg Pro Gln Pro Ala Asp Trp Ser Lys Leu Asp Ile Trp Gln
            100                 105                 110

Ala Ala Ser Asp Gln His Arg Leu Tyr Gln Ala Leu Lys Pro Val Tyr
        115                 120                 125

Gly Lys Asn Trp Leu Ala Thr Gly Gly Ser Lys Gly Gly Met Thr Ala
    130                 135                 140

Thr Tyr Phe Arg Arg Phe Tyr Pro Asn Asp Met Asn Gly Thr Val Ala
145                 150                 155                 160

Tyr Val Ala Pro Asn Asp Val Asn Asp Lys Glu Asp Ser Ala Tyr Asp
                165                 170                 175

-continued

```
Lys Phe Phe Gln Asn Val Gly Asp Lys Ala Cys Arg Thr Gln Leu Asn
            180                 185                 190

Ser Val Gln Arg Glu Ala Leu Val Arg Arg Asp Glu Ile Val Ala Arg
        195                 200                 205

Tyr Glu Lys Trp Ala Lys Glu Asn Gly Lys Thr Phe Lys Val Val Gly
    210                 215                 220

Ser Ala Asp Lys Ala Tyr Glu Asn Val Val Leu Asp Leu Val Trp Ser
225                 230                 235                 240

Phe Trp Gln Tyr His Leu Gln Ser Asp Cys Ala Ser Val Pro Ala Thr
                245                 250                 255

Lys Ala Ser Thr Asp Glu Leu Tyr Lys Phe Ile Asp Asp Ile Ser Gly
            260                 265                 270

Phe Asp Gly Tyr Thr Asp Gln Gly Leu Glu Arg Phe Thr Pro Tyr Tyr
        275                 280                 285

Tyr Gln Ala Gly Thr Gln Leu Gly Ala Pro Thr Val Lys Asn Pro His
    290                 295                 300

Leu Lys Gly Val Leu Arg Tyr Pro Gly Ile Asn Gln Pro Arg Ser Tyr
305                 310                 315                 320

Val Pro Arg Asp Ile Pro Met Thr Phe Arg Pro Gly Ala Met Ala Asp
                325                 330                 335

Val Asp Arg Trp Val Arg Glu Asp Ser Arg Asn Met Leu Phe Val Tyr
            340                 345                 350

Gly Gln Asn Asp Pro Trp Ser Gly Glu Pro Phe Arg Leu Gly Lys Gly
        355                 360                 365

Ala Ala Ala Arg His Asp Tyr Arg Phe Tyr Ala Pro Gly Gly Asn His
    370                 375                 380

Gly Ser Asn Ile Ala Gln Leu Val Ala Asp Glu Arg Ala Lys Ala Thr
385                 390                 395                 400

Ala Glu Val Leu Lys Trp Ala Gly Val Ala Pro Gln Ala Val Gln Lys
                405                 410                 415

Asp Glu Lys Ala Ala Lys Pro Leu Ala Pro Phe Asp Ala Lys Leu Asp
            420                 425                 430

Arg Val Lys Asn Asp Lys Gln Ser Ala Leu Arg Pro
        435                 440
```

<210> SEQ ID NO 41
<211> LENGTH: 1739
<212> TYPE: DNA
<213> ORGANISM: Streptoverticillium mobaraense
<220> FEATURE:
<221> NAME/KEY: CDS
<222> LOCATION: (229)..(1659)
<223> OTHER INFORMATION:

<400> SEQUENCE: 41

```
gctcctatga gcatcgacgc cgccagcagc gatcggttcg gtctgaccgt cgacgccgac      60
ggcgagcgcg tgtggctgga cgagcccggt cggcccgtgc cgctcgtgcg gccgtgaaag     120
gcccgaaaag agcccaagcc gtgtgaactg cgaggacaaa gggtctggcg caacgcatgt     180
cacccccgat aagttcgccg cgacctttgc gaacccaggg gagggcgc atg cgc aag      237
                                                    Met Arg Lys
                                                      1 gct ctc aga tcg ctg ctg gcg gcg tcg atg ctc ata gga gcg atc ggc      285
Ala Leu Arg Ser Leu Leu Ala Ala Ser Met Leu Ile Gly Ala Ile Gly
    5                  10                  15 gcc ggc agc gcc acg gcg gag gcg gcg tcg atc acc gcc ccg cag gcc      333
Ala Gly Ser Ala Thr Ala Glu Ala Ala Ser Ile Thr Ala Pro Gln Ala
20                  25                  30                  35
```

```
gac atc aag gac cgc atc ctg aag att ccc ggg atg aag ttc gtc gag    381
Asp Ile Lys Asp Arg Ile Leu Lys Ile Pro Gly Met Lys Phe Val Glu
            40                  45                  50 gag aag ccc tac cag ggc tac cgc tac ctc gtg atg acg tac cgg cag    429
Glu Lys Pro Tyr Gln Gly Tyr Arg Tyr Leu Val Met Thr Tyr Arg Gln
        55                  60                  65 ccg gtg gac cac cgc aat ccc ggc aag ggg acc ttc gag cag cgc ttc    477
Pro Val Asp His Arg Asn Pro Gly Lys Gly Thr Phe Glu Gln Arg Phe
    70                  75                  80 acc ctg ctc cac aag gac acc gac cgg ccg acc gtg ttc ttc acg tcc    525
Thr Leu Leu His Lys Asp Thr Asp Arg Pro Thr Val Phe Phe Thr Ser
85                  90                  95 ggc tac aac gtc tcc acc aac ccc agc cgc agc gag ccc acg cgc atc    573
Gly Tyr Asn Val Ser Thr Asn Pro Ser Arg Ser Glu Pro Thr Arg Ile
100                 105                 110                 115 gtg gac ggc aac cag gtg tcg atg gag tac cgg ttc ttc acg ccg tcc    621
Val Asp Gly Asn Gln Val Ser Met Glu Tyr Arg Phe Phe Thr Pro Ser
        120                 125                 130 cgg ccg cag ccc gcc gac tgg tcc aag ctg gac atc tgg cag gcg gcg    669
Arg Pro Gln Pro Ala Asp Trp Ser Lys Leu Asp Ile Trp Gln Ala Ala
            135                 140                 145 agt gac cag cac cgc ctg tac cag gcg ctg aag ccg gtc tac ggg aag    717
Ser Asp Gln His Arg Leu Tyr Gln Ala Leu Lys Pro Val Tyr Gly Lys
                150                 155                 160 aac tgg ctg gcc acg ggc ggc agc aag ggc ggc atg acg gcc acc tac    765
Asn Trp Leu Ala Thr Gly Gly Ser Lys Gly Gly Met Thr Ala Thr Tyr
        165                 170                 175 ttc cgc cgc ttc tac ccg aac gac atg aac ggc acg gtc gcc tac gtc    813
Phe Arg Arg Phe Tyr Pro Asn Asp Met Asn Gly Thr Val Ala Tyr Val
180                 185                 190                 195 gcg ccc aac gac gtg aac gac aag gaa gac tcg gcg tac gac aag ttc    861
Ala Pro Asn Asp Val Asn Asp Lys Glu Asp Ser Ala Tyr Asp Lys Phe
            200                 205                 210 ttc cag aac gtc ggc gac aag gcg tgc cgc acg cag ctc aac tcg gtg    909
Phe Gln Asn Val Gly Asp Lys Ala Cys Arg Thr Gln Leu Asn Ser Val
                215                 220                 225 cag cgc gag gcg ctc gtc cgc cgc gac gag atc gtc gcc cgc tac gag    957
Gln Arg Glu Ala Leu Val Arg Arg Asp Glu Ile Val Ala Arg Tyr Glu
        230                 235                 240 aag tgg gct aag gag aac ggc aag acg ttc aag gtc gtc ggc agc gcc    1005
Lys Trp Ala Lys Glu Asn Gly Lys Thr Phe Lys Val Val Gly Ser Ala
    245                 250                 255 gac aag gcg tac gag aac gtc gtc ctc gac ctg gtc tgg tcc ttc tgg    1053
Asp Lys Ala Tyr Glu Asn Val Val Leu Asp Leu Val Trp Ser Phe Trp
260                 265                 270                 275 cag tac cac ctg cag agc gac tgc gcc tcc gtc ccc gcc acc aag gcg    1101
Gln Tyr His Leu Gln Ser Asp Cys Ala Ser Val Pro Ala Thr Lys Ala
            280                 285                 290 tcc acc gac gag ctg tac aag ttc atc gac gac atc tcg ggc ttc gac    1149
Ser Thr Asp Glu Leu Tyr Lys Phe Ile Asp Asp Ile Ser Gly Phe Asp
                295                 300                 305 ggc tac acc gac cag ggc ctg gag cgc ttc acc ccg tac tac tac cag    1197
Gly Tyr Thr Asp Gln Gly Leu Glu Arg Phe Thr Pro Tyr Tyr Tyr Gln
        310                 315                 320 gcg ggc acc cag ctc ggc gcc cct acg gtg aag aac ccg cac ctc aag    1245
Ala Gly Thr Gln Leu Gly Ala Pro Thr Val Lys Asn Pro His Leu Lys
    325                 330                 335 ggc gtg ctg cgg tac ccc ggc atc aac cag ccg cgc tcg tac gtc ccc    1293
Gly Val Leu Arg Tyr Pro Gly Ile Asn Gln Pro Arg Ser Tyr Val Pro
340                 345                 350                 355
```

```
cgc gac atc ccg atg acc ttc cgc ccc ggc gcg atg gcg gac gtc gac    1341
Arg Asp Ile Pro Met Thr Phe Arg Pro Gly Ala Met Ala Asp Val Asp
            360                 365                 370 cgc tgg gtg cgc gag gac agc cgg aac atg ctc ttc gtg tac ggg cag    1389
Arg Trp Val Arg Glu Asp Ser Arg Asn Met Leu Phe Val Tyr Gly Gln
        375                 380                 385 aac gac ccg tgg agc ggt gaa ccg ttc cgc ctg ggc aag ggc gcc gcc    1437
Asn Asp Pro Trp Ser Gly Glu Pro Phe Arg Leu Gly Lys Gly Ala Ala
    390                 395                 400 gcc cgg cac gac tac cgc ttc tac gcc ccg ggc ggc aac cac ggt tcc    1485
Ala Arg His Asp Tyr Arg Phe Tyr Ala Pro Gly Gly Asn His Gly Ser
405                 410                 415 aac atc gcc cag ttg gtg gcc gac gag cgg gcc aag gcc acg gcc gag    1533
Asn Ile Ala Gln Leu Val Ala Asp Glu Arg Ala Lys Ala Thr Ala Glu
420                 425                 430                 435 gtc ctg aag tgg gcc ggt gtg gcg ccg cag gcc gtc cag aag gac gag    1581
Val Leu Lys Trp Ala Gly Val Ala Pro Gln Ala Val Gln Lys Asp Glu
            440                 445                 450 aag gcc gcc aag ccg ctc gcg ccg ttc gac gcc aag ctc gac cgc gtg    1629
Lys Ala Ala Lys Pro Leu Ala Pro Phe Asp Ala Lys Leu Asp Arg Val
        455                 460                 465 aag aac gac aag cag agc gcg ctg cgt ccg tagggaccca gtgcgtaagg    1679
Lys Asn Asp Lys Gln Ser Ala Leu Arg Pro
    470                 475 cggcgggcgc tcccggcgag gggcgcccgc cgtcgcgttc cggaaggccc cgggtgccgc    1739

<210> SEQ ID NO 42
<211> LENGTH: 477
<212> TYPE: PRT
<213> ORGANISM: Streptoverticillium mobaraense

<400> SEQUENCE: 42

Met Arg Lys Ala Leu Arg Ser Leu Leu Ala Ala Ser Met Leu Ile Gly
1               5                   10                  15

Ala Ile Gly Ala Gly Ser Ala Thr Ala Glu Ala Ala Ser Ile Thr Ala
            20                  25                  30

Pro Gln Ala Asp Ile Lys Asp Arg Ile Leu Lys Ile Pro Gly Met Lys
        35                  40                  45

Phe Val Glu Glu Lys Pro Tyr Gln Gly Tyr Arg Tyr Leu Val Met Thr
    50                  55                  60

Tyr Arg Gln Pro Val Asp His Arg Asn Pro Gly Lys Gly Thr Phe Glu
65                  70                  75                  80

Gln Arg Phe Thr Leu Leu His Lys Asp Thr Asp Arg Pro Thr Val Phe
                85                  90                  95

Phe Thr Ser Gly Tyr Asn Val Ser Thr Asn Pro Ser Arg Ser Glu Pro
            100                 105                 110

Thr Arg Ile Val Asp Gly Asn Gln Val Ser Met Glu Tyr Arg Phe Phe
        115                 120                 125

Thr Pro Ser Arg Pro Gln Pro Ala Asp Trp Ser Lys Leu Asp Ile Trp
    130                 135                 140

Gln Ala Ala Ser Asp Gln His Arg Leu Tyr Gln Ala Leu Lys Pro Val
145                 150                 155                 160

Tyr Gly Lys Asn Trp Leu Ala Thr Gly Gly Ser Lys Gly Gly Met Thr
                165                 170                 175

Ala Thr Tyr Phe Arg Arg Phe Tyr Pro Asn Asp Met Asn Gly Thr Val
            180                 185                 190

Ala Tyr Val Ala Pro Asn Asp Val Asn Asp Lys Glu Asp Ser Ala Tyr
```

```
            195                 200                 205
Asp Lys Phe Phe Gln Asn Val Gly Asp Lys Ala Cys Arg Thr Gln Leu
    210                 215                 220

Asn Ser Val Gln Arg Glu Ala Leu Val Arg Arg Asp Glu Ile Val Ala
225                 230                 235                 240

Arg Tyr Glu Lys Trp Ala Lys Glu Asn Gly Lys Thr Phe Lys Val Val
            245                 250                 255

Gly Ser Ala Asp Lys Ala Tyr Glu Asn Val Val Leu Asp Leu Val Trp
        260                 265                 270

Ser Phe Trp Gln Tyr His Leu Gln Ser Asp Cys Ala Ser Val Pro Ala
    275                 280                 285

Thr Lys Ala Ser Thr Asp Glu Leu Tyr Lys Phe Ile Asp Asp Ile Ser
290                 295                 300

Gly Phe Asp Gly Tyr Thr Asp Gln Gly Leu Glu Arg Phe Thr Pro Tyr
305                 310                 315                 320

Tyr Tyr Gln Ala Gly Thr Gln Leu Gly Ala Pro Thr Val Lys Asn Pro
            325                 330                 335

His Leu Lys Gly Val Leu Arg Tyr Pro Gly Ile Asn Gln Pro Arg Ser
        340                 345                 350

Tyr Val Pro Arg Asp Ile Pro Met Thr Phe Arg Pro Gly Ala Met Ala
    355                 360                 365

Asp Val Asp Arg Trp Val Arg Glu Asp Ser Arg Asn Met Leu Phe Val
370                 375                 380

Tyr Gly Gln Asn Asp Pro Trp Ser Gly Glu Pro Phe Arg Leu Gly Lys
385                 390                 395                 400

Gly Ala Ala Ala Arg His Asp Tyr Arg Phe Tyr Ala Pro Gly Gly Asn
            405                 410                 415

His Gly Ser Asn Ile Ala Gln Leu Val Ala Asp Glu Arg Ala Lys Ala
        420                 425                 430

Thr Ala Glu Val Leu Lys Trp Ala Gly Val Ala Pro Gln Ala Val Gln
    435                 440                 445

Lys Asp Glu Lys Ala Ala Lys Pro Leu Ala Pro Phe Asp Ala Lys Leu
450                 455                 460

Asp Arg Val Lys Asn Asp Lys Gln Ser Ala Leu Arg Pro
465                 470                 475

<210> SEQ ID NO 43
<211> LENGTH: 330
<212> TYPE: PRT
<213> ORGANISM: Streptoverticillium cinnamoneum

<400> SEQUENCE: 43

Ser Asp Asp Arg Glu Thr Pro Pro Ala Glu Pro Leu Asp Arg Met Pro
1               5                   10                  15

Glu Ala Tyr Arg Ala Tyr Gly Gly Arg Ala Thr Thr Val Val Asn Asn
            20                  25                  30

Tyr Ile Arg Lys Trp Gln Gln Val Tyr Ser His Arg Asp Gly Lys Lys
        35                  40                  45

Gln Gln Met Thr Glu Glu Gln Arg Glu Lys Leu Ser Tyr Gly Cys Val
    50                  55                  60

Gly Val Thr Trp Val Asn Ser Gly Pro Tyr Pro Thr Asn Arg Leu Ala
65                  70                  75                  80

Phe Ala Ser Phe Asp Glu Asn Lys Tyr Lys Asn Asp Leu Lys Asn Thr
                85                  90                  95

Ser Pro Arg Pro Asp Glu Thr Arg Ala Glu Phe Glu Gly Arg Ile Ala
```

```
            100                 105                 110
Lys Gly Ser Phe Asp Glu Gly Lys Gly Phe Lys Arg Ala Arg Asp Val
            115                 120                 125

Ala Ser Val Met Asn Lys Ala Leu Glu Asn Ala His Asp Glu Gly Thr
        130                 135                 140

Tyr Ile Asn Asn Leu Lys Thr Glu Leu Thr Asn Asn Asp Ala Leu
145                 150                 155                 160

Leu Arg Glu Asp Ser Arg Ser Asn Phe Tyr Ser Ala Leu Arg Asn Thr
                165                 170                 175

Pro Ser Phe Lys Glu Arg Asp Gly Gly Asn Tyr Asp Pro Ser Lys Met
            180                 185                 190

Lys Ala Val Ile Tyr Ser Lys His Phe Trp Ser Gly Gln Asp Gln Arg
        195                 200                 205

Gly Ser Ser Asp Lys Arg Lys Tyr Gly Asp Pro Glu Ala Phe Arg Pro
    210                 215                 220

Asp Gln Gly Thr Gly Leu Val Asp Met Ser Lys Asp Arg Ser Ile Pro
225                 230                 235                 240

Arg Ser Pro Ala Lys Pro Gly Glu Gly Trp Val Asn Phe Asp Tyr Gly
                245                 250                 255

Trp Phe Gly Ala Gln Thr Glu Ala Asp Ala Asp Lys Thr Thr Trp Thr
            260                 265                 270

His Gly Asp His Tyr His Ala Pro Asn Ser Asp Leu Gly Pro Met His
        275                 280                 285

Val His Glu Ser Lys Phe Arg Lys Trp Ser Ala Gly Tyr Ala Asp Phe
    290                 295                 300

Asp Arg Gly Ala Tyr Val Ile Thr Phe Ile Pro Lys Ser Trp Asn Thr
305                 310                 315                 320

Ala Pro Ala Lys Val Glu Gln Gly Trp Pro
                325                 330

<210> SEQ ID NO 44
<211> LENGTH: 21
<212> TYPE: DNA
<213> ORGANISM: Artificial Sequence
<220> FEATURE:
<223> OTHER INFORMATION: synthetic DNA

<400> SEQUENCE: 44
ggcgatgggg aagagaaggg g                                         21

<210> SEQ ID NO 45
<211> LENGTH: 32
<212> TYPE: DNA
<213> ORGANISM: Artificial Sequence
<220> FEATURE:
<223> OTHER INFORMATION: synthetic DNA

<400> SEQUENCE: 45
ggcggatcct cgcgtcgaga ggcgtggact ga                             32

<210> SEQ ID NO 46
<211> LENGTH: 21
<212> TYPE: DNA
<213> ORGANISM: Artificial Sequence
<220> FEATURE:
<223> OTHER INFORMATION: synthetic DNA

<400> SEQUENCE: 46
tacgaattcg agctcggtac c                                         21
```

```
<210> SEQ ID NO 47
<211> LENGTH: 43
<212> TYPE: DNA
<213> ORGANISM: Artificial Sequence
<220> FEATURE:
<223> OTHER INFORMATION: synthetic DNA

<400> SEQUENCE: 47
ccccttctct tccccatcgc ctgccgttgc cacaggtgcg gcc            43

<210> SEQ ID NO 48
<211> LENGTH: 46
<212> TYPE: DNA
<213> ORGANISM: Artificial Sequence
<220> FEATURE:
<223> OTHER INFORMATION: synthetic DNA

<400> SEQUENCE: 48
ggggtgaccc tgtcgtcgga gtcgggggcc cgggagggcg cgctgg         46

<210> SEQ ID NO 49
<211> LENGTH: 26
<212> TYPE: DNA
<213> ORGANISM: Artificial Sequence
<220> FEATURE:
<223> OTHER INFORMATION: synthetic DNA

<400> SEQUENCE: 49
aacggggaga acagcacggc cgccgg                               26

<210> SEQ ID NO 50
<211> LENGTH: 29
<212> TYPE: DNA
<213> ORGANISM: Artificial Sequence
<220> FEATURE:
<223> OTHER INFORMATION: synthetic DNA

<400> SEQUENCE: 50
ggcgaattct ccggcgggcc gtcaccggt                            29

<210> SEQ ID NO 51
<211> LENGTH: 30
<212> TYPE: DNA
<213> ORGANISM: Artificial Sequence
<220> FEATURE:
<223> OTHER INFORMATION: synthetic DNA

<400> SEQUENCE: 51
ggcaagctta aattcctgtg aattagctga                           30

<210> SEQ ID NO 52
<211> LENGTH: 44
<212> TYPE: DNA
<213> ORGANISM: Artificial Sequence
<220> FEATURE:
<223> OTHER INFORMATION: synthetic DNA

<400> SEQUENCE: 52
cggccgtgct gttctccccg tttgccgttg ccacaggtgc ggcc           44

<210> SEQ ID NO 53
<211> LENGTH: 20
<212> TYPE: PRT
<213> ORGANISM: Streptoverticillium mobaraense

<400> SEQUENCE: 53
```

```
Gln Ala Asp Ile Lys Asp Arg Ile Leu Lys Ile Pro Gly Met Lys Phe
1               5                   10                  15
Val Glu Glu Lys
            20
```

<210> SEQ ID NO 54
<211> LENGTH: 33
<212> TYPE: DNA
<213> ORGANISM: Artificial Sequence
<220> FEATURE:
<223> OTHER INFORMATION: synthetic DNA

<400> SEQUENCE: 54
aagatccccg ggatgaagtt cgtcgaggag aag                        33

<210> SEQ ID NO 55
<211> LENGTH: 23
<212> TYPE: DNA
<213> ORGANISM: Artificial Sequence
<220> FEATURE:
<223> OTHER INFORMATION: synthetic DNA

<400> SEQUENCE: 55
gaggcggcgt cgatcaccgc ccc                                   23

<210> SEQ ID NO 56
<211> LENGTH: 32
<212> TYPE: DNA
<213> ORGANISM: Artificial Sequence
<220> FEATURE:
<223> OTHER INFORMATION: synthetic DNA

<400> SEQUENCE: 56
gccaagcttg aagcaccggc ggcggcaccc gg                         32

<210> SEQ ID NO 57
<211> LENGTH: 46
<212> TYPE: DNA
<213> ORGANISM: Artificial Sequence
<220> FEATURE:
<223> OTHER INFORMATION: synthetic DNA

<400> SEQUENCE: 57
ggggcggtga tcgacgccgc ctctgccgtt gccacaggtg cggcca          46

<210> SEQ ID NO 58
<211> LENGTH: 40
<212> TYPE: DNA
<213> ORGANISM: Artificial Sequence
<220> FEATURE:
<223> OTHER INFORMATION: synthetic DNA

<400> SEQUENCE: 58
gtgaccctgt cgtcggagtc ccggaacgac gggccggcgc                 40

<210> SEQ ID NO 59
<211> LENGTH: 40
<212> TYPE: DNA
<213> ORGANISM: Artificial Sequence
<220> FEATURE:
<223> OTHER INFORMATION: synthetic DNA

<400> SEQUENCE: 59
gtgaccctgt cgtcggagtc cgacgggccg gcgctcgaag                 40

<210> SEQ ID NO 60

```
<211> LENGTH: 40
<212> TYPE: DNA
<213> ORGANISM: Artificial Sequence
<220> FEATURE:
<223> OTHER INFORMATION: synthetic DNA

<400> SEQUENCE: 60
aatggcgcgg gggaagagac gaagtcctac gccgaaacct                              40

<210> SEQ ID NO 61
<211> LENGTH: 40
<212> TYPE: DNA
<213> ORGANISM: Artificial Sequence
<220> FEATURE:
<223> OTHER INFORMATION: synthetic DNA

<400> SEQUENCE: 61
gagacgaagt cctacgccga aacctaccgc ctcacggcgg                              40

<210> SEQ ID NO 62
<211> LENGTH: 40
<212> TYPE: DNA
<213> ORGANISM: Artificial Sequence
<220> FEATURE:
<223> OTHER INFORMATION: synthetic DNA

<400> SEQUENCE: 62
gtctcttccc ccgcgccatt tgccgttgcc acaggtgcgg                              40

<210> SEQ ID NO 63
<211> LENGTH: 40
<212> TYPE: DNA
<213> ORGANISM: Artificial Sequence
<220> FEATURE:
<223> OTHER INFORMATION: synthetic DNA

<400> SEQUENCE: 63
tcggcgtagg acttcgtctc tgccgttgcc acaggtgcgg                              40

<210> SEQ ID NO 64
<211> LENGTH: 40
<212> TYPE: DNA
<213> ORGANISM: Artificial Sequence
<220> FEATURE:
<223> OTHER INFORMATION: synthetic DNA

<400> SEQUENCE: 64
gtgaccctgt cgtcggagtc cttggggccg aacgacgggc                              40

<210> SEQ ID NO 65
<211> LENGTH: 40
<212> TYPE: DNA
<213> ORGANISM: Artificial Sequence
<220> FEATURE:
<223> OTHER INFORMATION: synthetic DNA

<400> SEQUENCE: 65
gtgaccctgt cgtcggagtc gcggggccg aacgacgggc                               40

<210> SEQ ID NO 66
<211> LENGTH: 40
<212> TYPE: DNA
<213> ORGANISM: Artificial Sequence
<220> FEATURE:
<223> OTHER INFORMATION: synthetic DNA

<400> SEQUENCE: 66
```

-continued

```
gtgaccctgt cgtcggagtc cttcgggccg gcgctcgaag                         40

<210> SEQ ID NO 67
<211> LENGTH: 40
<212> TYPE: DNA
<213> ORGANISM: Artificial Sequence
<220> FEATURE:
<223> OTHER INFORMATION: synthetic DNA

<400> SEQUENCE: 67
gtgaccctgt cgtcggagtc gcgcgggccg gcgctcgaag                         40

<210> SEQ ID NO 68
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Xaa is Pro-p-nitroanilide

<400> SEQUENCE: 68

Phe Arg Ala Xaa
1

<210> SEQ ID NO 69
<211> LENGTH: 5
<212> TYPE: PRT
<213> ORGANISM: Artificial Sequence
<220> FEATURE:
<223> OTHER INFORMATION: synthetic peptide

<400> SEQUENCE: 69

Ser Ala Gly Pro Lys
1               5

<210> SEQ ID NO 70
<211> LENGTH: 5
<212> TYPE: PRT
<213> ORGANISM: Artificial Sequence
<220> FEATURE:
<223> OTHER INFORMATION: synthetic peptide

<400> SEQUENCE: 70

Ser Ala Gly Pro Arg
1               5
```

PROCESS FOR PRODUCING TRANSGLUTAMINASE

This application is a Divisional of U.S. application Ser. No. 10/112,488, filed on Apr. 1, 2002, which is a Continuation of PCT/JP00/06780, filed on Sep. 29, 2000.

BACKGROUND OF THE INVENTION

The present invention relates to a process of producing a heterologous protein, especially transglutaminase, by secretory production. The heterologous proteins produced by the method include industrially useful enzymes, physiologically active proteins and others. Transglutaminase has been widely used for food processing, the manufacture of pharmaceuticals and the like.

A number of processes for the secretory production of heterologous proteins have been previously reported including those as described in the review on the secretory production of a heterologous protein by a bacterium belonging to the genus *Bacillus* [Microbial. Rev., 57, 109-137 (1993)], the review on the secretory production of a heterologous protein by methylotrophic yeast *Pichia pastoris* [Biotechnol., 11, 905-910 (1993)] and the report on the industrial production of heterologous proteins by the mould belonging to the genus *Aspergillus* [Biotechnol., 6, 1419-1422 (1988); Biotechnol., 9, 976-981 (1991)].

The transglutaminase produced by the secretory production according to one embodiment of the present invention is an enzyme which catalyzes acyltrasfer reaction of γ-carboxylamide groups in the peptide chain of the protein. When the enzyme is reacted with a protein, the formation of the cross-linkage ε-(γ-Glu)-Lys and the replacement of Gln with Glu by deamidation can be occurred. Transglutaminase has been used to manufacture gelled food products such as jelly, yogurt, cheese or gelled cosmetics and others, and to improve the quality of meat, etc (Japanese publication of examined application No. 1-50382). Moreover transglutaminase is an enzyme having industrially high usefulness in that it has been used to manufacture materials for thermostable microcapsules, carriers for immobilized enzymes etc.

Transglutaminases derived from animals and from microorganisms (microbial transglutaminase: referred to as 'MTG' hereinafter) have been previously known. The former is the calcium ion-dependent enzyme which is distributed in animal organs, skin, blood, etc. The examples include guinea pig hepatic transglutaminase (K. Ikura et al. Biochemistry 27, 2898 (1988)), human epidermal keratinocyte transglutaminase (M. A. Phillips et al. Proc. Natl. Acad. Sci. USA 87, 9333 (1990)), human blood coagulation factor XIII (A. Ichinose et al. Biochemistry 25, 6900 (1990)) and others.

For the latter, calcium-independent transglutaminases have been discovered from bacteria belonging to the *Streptoverticillium* genus, which include, for example, *Streptoverticillium griseocarneum* IFO 12776, *Streptoverticillium cinnamoneum* sub sp. *cinnamoneum* (hereinafter it can be abbreviated as *S. cinnamoneum*) IFO 12852, *Streptoverticillium mobaraense* (hereinafter it may abbreviated as *S. mobaraense*) IFO 13819 and others (Publication of unexamined Japanese patent application (JP-Kokai) No. 64-27471). The peptide mapping and the structural analysis of the genes revealed that the primary structure of the transglutaminase produced by these microorganisms shared no homology with transglutaminases from animals (European Patent application No. 0 481 504 A1).

Because microorganism-derived transglutaminase (MTG) is produced through the purification from the cultures of microorganisms such as described above, there have been problems in terms of the amount and the efficiency and the like. The production of transglutaminase using genetically engineered procedure has been also attempted. Transglutaminase proteins and the genes thereof have been reported in, for example, Biosci. Biotechnol. Biochem., 58, 82-87 (1994), Biosci. Biotechnol. Biochem., 58, 88-92 (1994), Biochimie, 80, 313-319 (1998)., Eur. J. Biochem., 257, 570-576 (1998), WO 96/06931, WO 96/22366, etc, which report the expression and production of transglutaminase in host-vector systems such as *Streptomyces lividans, Aspergillus oryzae* and *Escherichia coli*. In addition to these information, a process wherein transglutaminase is produced by secretory production in microorganisms such as *E. coli* and yeast (JP-Kokai No. 5-199883) and the method has been reported wherein MTG having activities is produced by expressing MTG as an inactive fused protein in an inclusion body within *E. coli* and subsequently solubilizing the inclusion body using protein-denaturing agents, and then, reconstituting it through the removal of the denaturing agents (JP-Kokai No. 6-30771). However, the problem has been noted that the expression level is significantly low in the secretory production by microorganisms such as *E. coli* or yeast.

On the other hand, there are examples of previous studies for the efficient secretory production of heterologous proteins using a coryneform bacterium include the secretion of nucleases and lipases [U.S. Pat. No. 4,965,197, J. Bacteriol., 174, 1854-1861 (1992)] and the secretion of proteases such as subtilisin [Appl. Environ. Microbiol., 61, 1610-1613 (1995)] by *Corynebacterium glutamicum* (hereinafter it may be abbreviated as *C. glutamicum*), a study on the secretion of cell surface proteins of a coryneform bacterium [International patent application published in Japan No. Hei 6-502548], the secretion of fibronectin-binding protein using this study [Appl. Environ. Microbial., 63, 4392-4400 (1997)], a report wherein the secretion of proteins was enhanced using a mutated secretory machinery [JP-Kokai No. 11-169182], etc., but there has been a limited number of reports on limited proteins. In light of the accumulated amount of proteins, Appl. Environ. Microbial., 61, 1610-1613 (1995) describes that about 2.5 mg/ml of protein was accumulated by expressing the alkaline protease gene from *Dichelobacter nodosus* within *C. glutamicum* using a promoter of subtilisin gene (aprE) from *Bacillus subtilis*, ribosome binding site and the sequence of a signal peptide, but U.S. Pat. No. 4,965,197, JP-Kokai No. 6-502548 or JP-Kokai No. 11-169182 do not specifically describe the values of the amount of the proteins secreted and accumulated. Furthermore, in the case of the fibronectin-binding protein [Appl. Environ. Microbiol., 63, 4392-4400 (1997)], only the secretory accumulation of the protein of about 2.5 μg/L is confirmed. Thus, there has been no reports that heterologous proteins could be efficiently accumulated in the medium at a practical level.

Additionally a genetic engineering technology for a coryneform bacterium has been developed in the system using plasmid and phage, such as the establishment of the transformation by protoplast [J. Bacteriol., 159, 306-311 (1984); J. Bacteriol., 161, 463-467 (1985)], the development of a various type of vectors [Agric. Biol. Chem., 48, 2901-2903 (1984); J. Bacteriol., 159, 306-311 (1984); J. Gen. Microbiol., 130, 2237-2246 (1984); Gene, 47, 301-306 (1986); Appl. Microbiol. Biotechnol., 31, 65-69 (1989)], the development of the regulation method of gene expression [Bio/Technology, 6, 428-430 (1988)] and the development of cosmid [Gene, 39, 281-286 (1985)]. Moreover there are reports on the cloning of genes from a coryneform bacterium [Nucleic Acids Res., 14, 10113-1011 (1986); J. Bacteriol., 167, 695-702 (1986); Nucleic Acids Res., 15, 10598 (1987); Nucleic Acids Res., 15, 3922 (1987); Nucleic Acids Res., 16, 9859 (1988); Agric. Biol. Chem., 52, 525-531 (1988); Mol. Microbiol., 2, 63-72 (1988); Mol. Gen. Genet., 218, 330-339 (1989); Gene, 77, 237-251 (1989)].

Further a transposable element derived from a coryneform bacterium has also been reported [WO93/18151; EPO445385; JP-Kokai No. 6-46867; Mol. Microbiol., 11, 739-746 (1994); Mol. Microbiol., 14, 571-581 (1994); Mol. Gen. Genet., 245, 397-405 (1994); FEMS Microbiol. Lett., 126, 1-6 (1995); JP-Kokai No. 7-107976].

The transposable element means a DNA fragment which can be transposed on the chromosome and is known to be present in a wide range of organisms ranging from prokaryotes to eukaryotes. Transposons using transposable elements have been developed [WO93/18151; JP-Kokai No. 7-107976; Mol. Gen. Genet., 245, 397-405 (1994); JP-Kokai No. 9-70291] and a heterologous gene has become to be able to be expressed using a transposon.

SUMMARY OF THE INVENTION

An object of the invention is to provide a process for the production of a heterologous protein, in particular transglutaminase by making a coryneform bacterium to produce an industrially useful heterologous protein, in particular, transglutaminase and efficiently releasing the product extracellularly (i.e., secretory production).

The inventors have found a process for the effective secretory production of industrially useful heterologous protein, in particular transglutaminase, taking notice of the fact that a pro-part as well as a signal peptide in a secretory protein of actinomycetes and the like play an important role in the secretion process.

Therefore, the present invention is a process for producing a heterologous secretory protein characterized in that a fusion protein is produced and secreted (secreto-produced) in a coryneform bacterium, wherein the heterologous secretory protein contains its pro-part ligated to the downstream of the signal peptide domain from a coryneform bacterium and then the pro-part is cleaved and eliminated.

More specifically, the invention is a process to obtain a large amount of an intended heterologous protein, in particular transglutaminase by transferring a genetic expression construct into a coryneform bacterium, wherein a gene sequence of an intended protein containing a pro-structure part, in particular, the pro-transglutaminase gene sequence, which is ligated to the downstream of a sequence encoding the signal peptide domain from a coryneform bacterium, especially the signal peptide domain of a cell surface protein, culturing the thus transformed coryneform bacterium, efficiently releasing the resulting protein extracellularly and treating the protein which is released outside the cells with a protease, etc. to cleave the pro-part.

The invention is also a process to obtain transglutaminase in which the pro-structure part of protransglutaminase is cleaved, wherein an expression construct for protease and the like are also generated in the same fashion as with the genetic construct for transglutaminase, introducing it into a coryneform bacterium together with the expression construct containing the protransglutaminase gene and culturing thus transformed coryneform bacterium, or introducing the expression construct for protease and the like into another coryneform bacterium and culturing the transformed coryneform bacterium together with the pro-transglutaminase gene-introduced bacterium, to express and secret the protransglutaminase and the protease.

As used herein, "the secretion" of a protein or peptide refers to the transportation of the protein or peptide molecule outside the bacterium cell (extracellular transportation) including the case where the protein or peptide molecule exist finally in completely free form in the medium as well as the case where only the part of the protein or peptide molecule is present outside the cell and the case where they are located on the surface of the cell.

BEST MODE FOR CARRYING OUT THE INVENTION

According to the process of the invention, a coryneform bacterium is used as a host vector system, and a large amount of transglutaminase, from which the pro-structure part is removed, may be obtained by generating an expression construct wherein a transglutaminase gene containing a pro-structure part in secretory form is ligated to the downstream of the signal peptide of cell surface protein from coryneform bacterium, introducing and expressing the construct into a coryneform bacterium, and treating the pro-structure part of the protransglutaminase secreted extracellularly with a protease and the like to cleave the pro-structure part.

According to the process of the present invention, a transglutaminase in which the pro-part is cleaved can be directly obtained extracellularly by generating a genetic expression construct for a protease and the like in a similar manner as for the protransglutaminase genetic construct, introducing and expressing it into the coryneform bacterium together with protransglutaminase genetic construct and culturing the thus transformed coryneform bacterium, or introducing the genetic expression construct for the protease and the like into another coryneform bacterium and culturing the thus transformed coryneform bacterium together with the bacterium where protransglutaminase has been introduced, and thus making the bacterium to express and secret the protransglutaminase and the protease.

A secretory protein has been generally known to be translated as a prepeptide or prepropeptide and thereafter to be formed into a mature protein. That is to say, in general, it has been known that it is translated as a peptide or prepropeptide, then the signal peptide ("a pre-part") is cleaved, thereby it is converted into a mature peptide or propeptide by further cleaving of the pro-part with a protease. As used herein, "a signal sequence" refers to the sequence which is located at the N-terminal of a secretory protein precursor and which is not present in a naturally occurring mature protein, and "a signal peptide" refers to the peptide which is cleaved from such a protein precursor. Generally, a signal sequence is cleaved coupling the extracellular secretion by a protease (generally referred to signalpeptidase). Although such a signal peptide shares certain common features in the sequence over species, a signal peptide which has secretory function in one species does not necessarily have the same secretory function in another species.

As used herein, a protein which contains both a signal peptide and a pro-part, that is, a primary translation product can be referred to "a preproprotein", and a protein which does not contain a signal peptide but does contain a pro-part can be referred to "a proprotein". A pro-part of a proprotein can be referred to "a pro-structure part" or "a pro-structure". "A pro-structure part/pro-structure" of a protein can be herein interchangeably used with "a pro-part" of a protein. A signal peptide in a preproprotein or preprotein may be derived from a different protein or be a signal peptide naturally occurring in the intended protein and it is preferably derived from a secretory protein of the host to be used. Alternatively, it may be modified to have the optimum codon depending on the codon usage of the host to be used. Moreover, the signal peptide that can be used for the purpose of the invention may contain a part of the N-terminal amino acid sequence of a naturally occurring mature protein from which the signal peptide is derived. A preproprotein can be especially called "a heterologously fused preproprotein" when the signal peptide is derived from the different protein. For example, when a protein is transglutaminase, they are referred to "preprotransglutaminase", "protransglutaminase" and "heterologously fused preprotransglutaminase", respectively. A protein in which "the propart is cleaved" is referred to a protein wherein at least one or more amino acid that constitute the pro-part is removed by cleaving the peptide bond, including a protein having identical N-terminal amino acid with the naturally occurring protein and also includes a protein having one or more extra amino acids at the N-terminal deriving from the pro-part compared to the naturally occurring protein, and a protein having shorter amino acids sequence than that of a naturally occurring mature protein, provided that the protein has an activity of the intended protein.

As is described as the prior art, a limited number of reports have been shown where the extracellular secretory production of a heterologous protein has been achieved using coryneform bacterium and the secretory production process have not been technically completed. Also, it has not been known that a coryneform bacterium extracellularly secretes a protein such as a protease by itself. The known examples are endogenous DNase [U.S. Pat. No. 4,965,197] and the facts that the cell surface protein used in the present invention falls off from the cell surface to be found outside the cell [JP-Kokai No. 6-502548]. However, any signal peptide that involves in the secretion of a protein of coryneform bacterium has not previously known except for the cell surface proteins. The only known cell surface proteins from coryneform bacterium, to date, are Genes for PS1 and PS2, the cell surface proteins of *Corynebacterium glutamicum* [JP-Kokai No. 6-502548], and the gene for SlpA, the cell surface protein of *Corynebacterium ammoniagenes* (which may be abbreviated as *C. ammoniagenes* hereinafter) [JP-Kokai No. 10-108675]. Among these proteins, PS1 and SlpA share some homology (about 30%), but almost no homology was found among others, and furthermore there found no homology in the signal sequence domain between each other. As the examples of signal sequences, the signal sequences of PS1 and PS2 from *Corynebacterium glutamicum* are shown in SEQ ID NO: 29 and SEQ ID NO: 1, and the signal sequence of SlpA from *Corynebacterium ammoniagenes* is shown in SEQ ID NO: 2.

Therefore, the inventors cloned the gene for PS2 protein from *C. glutamicum* (formerly, *Brevibacterium lactofermentum*) ATCC13869 strain and determined the sequence. It was found that there were no differences in the signal sequence domain from the known sequence from *C. glutamicum*, but that there were two different amino acids in the sequence up to the N-terminal thirty eighth amino acid residue of the mature cell surface protein (Asn for Thr residue at position 40 and Glu for Gly residue at position 55 in the amino acid sequence as, is shown in SEQ ID NO: 7). The nucleotide sequence encoding for sixty eight residues comprising thirty amino acid residues of the signal peptide and thirty eight amino acid residues from the N-terminal of the mature cell surface protein and its 5'-upstream region containing a promoter domain is shown in SEQ ID NO: 6 and the amino acid sequence is shown in SEQ ID NO: 7.

Then, the inventor examined the secretion of a heterologous protein using the region containing the promoter domain or the signal peptide domain of the cell surface protein in order to determine whether the extracellular secretory production of a large amount of the heterologous protein can be achieved in a coryneform bacterium.

Since the transglutaminase gene from actynomycetes has a high GC content and the gene from coryneform bacterium has a close GC content to the gene from actinomycetes and also they have closely similar codon usage, there is an advantage that the gene from actinomycetes can be directly used. Therefore, the inventor investigated whether a transglutaminase gene from actinomycetes can be directly used and found that the signal peptide of transglutaminase from actinomycetes did not successfully function in a coryneform bacterium. However, it is revealed that the transglutaminase gene encoding the mature protein containing the pro-structure part from actinomycetes fused with the signal peptide of the cell surface protein from a coryneform bacterium effectively functioned without any modification and was efficiently secreted outside the cell as proprotein containing the pro-structure part. When the gene for transglutaminase with the pro-structure part which additionally comprises thirty amino acid residues from the cell surface protein and thirty eight amino acid residues from the N-terminal domain of the mature cell surface protein, i.e., the gene for transglutaminase fused with the N-terminal domain of the mature cell surface protein, was used, the efficiency of the extracellular secretion of transglutaminase was further increased.

As used herein, a coryneform bacterium is an aerobic Gram-positive bacillus, which includes bacteria which was previously classified as *Brevibacterium* but currently unified as *Corynebacterium* (Int. J. Syst. Bacteriol., 41, 255 (1981)) including *Brevibacterium* which is closely related to *Corynebacterium*. An advantage in using *Corynebacterium* is that it inherently secretes extremely less proteins outside the cell compared to molds, yeasts or bacteria belonging to *Bacillus* which have been previously suitable to effect the secretion of a heterologous protein, which allow the purification process of the product to be simplified and shortened when the secretory production of a heterologous protein is conducted, and that it is excellent in terms of its medium cost, the culturing procedure and the yield, since it grows well on a simple culture medium such as those composed of ammonia, inorganic salts and so on.

Examples of *Corynebacterium* which can be used as a host bacterium in the present invention include wild type strains including *Brevibacterium saccharolyticum* ATCC14066, *Brevibacterium immariophilum* ATCC14068, *Brevibacterium lactofermentum* (*Corynebacterium glutamicum*) ATCC13869, *Brevibacterium roseum* ATCC13825, *Brevibacterium flavum* (*Corynebacterium glutamicum*) ATCC14067, *Corynebacterium acetoacidophilum* ATCC13870, *Corynebacterium glutamicum* ATCC13032, *Corynebacterium lilium* (*Corynebacterium glutamicum*) ATCC15990, *Brevibacterium ammoniagenes* (*Corynebacterium ammoniagenes*) ATCC6871, and mutant strains derived from these wild type strains, for example, mutant strains defective in the ability to produce glutamate, mutant strains for amino acids production such as lysine and the like, and mutant strains modified to produce other substances such as nucleic acids, for example, inosine.

The genetic construct which can be used in the present invention generally includes a promoter, a sequence encoding a proper signal peptide and a nucleic acid fraction encoding an intended protein, and a regulatory sequence (a operator or terminator, etc.) necessary to express the gene for the intended protein in a coryneform bacterium, at a proper position such that they can function. The intended protein may have a pro-structure part at the N-terminal. Vectors which can be used for this construct are not particularly limited and include any one which can function in a coryneform bacterium, and they may be those which autonomously multiply such as plasmids or vectors which are integrated into the chromosome of the bacterium. Plasmids derived from coryneform bacteria are particularly preferable. These include, for example, pHM1519 (Agric. Biol. Chem., 48, 2901-2903 (1984)), pAM330 (Agric. Biol. Chem., 48, 2901-2903 (1984)), and plasmids obtained by modifying them which possess drug-resistant genes. Artificial transposons and the like can be also used. When a transposon is used, the intended gene is introduced in the chromosome through homologous recombination or by its own transposing ability.

Promoters which can be used in the invention are not particularly limited. Any promoter which can function in the cell of a coryneform bacterium can be generally used. It may be also a promoter derived from a different species, for example, a promoter derived from *E. coli*, such as tac promoter, etc. Among these promoters, a potent promoter is more preferably, such as tac promoter, etc. Examples of promoters derived from a coryneform bacterium include promoters for the genes of cell surface proteins PS1, PS2 and SlpA, promoters for the genes in biosynthetic systems of different amino acids, for example, glutamate dehydrogenase gene in the glutamic acid biosynthetic system, glutamine synthetase gene in the glutamine synthetic system, aspartokinase gene in the lysine biosynthetic system, homoserine dehydrogenase gene in the threonine biosynthetic system, acetohydroxylate synthase gene in the isoleusine and valine biosynthetic system, 2-isopropylmalate synthase gene, glutamate kinase gene in the proline and arginine synthetic system, phosphoribosyl-ATP pyrophopholylase gene in the histidine biosynthetic synthesis, deoxyarabinohepturonic acid phosphate (DAHP) synthase gene in the aromatic amino acid biosynthetic system such as tryptophan, tyrosine and phenylalanine, etc., phosphoribosylpyrophosphate (PRPP) amidotransferase gene, inosinate dehydrogenase gene and guanylate synthase gene in the nucleic acid biosynthetic system such as inosinate and guanylate.

The signal peptide which is used in the present invention is the signal peptide of a secretory protein from the host, *Coryneform bacterium*, and preferably it is the signal peptide of a cell surface protein from a *Coryneform bacterium*. Cell surface proteins include PS1 and PS2 derived from *C. glutamicum* (JP-Kokai No. 6-502548), and SlpA derived from *C. ammoniagenes* (JP-Kokai No. 10-108675). The amino acid sequence of PS1 is shown in SEQ ID NO:29, the amino acid sequence of PS2 in SEQ ID NO:1 and the amino acid sequence of SlpA in SEQ ID NO:2. Additionally, it is reported that DNase from a coryneform bacterium also has a signal peptide, as described in U.S. Pat. No. 4,965,197, which can be used in the present invention.

To the signal peptide, a portion of N-terminal amino acid sequence of the secretory protein from which the signal peptide derives may be connected. The signal sequence is cleaved by a signalpeptidase during the translated product is secreted extracellularly. In addition, the gene encoding the signal peptide can be used either in native form or in modified form to contain the optimum codons depending on the codon usage in the host to be used.

When these signal peptides are used, the genes encoding for intended proteins are ligated to the 3'-terminal of the genes encoding the signal peptides and are located such that they are subjected to the regulation of expressions by the promoters described above.

The useful proteins which can be secreto-produced according to the present invention essentially includes, but are not limited to, all of the secretory proteins derived from animals and plants and microorganisms. For example, proteins such as protease, aminopeptidase, carboxypeptidase, collagenase and chitinase can be secreto-produced according to the present invention. Proteins which are prepared by the secretory production according to the present invention are preferably naturally occurring secretory proteins, more preferably proteins having additional pro-structure parts. Transglutaminase is particularly preferred as a useful protein prepared by the secretory production according to the present invention. As transglutaminase genes, for example, genes for secretory transglutaminase derived from actinomycetes, for example, *S. mobaraense* IFO 13819, *S. cinnamoneum* IFO 12852, *Streptoverticillium griseocarneum* IFO 12776, *Streptomyces lydicus* [WO9606931], etc. and molds such as *Oomyceted* [WO9622366], etc can be used for the purpose of the present invention. The genes encoding these proteins can be modified depending on the type of the host to be used and in order to achieve the desired activity, and comprise the addition, deletion, replacement of one or more amino acid residues and optionally may be converted into the optimum codon depending on the frequency of codon usage in the host.

When the protein prepared by the secretory production according to the present invention is the protein naturally expressed as a prepropeptide, the gene fragment encoding the proprotein containing the pro-structure part (pro-part) is preferably used. As examples of the sequences of the pro-parts, the sequences of the pro-structure parts of transglutaminases derived from actinomycetes are shown in SEQ ID NO:3 (derived from *S. mobaraense*) and SEQ ID NO:4 (derived from *S. cinnamoneum*). The pro-part of the protein may be cleaved by appropriate means, for example by proteases. Aminopeptidase, endopeptidase which cleaves it at a proper position, or more specific protease can be used. Preferably, the proteases which cleave the protein such that the resulting protein has an equivalent to or more activity than that of the naturally occurring protein. Alternately the gene sequence encoding the intended protein or the pro-structure part of the intended protein can be also modified and designed to express the protein having the recognition site for protease specific to the desired location. General molecular biotechnological procedures including such modification techniques, gene cloning techniques and detection techniques for the produced proteins are well known to those skilled in the art and reference can be made to Sambrook et al., 1989, Molecular Cloning: A Laboratory Manual, Second Edition (1989) Cold Spring Harbor Laboratory Press, Cold Spring Harbor, N.Y., DNA Cloning: A Practical Approach, Volumes I and (D. N. Glover ed. 1985), F. M. Ausubel et al. (eds), Current Protocols in Molecular Biology, John Wiley & Sons, Inc. (1994), PCR Technology: Principles and Application for DNA Amplification, H. Erlich, ed., Stockton Press and etc.

Examples of pro-structure parts having the modified pro-structure parts which are shown in SEQ ID NO:3 and SEQ ID NO:4 includes the modified pro-structure parts as described in SEQ ID NO:30 to SEQ ID NO:38.
s
Sequence List Free Texts
SEQ ID NO:30 to SEQ ID NO:37: the modified pro-structure part of transglutaminase from *S. mobaraense*
SEQ ID NO:38: the chimera of transglutaminase pro-structure parts of *S. mobaraense* and *S. cinnamoneum*
These modified pro-structure parts have the following features:
SEQ ID NO:30=AP at the C-terminal of the pro-structure part from *S. mobaraense* (45 amino acid residues) is deleted;

SEQ ID NO:31=FRAP at the C-terminal of the pro-structure part from *S. mobaraense* (45 amino acid residues) is deleted;

SEQ ID NO:32=D at the N-terminal of the pro-structure part from *S. mobaraense* (45 amino acid residues) is deleted;

SEQ ID NO:33=DNGAGE at the N-terminal of the pro-structure part from *S. mobaraense* (45 amino acid residues) is deleted;

SEQ ID NO:34=RAP at the C-terminal of the pro-structure part form *S. mobaraense* (45 amino acid residues) is modified to GPK;

SEQ ID NO:35=RAP at the C-terminal of pro-structure part from *S. mobaraense* (45 amino acid residues) is modified to GPR;

SEQ ID NO:36=GPSFRAP at the C-terminal of the pro-structure part form *S. mobaraense* (45 amino acid residues) is modified to GPK (FRAP is deleted and S at the C-terminal is modified into K);

SEQ ID NO:37=GPSFRAP at the C-terminal of the pro-structure part from *S. mobaraense* (45 amino acid residues) is modified to GPR (FRAP is deleted and S at the C-terminal is modified into S);

SEQ ID NO:38=the chimeric pro-structure part (56 amino acid residues) consisting of the partial pro-structure parts from *S. mobaraense* (15 amino acid residues) and the partial pro-structure parts *S. cinnamoneum* (41 amino acid residues).

Thus the pro-structure part may have replacement, deletion, insertion or addition of one or more amino acids as long as it has the recognition site specific to protease at given position.

The N-terminal region of the protein generated by protease degradation may not be necessarily identical to that of the naturally occurring protein and one to several amino acids may be further added to or deleted from the naturally occurring protein.

Generally it is preferred that the resulting protein is cleaved at the appropriate same position as that of a naturally occurring protein in terms of its activity and it is more preferred that it is identical to the mature peptide of a naturally occurring protein. For example, the sequences of mature transglutaminases of *S. mobaraense* and *S. cinnamoneum* are shown in SEQ ID NO:5 and SEQ ID NO:43, respectively. Therefore the specific proteases which cleaves the propeptide at the position such that it generate the same protein as the naturally occurring mature protein are generally most preferable. However, for a particular objective the peptides having longer or shorter sequence of amino acid residue by from one to several residues at the N-terminal relative to that of a naturally occurring protein may possess more appropriate activity. Such proteases include, for example, Dispase (available from Boeringer Manheim Co.) which can be commercially available and proteases obtained from the culture medium of microorganisms, such as, for example, the culture medium of actinomycetes. Such proteases may be used in a unpurified state or optionally may be used after purification to the appropriate purity.

An example of other suitable protease is SAMP45, a serine protease produced by *Streptomyces albogriseolus* (hereinafter it may be abbreviated as *S. albogriseolus*). In the case of the protransglutaminase from *S. mobaraense*, since SAMP45 predominantly cleaves between Ser at position 41 and Phe at position 42 of the pro-structure part as defined in SEQ ID NO: 3, the protein, which has the structure wherein the additional four amino acids of Phe-Arg-Ala-Pro of the C-terminal form the pro-structure part is added to the N-terminal of the naturally occurring mature transglutaminase shown in SEQ ID NO: 5, is generated. The present inventors confirmed that these proteins also had the activities of transglutaminase. The sequence of SAMP45 gene has been already determined and the amino acid sequence of the protein with the additional pro-structure part (proSAMP45) is shown in SEQ ID NO:39 (J. Bacteriol., 179, 430-438 (1997)), as well. When SAMP45) is allowed to act on the protransglutaminase in the form of the culture medium of *S. albogriseolus* or in the form of *S. Albogriseolus* cell, it can cleave the pro-structure part leaving a part thereof remained, resulting in the transglutaminase wherein almost all of the pro-structure part is removed. Alternatively the transglutaminase wherein a large part of the pro-structure part is removed can be similarly obtained by co-culturing a coryneform bacterium to which prepro-SAMP45 gene has been introduced with a coryneform bacterium that secreto-produces protransglutaminase.

Additionally the activation of the transglutaminase through the cleavage of the pro-structure part can be efficiently performed by similarly introducing the SAMP45 gene into the Coryneform bacterium into which the preprotransglutaminase gene has been introduced and by allowing to simultaneously secreto-produce the SAMP45 as well as the protransglutaminase.

Further mature transglutaminase identical to the naturally occurring transglutaminase can be obtained by using the proline-specific peptidase produced by *S. mobaraense* (svPEP), which has been found by the inventors, combined with SAMP45, which results in the removal of the four amino acids of Phe-Arg-Ala-Pro added at the N-terminal.

This svPEP is an enzyme that cleaves specifically the peptides or the peptide analogues represented by the following formula (I) at the site shown with ↓ in the formula, that is, at the carboxyl terminal side of the third or fourth proline residue from the N-terminal:

$$Y\text{-Pro-}\downarrow\text{-}Z \quad (I)$$

wherein Y represents an oligopeptide consisting of two or three amino acid residues and Z represents an amino acid, peptide, amide or ester.

More specifically this proline-specific peptidase is a proline-specific peptidase having the following properties shown in (1)-(8):

(1) It cleaves at least one of the following proline containing peptides at the site shown with ↓, that is, at the carboxyl terminal side of the proline residue (wherein pNA is p-nitroanilide):

Ala-Ala-Pro-↓-pNA, Ala-Phe-Pro-↓-pNA, Phe-Arg-Ala-Pro-↓-pNA (identical to Phe-Arg-Ala Xaa (SEQ ID NO:68) (wherein Xaa represents Pro-pNA and pNA represents p-nitoroanilide))

(2) It has the optimum pH of 6.0-6.5;
(3) It is stable at pH4-9;
(4) It has the optimum temperature of 25-30° C.;
(5) It is stable below 20° C.;
(6) Its activity is inhibited by phenylmethylsulfonyl fluoride, aminoethylbenzenesulfonylfluoride hydrochloride;
(7) It has the isoelectric point of 10.2; and
(8) It has the molecular weight of approximately 50,000

For example, this svPEP can be prepared as described hereinafter. Actinomycetes which produces the peptidases having svPEP activities, for example, actinomycetes *S. mobaraense* IFO13819 is cultured according to the method conventionally used for the cultivation of actinomycetes. The culture medium for culturing actinomycetes IFO13819 may be the common medium containing conventional carbon sources, nitrogen sources, inorganic ions and others. Glucose, starch, sucrose and others can be used as the carbon sources.

Peptone, yeast extract, meat extract, malt extract, ammonium salt and others are optionally used as the nitrogen sources if necessary. Cultures may be incubated under the aerobic condition which is appropriately controlled within, for example, the pH range of between pH 5.0 and 8.5 and the temperature range between 15 to 37° C. The culture period is usually as long as 1 to 10 days, although it depends on the temperature, pH and the type of medium. In principle, the culture may be terminated at the time when the maximum amount of the intended svPEP can be achieved.

After the incubation of the culture for the period described above, the purified svPEP preparation can be obtained by recovering the cells from the culture, washing them briefly, eluting the fraction containing svPEP from the surface of the cells and purifying the eluent with the combination of purification techniques as HPLC and FPLC well known to those skilled in the art which is conventionally used for purifying proteins such. The elution of svPEP fraction from the surface of the cells can be performed by shaking the cells in a buffer solution such as, for example, 0.1 M of sodium phosphate buffer (pH 7.0) for a given period as long as 1 to 5 hours.

The temperature during the procedure is between 0 to about 5° C. to prevent the inactivation of the enzyme. svPEP can be isolated and purified from the supernatant of the cultures, but it contains a lot of contaminated proteins and therefore it is more advantageous to eluted and purify the protein from the surface of the washed cells.

The active fractions in each step can be confirmed by determining the activities of the enzyme in the fractions. The determination of the activities can be achieved using a combination of appropriate substrates and the detection method of the reaction products, for example, by reacting the enzymes with Ala-Ala-Pro-pNA, Ala-Phe-Pro-pNA, Phe-Arg-Ala-Pro-pNA as substrates and measuring the amount of the pNA (p-nitroanilide) released from the reaction to quantify the activities.

The genes encoding svPEP can be obtained by determining the partial amino acid sequence and designing appropriate probes, optionally after further purifying svPEP, which has been purified as previously described, by using reversed phase chromatography, etc. This procedure is well known to those skilled in the art. See, e.g., Molecular Cloning 2nd edition [J. Sambrook E. F. Fritsch and T. Maniatis, Cold Spring Harbor Laboratory Press, p9. 31 (1989)]. The sequence of the gene for svPEP obtained in this way and the entire sequence of the amino acid coded thereby are shown in SEQ ID NO: 41 and SEQ ID NO: 42, respectively, and the amino acid sequence of the mature protein of svPEP are shown in SEQ ID NO:40.

When svPEP is reacted on the protransglutaminase together with the protease in the form of medium of S. mobaraense or S. mobaraense cells, the pro-structure part can be cleaved completely, resulting in the mature transglutaminase of which pro-structure part is completely removed. Alternatively, the mature transglutaminase of which pro-structure part is completely removed can be similarly obtained by culturing a coryneform bacterium wherein pre-pro svPEP gene and a protease gene are introduced together with a coryneform bacterium which releases a protransglutaminase extracellularly by secretory production. Moreover a mature transglutaminase having the same structure as that of a naturally occurring form can be efficiently produced by introducing similarly both SAMP45 gene and svPEP gene into a coryneform bacterium to which pre-protransglutaminase gene has been introduced, and by allowing it to secreto-produce protransglutaminase and SAM45 as well as svPEP extracellularly or at the surface of the cells.

The method for introducing the genetic constructs that can be used in the present invention into a coryneform bacterium is not limited to particular methods and the methods generally used including, for example, the protoplast method (Gene, 39, 281-286 (1985)), the electroporation method (Bio/Technology, 7, 1067-1070) (1989)), etc. The resulting transformant can be cultured according to the conventional methods and conditions. For example, the transformant can be cultured with a conventional medium containing carbon sources, nitrogen sources and inorganic sources. Trace amount of organic nutrients such as vitamins and amino acids can be optionally added to the medium in order to achieve the growth to greater extent.

Carbohydrates such as glucose and sucrose as carbon sources, organic acids such as acetic acid, alcohols and others can be used. Gaseous ammonia, aqueous ammonia, ammonium salt and others can be used as nitrogen sources. As inorganic ions, calcium ion, magnesium ion, phosphorus ion, potassium ion, ferrous or ferric ion and others are optionally used as necessary. The culture is conducted for about 1 to 7 days under the aerobic condition in the appropriate range of pH between 5.0 and 8.5 and of the temperature between 15° C. and 37° C. By culturing the transformant under such conditions, a large amount of an intended protein is produced intracellularly and is efficiently secreted extracellularly. Transglutaminase is generally known to be lethal when it is largely accumulated in the cells of microorganisms, but according to the present invention, transglutaminase is continuously produced without generating lethal effects, since the intracellularly produced transglutaminase is released extracellularly.

The proteins which are secreted in the medium according to the present invention can be isolated and purified from incubated culture medium according to the methods well known to those skilled in the art. For example, the proteins can be isolated and purified by removing the cells from the medium by centrifugation, etc., and then by using known appropriate methods such as salting-out, ethanol precipitation, ultrafiltration, gel filtration chromatography, ion-exchange column chromatography, affinity chromatography, medium high-pressure liquid chromatography, reversed-phase chromatography, hydrophobic chromatography or the combination thereof. The proteins secreted at the surface of the cells according to the present invention can be isolated and purified by using the methods well known to those skilled in the art, for example, by solubilizing them with increased salt concentrations or surfactants, and then using the similar methods to that for the proteins secreted in the medium. Additionally in some cases the proteins secreted at the surface of the cell may be used without solubilization, for example, as immobilized enzymes.

The present invention is further specifically described in the following Examples, which are not to be construed in any way as the limitation of the present invention.

EXAMPLES

Example 1

Expression of Prepro-transglutaminase Derived from S. mobaraense IFO13819 in C. glutamicum ATCC13869

(1) Acquisition of the Transglutaminase Gene Derived from S. mobaraense IFO13819

The sequence of transglutaminase gene derived from S. mobaraense DSMZ strain has been already determined [Eur.

J. Biochem., 257, 570-576 (1998)]. The primers shown in SEQ ID NO: 8 and SEQ ID NO: 9 were synthesized by reference to the sequence and the region encoding the sequence of mature transglutaminase was amplified using PCR method with the chromosomal DNA of *S. mobaraense* IFO13819 prepared according to the conventional procedure (the method of Saito and Miura [Biochim, Biophys. Acta, 72, 619 (1963)]. For PCR reaction, Pyrobest DNA polymerase (Takarashuzo Co. Ltd.) was used and the reaction condition followed the protocol recommended by the manufacturer.

```
5'-GACTCCGACGACAGGGTCACCCCTCCCGCC-3' (SEQ ID NO: 8)

5'-CGCTCACATCACGGCCAGCCCTGCTTTACC-3' (SEQ ID NO: 9)
```

<Sequence Listing Free Text>
SEQ ID NO: 8 and SEQ ID NO: 9: PCR Primer

The DNA probe was then generated by reacting the amplified DNA fragment of about 1.0 kb with [$\alpha$-$^{32}$P]dCTP using Random Primer DNA Labeling Kit Ver. 2 (Takarashuzo Co. Ltd.) according the protocol attached to the Kit. It was confirmed that the transglutaminase gene was present in the fragment of about 4 kb excised with restriction enzyme Sac I by Southern blot hybridization using the generated probe and the chromosomal DNA of *S. mobaraense* IFO13819 according to the conventional method, as described in Molecular Cloning 2nd edition [J. Sambrook, E. F. Fritsch and T. Maniatis, Cold Spring Harbor Laboratory Press, p9. 31 (1989)].

Accordingly, the fragment of about 4 kb which had been generated by SacI digestion of the chromosomal DNA of *S. mobaraense* IFO13819 was recovered through agarose gel electrophoresis using EASYTRAP Ver. 2 (Takarashuzo Co. Ltd.) and was inserted into Sac I site of pUC18 (Takarashuzo Co. Ltd.) which was introduced into competent cells of *Escherichia coli* JM109 (Takarashuzo Co. Ltd.) to generate a library.

The bacterium strain was obtained which contains the plasmid where the transglutaminase gene fragment was cloned, by screening the library using the previously generated DNA probe for transglutaminase by colony hybridization as described in Molecular Cloning 2nd edition [J. Sambrook, E. F. Fritsch and T. Maniatis, Cold Spring Harbor Laboratory Press, p1. 90 (1989)]. The plasmid was recovered from this strain and designated as pUITG. The sequence of the fragment cloned in pUITG was determined, which confirmed that the transglutaminase gene from *S. mobaraense* IFO13819 had the same sequence as that of the transglutaminase from *S. mobaraense* DSMZ strain.

The determination of the nucleotide sequence revealed that the SacI fragment of about 4 kb was the incomplete DNA fragment from which the signal sequence (the pre-part) was partially deleted. Accordingly the cloning of the promoter region and the entire signal sequence region was attempted. The cloning was performed using TAKARA LA PCR in vitro Cloning kit (Takarashuzo Co. Ltd.) and the synthesized primers shown in SEQ ID NO: 10 and SEQ ID NO:11 according to the attached protocol.

```
    5'-GTGACCCTGTCGTCGGAGTC-3'      (SEQ ID NO: 10)

5'-GGCATCCTGTCGAGCGGCTC-3'      (SEQ ID NO: 11)
```

<Sequence Listing Free Text>
SEQ ID NO: 10 and SEQ ID NO: 11: PCR Primers for the Promoter Region and the Signal Sequence of *S. mobaraense*

Consequently when a cassette primer of SalI was used, the PCR-amplified fragment of about 800 by was obtained and the sequencing of the fragment confirmed that the fragment contained the promoter region and the signal sequence region for the transglutaminase gene. Accordingly, the PCR-amplified fragment of about 800 by was inserted into SmaI site of pVC7 described in JP-Kokai No. 9-070291 to obtain pVITGS5. Additionally plasmid pUITG was digested with SacI, the fragment of about 4 kb was recovered through agarose electrophoresis, and the fragment was inserted to SacI site of pVITGS5 to construct plasmid pVITGC which comprises the full-length transglutaminase gene. The determination of the nucleotide sequence was performed using Dye Terminator Cycle Sequencing kit (PE Applied Biosystems) and DNA Sequencer 373A (PE Applied Biosystems). The sequence of the preprotransglutaminase gene is shown in SEQ ID NO: 12, wherein the N-terminal 31 amino acids sequence was believed to be the signal sequence (the pre-part). The amino acid sequence of the preprotransglutaminase is shown in SEQ ID NO: 13.

(2) Conversion of the Promoter Region of Transglutaminase Gene

The sequence of the gene for PS2 which is a surfaced protein of *C. glutamicum*. has been already determined [Mol. Microbiol., 9, 97-109 (1993)]. Primers shown in SEQ ID NO: 14 and SEQ ID NO:15 were synthesized on referring to the sequence, and the region which comprises the promoter at the 5'-upstream region of the initiation codon of PS2 protein gene was amplified using PCR method from the chromosomal DNA of *C. glutamicum* ATCC13869 prepared according to a conventional method.

```
                                      (SEQ ID NO: 14)
5'-AAATTCCTGTGAATTAGCTGATTTAG-3'

(SEQ ID NO: 15)
5'-GAGCTCTCCGGCGTATGCGCATAGAGGCGAAGGCTCCTTGAATA-3'
```

<Sequence Listing Free Text>
SEQ ID NO: 14 and SEQ ID NO:15: PCR Primers

On the other hand, primers shown in SEQ ID NO: 16 and SEQ ID NO: 9 were synthesized based on the sequence of the transglutaminase gene determined in Example 1(1), and the region of the preprotransglutaminase gene was amplified using PCR method from pUITG obtained in Example 1(1).

```
                                      (SEQ ID NO: 16)
    5'-ATGCGCATACGCCGGAGAGCTCTCGTCTTC-3'
```

<Sequence List Free Text>
SEQ ID NO: 16: PCR Primer

Then, the fusion gene of transglutaminase fused with the additional pre-pro structure part, which was ligated to the region comprising the promoter of the cell surface protein gene from *C. glutamicum* ATCC13869, was amplified by performing cross-over PCR with SEQ ID NO: 14 and SEQ ID NO: 9 using the mixture of 1 µl of each of the PCR solution of the amplified region comprising the promoter of PS2 gene of *C. glutamicum* ATCC13869 and the amplified pre-protransglutaminase gene region, as the templates. The amplified fragment of about 1.8 kb was detected by agarose gel electrophoresis. This fragment was recovered from the agarose gel with EASYTRAP Ver. 2 (Takarashuzo Co. Ltd.) and inserted into SmaI site of pVC7 as described in JP-Kokai No. 9-070291 to obtain pVKPTG0. The nucleotide sequence of the inserted fragment was determined according to the method described above and it was confirmed that the fusion gene was constructed as expected.

(3) Expression of the Pre-protransglutaminase Gene in *C. glutamicum* ATCC13869

*C. glutamicum* ATCC13869 was transformed with the pVITGC constructed in Example 1(1) (both the promoter and the pre-protransglutaminase gene were derived from *S. mobaraense*) or with the pVKPTGO constructed in Example 1(2) (the promoter was derived from PS2 gene of *C. glutamicum* ATCC13869 and the pre-protransglutaminase gene was derived from *S. mobaraense*) and the strains grown on the CM2S agar medium comprising 5 mg/l of chloramphenicol (10 g of yeast extract, 10 g of tryptone, 5 g of sucrose, 5 g of NaCl, 5 g of agar per liter of distilled water) were selected. The selected *C. glutamicum* ATCC13869 harboring pVITGC or pVKPTGO was cultured in MM culture medium (30 g of glucose, 0.4 g of magnesium sulfate heptahydrate, 30 g of ammonium sulfate, 1 g of potassium dihydrogenphosphate, 0.01 g of ferrous sulfate heptahydrate, 0.01 g of manganese(II) sulfate pentahydrate, 200 µg of thiamine hydrochloride, 500 µg of biotin, 0.15 g of DL-methionine, 50 g of calcium carbonate per liter of distilled water, adjusted to pH 7.5) comprising 5 mg/l of chloramphenicol at 30° C. for 48 hours, respectively. After the incubation was finished, 10 µl of the supernatant of the culture was subjected to SDS-PAGE and then to Western blot with anti-transglutaminase antibody as described in Biosci. Biotechnol. Biochem., 58, 82-87 (1994) according to the conventional method (for example, the general procedure as described in J. Sambrook et al. (1989)(supra)).

Consequently, the secretion of transglutaminase could not be detected. From the above results, it was confirmed that the signal sequence of transglutaminase from *S. mobaraense* did not function in *C. glutamicum* ATCC13869.

Example 2

Secretory Production of Mature Transglutaminase Using the Fusion Gene Encoding the Signal Peptide of the Cell Surface Protein of *Corynebacterium glutamicum* (*C. glutamicum* ATCC13869) and the Mature Transglutaminase Derived from *S. mobaraense* IFO13819

(1) Construction of the Transglutaminase Gene Containing the Signal Sequence of Cell Surface Protein of *C. glutamicum* ATCC13869

The sequence of the gene of PS2 which is the cell surface protein of *C. glutamicum* has been already determined [Mol. Microbiol., 9, 97-109 (1993)]. Primers shown in SEQ ID NO: 14 and SEQ ID NO:17 were synthesized on referring to the sequence, and the region encoding the N-terminal 44 amino acid residues (30 amino acid residues of the signal peptide and 14 amino acid residues of the mature cell surface protein) of the protein corresponding to PS2 and 5'-upstream region containing the promoter region were amplified using PCR method with the chromosomal DNA of *C. glutamicum* ATCC13869 prepared according to the method described in Example 1(2). The primer shown in SEQ ID NO: 17 also comprises the sequence encoding the amino acid sequence from the N-terminal region of the mature transglutaminase in order to construct the fusion gene fused with transglutaminase.

```
                                          (SEQ ID NO: 14)
5'-AAATTCCTGTGAATTAGCTGATTTAG-3'

(SEQ ID NO: 17)
5'-GGGGTGACCCTGTCGTCGGAGTCGTTGAAGCCGTTGTTGATGTT
GAA-3'
```

<Sequence Listing Free Text>
SEQ ID NO: 17: PCR Primer

On the other hand, primers shown in SEQ ID NO: 8 and SEQ ID NO: 9 were synthesized based on the sequence of the transglutaminase gene determined in Example 1(1) and the region of mature transglutaminase gene was amplified using PCR method with pUITG obtained in Example 1(1).

The fusion gene of the mature transglutaminase, which was ligated to the region encoding the N-terminal 44 amino acid residues of *C. glutamicum* ATCC13869 and to the 5'-upstream region comprising the promoter gene of the cell surface protein gene, was amplified by performing cross-over PCR with SEQ ID NO: 14 and SEQ ID NO: 9 using the mixture of 1 µl of PCR solution of the amplified region encoding the N-terminal 44 amino acid residues of the protein corresponding to PS2 of *C. glutamicum* and the 5'-upstream region containing the promoter, and 1 µl of PCR solution of the amplified the mature transglutaminase gene region, as the templates.

The amplified fragment of about 1.7 kb was detected by agarose electrophoresis. This fragment was recovered from the agarose gel using EASYTRAP Ver. 2 (Takarashuzo Co. Ltd.) and inserted into SmaI site of the pVC7 described in JP-Kokai No. 9-070291 to obtain pVKPTG3. The nucleotide sequence of the inserted fragment was determined according to the method described above and it was confirmed that the expected fusion gene was constructed.

Additionally, the fusion mature transglutaminase gene of about 1.7 kb, which had been ligated to the region encoding the N-terminal 44 amino acid residues from *C. glutamicum* ATCC13869 and the 5'-upstream region comprising the promoter of the cell surface protein gene, was excised by digesting pVKTG3 with KpnI and XbaI and recovered using agarose electrophoresis. This fragment was inserted into the KpnI-XbaI site of pPK4 described in JP-Kokai No. 9-322774 to construct pPKTG3.

(2) Secretion of Mature Transglutaminase Using the Signal Sequence of the Cell Surface Protein of *C. glutamicum* ATCC13869

*C. glutamicum* ATCC13869 was transformed with the constructed plasmid pVKTG3 or pPKTG3 (in both cases the gene comprising the promoter and the gene encoding signal peptide and the N-terminal 14 amino acid residues were derived from *C. glutamicum* ATCC13869, and the mature transglutaminase gene was derived from *S. mobaraense*) and the strains grown on the CM2S agar medium comprising 5 mg/l of chloramphenicol or 25 mg/l of kanamycin were selected. The selected *C. glutamicum* ATCC13869 containing pVITG3 or pVKPTG3 was then cultured in liquid MM culture medium, described above, comprising 5 mg/l of chloramphenicol or 25 mg/l of kanamycin at 30° C. for 48 hours, respectively. After the incubation was finished, 10 µl of the supernatant of the culture was subjected to SDS-PAGE and then Western blot was performed according to a conventional method with anti-transglutaminase antibody as described in Biosci. Biotechnol. Biochem., 58, 82-87 (1994). As a result, a small amount of secreted transglutaminase having the similar molecular weight to that of the mature transglutaminase could be detected in the supernatant of the culture of both strains.

Example 3

Secretory Production of Pro-transglutaminase using Pro-transglutaminase Fusion Gene (Heterologously Fused Prepro-transglutaminase Fusion Gene) Derived from *S. mobaraense* IFO13819 Ligated to the Signal Peptide of Cell Surface Protein of *C. glutamicum* ATCC13869

(1) Construction of Transglutaminase Gene (Heterologously Fused Prepro-transglutaminase Fusion Gene) Containing the Additional Pro-Structure Part with the Signal Peptide of Cell Surface Protein of *C. glutamicum* ATCC13869

Primers shown in SEQ ID NO:18, SEQ ID NO: 19, SEQ ID NO: 20 and SEQ ID NO: 21 were synthesized on referring to the sequence of the gene of PS2 which was the cell surface protein of *C. glutamicum* [Mol. Microbiol., 9, 97-109(993)]. The coding region for the N-terminal 30, 31, 44 or 68 amino acid residues (the region comprising 30 amino acid residues of the signal peptide) and the 5'-upstream region containing the promoter region of the protein corresponding to PS2 were amplified by PCR method using the combination of SEQ ID NO: 14 and SEQ ID NO: 18, or of SEQ ID NO: 14 and SEQ ID NO: 19, or of SEQ ID NO: 14 and SEQ ID NO: 20, or of SEQ ID NO: 14 and SEQ ID NO: 21 from the chromosomal DNA of *C. glutamicum* ATCC13869 prepared according to the method described in Example 1(2).

Primers shown in SEQ ID NO: 18, SEQ ID NO: 19 and SEQ ID NO: 21 comprise the sequences encoding the N-terminal amino acids of pro-transglutaminase in order to construct the fusion gene fused with the transglutaminase having the pro-structure part.

```
                                       (SEQ ID NO: 18)
5'-CTTCGTCTCTTCCCCCGCGCCATTGTCAGCGAATGCTGGGATAGCAA
CGCC-3'

(SEQ ID NO: 19)
5'-CTTCGTCTCTTCCCCCGCGCCATTGTCCTGAGCGAATGCTGGGATAG
CTAC-3'

(SEQ ID NO: 20)
5'-CTTCGTCTCTTCCCCCGCGCCATTGTCGTTGAAGCCGTTGTTGATGT
TGAA-3'

(SEQ ID NO: 21)
5'-CTTCGTCTCTTCCCCCGCGCCATTGTCAGTCAGGTCGCGGAGGGTTT
CCTC-3'
```

<Sequence Listing Free Text>
SEQ ID NO: 18 to SEQ ID NO: 21: PCR Primers

On the other hand, primers shown in SEQ ID NO: 22 and SEQ ID NO: 9 were synthesized based on the sequence of the transglutaminase gene determined in Example 1(1) and the pro-transglutaminase gene region was amplified using PCR method with pUITG obtained in Example 1(1).

```
                                       (SEQ ID NO: 22)
5'-GACAATGGCGCGGGGAAGAGACGAAGTCC-3'
```

<Sequence Listing Free Text>
SEQ ID NO: 22: PCR Primer

Then the heterologously fused pro-transglutaminase gene ligated to the respective region encoding its N-terminal 30, 31, 44 and 68 amino acid residues and the 5'-upstream region comprising the promoter region of the protein gene corresponding to PS2 from *C. glutamicum* ATCC13869, that is, the fragments of heterologously fused prepro-transglutaminase genes which were ligated to the promoter of the gene for cell surface protein of *C. glutamicum* ATCC13869, was amplified by performing cross-over PCR with SEQ ID NO: 14 and SEQ ID NO: 9 using the mixture which comprises 1 µl of PCR solution of the 5'-upstream region containing the promoter region of the gene of the protein corresponding to PS2 of *C. glutamicum* ATCC13869 and each of the amplified region encoding N-terminal 30, 31, 44 or 68 amino acid residues of the protein, and 1 µl of PCR solution of the amplified region of the gene for the transglutaminase having the pro-structure part, as the templates.

The amplified fragments ranging about 1.8 kb to 1.9 kb was detected by agarose electrophoresis. These fragments were recovered from the agarose gels with EASYTRAP Ver. 2 (Takarashuzo Co. Ltd.) and inserted into SmaI site of pVC7 as described in JP-Kokai No. 9-070291 to obtain pVKPTG1, pVKPTG2, pVKPTG3 and pVKPTG4, respectively. The nucleotide sequences of the inserted fragments were determined according to the forementioned method and it was confirmed that the expected fusion genes were expected.

Additionally, the fusion genes of about 1.8 kb to 1.9 kb of transglutaminase having the pro-structure parts, which was ligated to the respective regions encoding the 30, 31, 44 and 68 amino acid residues and the 5'-upstream region comprising the promoter region of the gene of the protein corresponding to PS2 of *C. glutamicum*, was excised by digesting pVKPTG1, pVKPTG2, pVKPTG3 and pVKPTG4 with KpnI and XbaI and were recovered by agarose electrophoresis. These fragments were inserted into KpnI-XbaI site of pPK4 described in JP-Kokai No. 9-322774 to construct pPKPTG1, pPKPTG2, pPKPTG3 and pPKPTG4.

(2) Secretion of Pro-transglutaminase with the Signal Sequence of the Cell Surface Protein of *C. glutamicum* ATCC13869

*C. glutamicum* ATCC13869 was transformed with the constructed plasmid pVKPTG1, pVKPTG2, pVKPTG3, pVKPTG4, pPKPTG1, pPKPTG2, pPKPTG3 or pPKPTG4 and the strains grown on the CM2S agar medium, described above, comprising 5 mg/l of chloramphenicol or 25 mg/l of kanamycin were selected. The selected *C. glutamicum* ATCC13869 harboring pVKPTG1, pVKPTG2, pVKPTG3, pVKPTG4, pPKPTG1, pPKPTG2, pPKPTG3 or pPKPTG4 was then cultured in MM culture medium, described above, comprising 5 mg/l of chloramphenicol or 25 mg/l of kanamycin at 30° C. for 48 hours, respectively. After the incubation was finished, 10 µl of the supernatant of the culture was subjected to SDS-PAGE and then Western blot was performed using anti-transglutaminase antibody as described in Biosci. Biotechnol. Biochem., 58, 82-87 (1994) according to the conventional method. As a result, the secretion of the similar amount of transglutaminase having the pro-structure part was confirmed for both of the vectors, pVC7 or pPK4, and the significant difference in the secreted amount was observed depending on the length of N-terminal amino acid residues of the mature form of the protein corresponding to PS2. The representative secreted amounts are shown in Table 1.

TABLE 1

The secreted amount of pro-transglutaminase using the signal sequence of the cell surface protein of *C. glutamicum* ATCC13869

| plasmid | pro-transglutaminase (mg/l) |
| --- | --- |
| pPKPTG1 | 78 |
| pPKPTG4 | 210 |

(3) Cleavage of the Pro-transglutaminases by Dispase Digestion and the Detection of Their Activities To the supernatant of the culture of *C. glutamicum* ATCC13869 harboring pVKPTG1, pVKPTG2, pVKPTG3, pVKPTG4, pPKPTG1, pPKPTG2, pPKPTG3 or pPKPTG4, the protease, Dispase (Boeringer Manheim Co. Ltd.) was added at a ratio of substrate:enzyme=1:1 and the reaction was maintained at 37° C., pH 7.5 for 1 hour. After the Dispase digestion, the cleavage of the pro-transglutaminases was confirmed by SDS-PAGE, and the similar specific activities (about 20 U/mg) to that of the naturally occurring transglutaminase was confirmed, as determined by hydroxamate method [J. Biol. Chem., 241, 5518-5525 (1966)].

Example 4

Secretory Production of Pro-transglutaminase Using the Fusion Gene Having the sequence encoding the signal sequence of the cell surface protein of *C. ammoniagenes* and the Pro-transglutaminase Derived from *S. mobaraense* IFO13819

(1) Construction of the Transglutaminase Gene Having the Additional Pro-Structure Part and the Signal Sequence of the Cell Surface Protein of *C. ammoniagenes* (Heterologously Fused Preprotransglutaminase Fusion Gene)

Primers shown in SEQ ID NO: 23 and SEQ ID NO: 24 were synthesized on referring to the sequence of the gene of the cell surface protein (SlpA) [JP-Kokai No. 10-108675] of *C. ammoniagenes* and the region comprising the 5'-upstream region containing the promoter region of the cell surface protein (SlpA) gene and the region encoding its N-terminal 25 amino acid residues (the signal peptide) were amplified using PCR method from the chromosomal DNA of *C. ammoniagenes* prepared according to the conventional method. The primer shown in SEQ ID NO: 24 also comprises the sequence encoding the N-terminal amino acids of the pro-transglutaminase in order to construct the fusion gene fused with the pro-transglutaminase.

(SEQ ID NO: 23)
5'-GCCCAGAAGCCCAAAATTGAGATTT-3'

(SEQ ID NO: 24)
5'-CTTCGTCTCTTCCCCCGCGCCATTGTCTGCCGTTGCCACAGGTGCGG
CCAGC3'

<Sequence Listing Free Text>
SEQ ID NO: 23 and SEQ ID NO: 24: PCR-primers

The fusion transglutaminasetransglutaminase gene containing the additional pro-structure part which was ligated to the region encoding the N-terminal 25 amino acid residues of *C. ammoniagenes* and the 5'-upstream region comprising the promoter region of the cell surface protein (SlpA) gene (heterologously fused prepro-transglutaminase gene) was amplified by performing cross-over PCR with SEQ ID NO: 23 and SEQ ID NO: 9 using the mixture as the templates containing 1 μl of PCR solution of the amplified 5'-upstream region containing the promoter region of the gene of the cell surface protein (SlpA) and the amplified region encoding the N-terminal 25 amino acid residues of the cell surface protein (SlpA) of C. ammoniagenes, and 1 μl of PCR solution of the region of the gene for the transglutaminase having the additional pro-structure part which had been amplified in Example 3(1). The amplified fragment of about 1.7 kb was detected by agarose electrophoresis. This fragment was recovered from agarose gel using EASYTRAP Ver. 2 (Takarashuzo Co. Ltd.) and was inserted into SmaI site of pVC7 to obtain pVSPTG1.

(2) Conversion of the Promoter Region: Ligation with the Promoter of the Cell Surface Protein Gene of *C. glutamicum* ATCC13869

Primers shown in SEQ ID NO: 14 and SEQ ID NO: 25 were synthesized on referring to the sequence of the gene of PS2 which is the cell surface protein [Mol. Microbiol., 9, 97-109 (1993)] of *C. glutamicum*. The 5'-upstream region comprising the promoter region of the gene for the protein corresponding to PS2 was amplified using PCR method from the chromosomal DNA of *C. glutamicum* ATCC13869 prepared according to the method in Example 1(2). The primer shown in SEQ ID NO: 25 also comprises the sequence encoding the N-terminal amino acids of the signal sequence of the cell surface protein (SlpA) of *C. ammoniagenes* in order to construct the fusion gene fused of the transglutaminase gene having the pro-structure part fused with the signal sequence of the superficial zone protein (SlpA) of *C. ammoniagenes* (heterologously fused prepro-transglutaminase fusion gene).

(SEQ ID NO: 25)
5'-CGCAGCCAGCGATTTCATGCGTTTCATAGAGGCGAAGGCTCCTTGAA
TAGGT-3'

<Sequence Listing Free Text>
SEQ ID NO: 25: PCR Primer

On the other hand, primers shown in SEQ ID NO: 26 and SEQ ID NO: 9 were synthesized based on the sequence of the transglutaminase fusion gene having the additional pro-structure part, which contained the signal sequence of the cell surface protein (SlpA) of *C. ammoniagenes*, and the region of the transglutaminase having the additional pro-structure part, which contained the signal sequence of cell surface protein (SlpA) of *C. ammoniagenes*, was amplified using PCR method from pVSPTG1 obtained in Example 4(1).

(SEQ ID NO: 26)
5'-ATGAAACGCATGAAATCGCTGGCTGCGGCG-3'

<Sequence Listing Free Text>
SEQ ID NO: 26; PCR Primer

The fusion gene of transglutaminase having the pro-structure part, which was ligated to the region encoding the N-terminal 25 amino acid residues of the cell surface protein (SlpA) of *C. ammoniagenes* and to the 5'-upstream region containing the promoter region of the gene of the protein corresponding to PS2 of *C. glutamicum* ATCC13869, was then amplified by performing cross-over PCR with SEQ ID NO: 14 and SEQ ID NO: 9 using the mixture comprising 1 μl of PCR solution of the amplified 5'-upstream region containing the promoter region of the gene for the protein corresponding to PS2 of *C. glutamicum* and 1 μl of PCR solution of the amplified region of the gene for the transglutaminase having the pro-structure part which had the signal sequence of the cell surface protein (SlpA) of *C. ammoniagenes* (heterologously fused prepro-transglutaminase gene).

The amplified fragment of about 1.8 kb was detected by agarose electrophoresis.

This fragment was recovered from the agarose gel using EASYTRAP Ver. 2 (Takarashuzo Co. Ltd.) and inserted into SmaI site of pVC7 described in JP-Kokai No. 9-070291 to obtain pVKSPTG1. The nucleotide sequence of the inserted fragment was determined according to the aforementioned method and it was confirmed that the expected fusion gene was constructed.

The fusion gene of about 1.8 kb of fusion gene for transglutaminase having the pro-structure, which was ligated to the region encoding the N-terminal 25 amino acid residues (signal peptide) of the cell surface protein (SlpA) of *C. ammoniagenes* and comprised the 5'-upstream region containing the promoter region of the gene of the protein corresponding to PS2 of *C. glutamicum* ATCC13869, was excised by digesting pVKSPTG1 with KpnI and XbaI and was recovered using agarose electrophoresis. This fragment was inserted into KpnI-XbaI site of pPK4 described in JP-Kokai No. 9-322774 to construct pPKSTG1. Both plasmids, pVKSPTG1 and pPKSPTG1 comprised the promoter from PS2 gene of *C. glutamicum* ATCC13869, the signal peptide gene from SlpA of *C. ammoniagenes* and the transglutaminase gene from *S. mobaraense*.

(3) Conversion into *E. coli* Tac Promoter

Primers shown in SEQ ID NO: 27 and SEQ ID NO: 28 were synthesized based on the sequence of plasmid pKK223-3 (AmershamPharmacia Co. Ltd.) wherein *E. coli* tac promoter was cloned. The region corresponding to tac promoter was amplified using PCR method from pKK223-3 DNA. The primer shown in SEQ ID NO: 28 also comprises the sequence encoding the N-terminal amino acid sequence of the signal sequence of the cell surface protein (SlpA) of *C. ammoniagenes* in order to construct the fusion gene having the pro-structure part, which contained the signal sequence of the cell surface protein (SlpA) of *C. ammoniagenes* (heterologously fused prepro-transglutaminase gene).

```
                                              (SEQ ID NO: 27)
5'-GGATCCGGAGCTTATCGACTGCACG-3'

(SEQ ID NO: 28)
5'-CGCAGCCAGCGATTTCATGCGTTTCATAATTCTGTTTCCTGTGTGAA
ATTGT-3'
```

<Sequence Listing Free Text>
SEQ ID NO: 27 and SEQ ID NO: 28: PCR Primers

The fusion gene for transglutaminase having the additional pro-structure part, which was ligated to the region encoding the N-terminal 25 amino acid residues of the superfical zone protein (SlpA) of *C. ammoniagenes* and which contained tac-promoter (heterologously fused prepro-transglutaminase gene), was amplified by performing cross-over PCR with SEQ ID NO: 27 and SEQ ID NO: 9 using the mixture of 1 µl of PCR solution of the amplified region corresponding to tac-promoter and 1 µl of PCR solution of the amplified region of the gene for transglutaminase having the pro-structure part, which contained the signal sequence of the cell surface protein (SlpA) of *C. ammoniagenes*, as the templates. The amplified fragment of about 1.5 kb was detected by agarose electrophoresis. This fragment was recovered from the agarose gel by EASYTRAP Ver. 2 (Takarashuzo Co. Ltd.) and inserted into SmaI site of the pVC7 as described in JP-Kokai No. 9-070291 to obtain pVTSPTG1. The nucleotide sequence of the inserted fragment was determined according to the aforementioned method and it was confirmed that the expected fusion gene was constructed.

The fusion gene about 1.5 kb for transglutaminase having the pro-structure part, which was ligated to the region encoding the N-terminal 25 amino acid residues of the cell surface protein (SlpA) of *C. ammoniagenes* and tac promoter, was excised by digesting pVTSPTG1 with KpnI and XbaI and was recovered using agarose electrophoresis. This fragment was inserted into KpnI-XbaI site of pPK4 described in JP-Kokai No. 9-322774 to construct pPTSPTG1. Both plasmids pVTSPTG1 and pPTSPTG1 comprised tac-promoter derived from *E. coli*, the signal peptide gene derived from SlpA of *C. ammoniagenes* and the pro-transglutaminase gene derived from *S. mobaraense*.

(4) Secretion of the Pro-transglutaminase Using the Signal Sequence of Cell Surface Protein of *C. ammoniagenes*

*C. glutamicum* ATCC13869 was transformed with the constructed plasmid pVKSPTG1, pVTSPTG1, pPKSPTG1, or pPTSPTG1 and the strains grown on the CM2S agar medium, described above, comprising 5 mg/l of chloramphenicol or 25 mg/l of kanamycin were selected. The selected *C. glutamicum* ATCC13869 harboring pVKSPTG1, pVTSPTG1, pPKSPTG1, or pPTSPTG1 was then cultured in the MM culture medium, described above, comprising 5 mg/l of chloramphenicol or 25 mg/l of kanamycin at 30° C. for 48 hours, respectively. After the incubation was finished, 10 µl of the supernatant of the culture was subjected to SDS-PAGE and then Western blot was performed with anti-transglutaminase antibody as described in Biosci. Biotechnol. Biochem., 58, 82-87 (1994) according to the conventional method. As a result, the similar amount of transglutaminase was confirmed to be secreted for either of the vectors, pVC7 or pPK4. The representative amounts of the secretion are shown in Table 2.

TABLE 2

The secreted amount of pro-transglutaminase using the signal sequence of cell surface protein of *C. ammoniagenes* ATCC13869

| plasmid | protransglutaminase (mg/l) |
|---------|---------------------------|
| pPKSPTG1 | 102 |
| pPTSPTG1 | 74 |

(5) Cleavage of Protransglutaminase by Dispase Digestion and the Detection of the Activity To the supernatant of the culture of *C. glutamicum* ATCC13869 harboring pVKSPTG1, pVTSPTG1, pPKSPTG1, or pPTSPTG1, a protease Dispase (Boeringer Manheim Co. Ltd.) was added at a ratio of substrate:enzyme=1:1 and the reaction was maintained at 37° C. pH 7.5 for 1 hour. After Dispase digestion, the reaction mixture was subjected to SDS-PAGE to confirm the cleavage of pro-transglutaminase having the pro-structure part, and the similar specific activity (about 20 U/mg) to that of the naturally occurring transglutaminase was confirmed to be contained, after determining the transglutaminase activity by hydroxamate method.

Example 5

Cleavage of Protransglutaminase Using the Culture Medium or the Cells of *S. mobaraense* and the Detection of the Activity (1) Cleavage of Protransglutaminase Using the Culture Medium and the Detection of the Activity

*S. mobaraense* IFO13819 strain was cultures in ISP2 culture medium (4 g of yeast extract, 10 g of malt extract, 4 g of glucose per liter of distilled water, adjusted to pH7.3) at 30° C. for 24 hours. To 10 ml of the culture medium, the supernatant of the culture of *C. glutamicum* ATCC13869 harboring pVKSPTG1, pVTSPTG1, pPKSPTG1, or pPTSPTG1, which was also used in Example 4(5) and where pro-transglutaminase was accumulated, was added after filtration by a membrane filter and the culture medium was maintained at 30° C. for 6 hours. It was then subjected to SDS-PAGE to confirm the cleavage of transglutaminase having the pro-structure part. The activity of the transglutaminase was confirmed, which had the similar specific activity (about 20 U/mg) to that of the naturally occurring transglutaminase as determined by hydroxamate method. Further it was semi-dry blotted onto polyvinylidene-difluoride (PVDF) membrane after SDS-PAGE (Structural analysis of proteins for gene cloning, Tokyo Kagaku Dojin (1993)). After blotting, the PVDF membrane was stained with Coomassie Brilliant Blue, de-stained and air-dried. The portion containing the mature transglutaminase was excised and analyzed for the N-terminal amino acid sequence using Protein Sequencer (Model 476A, Parkin Elmer Co. Ltd.). As a result, it was confirmed that the protein had the same amino acid sequence to that of the naturally occurring mature transglutaminase shown in SEQ ID NO: 5.

(2) Cleavage of Transglutaminase with the Pro-Structure Part Using the Cells of S. mobaraense IFO13819 Strain S. mobaraense IFO13818 strain was cultured in ISP2 culture medium at 30° C. for 24 hours. The cells were harvested by centrifugation of 10 ml of the culture medium and were washed twice with saline. The cells finally harvested were suspended in 10 ml of saline. To the suspensions, 10 ml of the supernatant of the culture of C. glutamicum ATCC13869 harboring pVKSPTG1, pVTSPTG1, pPKSPTG1, or pPTSPTG1 which was also used in Example 4(5) and where the pro-transglutaminase was accumulated, was added after filtration, and the mixture was maintained at 30° C. for 6 hours. Then it was subjected to SDS-PAGE and the cleavage of transglutaminase having the pro-structure part was confirmed, and the transglutaminase activity showing the similar specific activity (about 20 U/mg) to that of the naturally occurring transglutaminase was confirmed to be contained as determined by hydroxamate method. Further it was semi-dry blotted onto polyvinylidene-difluoride (PVDF) membrane after SDS-PAGE process (Structural analysis of proteins for gene cloning, Tokyo Kagaku Dojin (1993)). After the blotting, the PVDF membrane was stained with Coomassie Brilliant Blue, de-stained and air-dried. The portion containing mature transglutaminase was excised and were analyzed for the N-terminal amino acid sequence using a protein sequencer.

As a result, it was confirmed that the protein had the same amino acid sequence to that of the naturally occurring mature transglutaminase shown in SEQ ID NO: 5.

Example 6

Secretory Production of Pro-transglutaminase using the Fusion Gene Containing the Sequence Encoding the Signal Sequence of the Cell Surface Protein of C. ammoniagenes and the Protransglutaminase Derived from Streptoverticillium cinnamoneum IFO12852

(1) Construction of the Fusion Gene Comprising the Sequence Encoding the Signal Sequence of the Cell Surface Protein of C. ammoniagenes and the Sequence Encoding the Pro-Transglutaminase Derived from S. cinnamoneum IFO12852

The sequence of the transglutaminase gene of S. cinnamoneum IFO12852 has been determined [Japanese Patent Application No. 11-295649]. The region from position 1 to position 32 in the amino acid sequence is presumed to be the sequence for the pre-part, from position 33 to position 86 is presumed to be the sequence for the pro-part and from position 87 to position 416 is presumed to be the sequence for the mature transglutaminase sequence. Putative sequences of the pro-structure part and the mature protein are shown in SEQ ID NO: 4 and SEQ ID NO: 43, respectively. Additionally Escherichia coli AJ13669 which had been transformed with the plasmid pUJ-MTG containing the gene has been deposited in the National Institute of Bioscience and Human-Technology Agency of Industrial Science and Technology on Oct. 14, 1999 as FERM P-17602 and has been transferred to the deposit under the Budapest Treaty on Aug. 28, 2000, and the deposit number of FERM BP-7287 has been allotted.

The region of 3.5 kb covering the full-length of the prepro-transglutaminase gene was firstly excised from pUJ-MTG with restriction enzyme BamHI, and pUCSCTG was generated wherein the region was inserted into BamHI site of pUC19.

Primers shown in SEQ ID NO: 44 and SEQ ID NO: 45 were synthesized, and the region of the gene comprising the pro-transglutaminase derived from S. cinnamoneum IFO12852 was amplified by PCR method using pUCSCTG as the template as previously described.

(SEQ ID NO: 44)
5'-GGC GAT GGG GAA GAG AAG GGG-3'

(SEQ ID NO: 45)
5'-GGC GGA TCC TVG CGT CGA GAG GCG TGG ACT GA-3'

<Sequence Listing Free Text>
SEQ ID NO: 44 and SEQ ID NO: 45: PCR Primers

The region, which comprises the 5'-upstream region containing the promoter region of PS2 gene which is the cell surface protein of C. glutamicum and the region containing the signal sequence of the cell surface protein SlpA of C. ammoniagenes, was then amplified by performing PCR using the combination of SEQ ID NO: 46 and SEQ ID NO: 47 from pPKSPTG1 as the template which was constructed in Example 4(2).

The primer shown in SEQ ID NO: 47 also comprises the sequence encoding the N-terminal amino acid sequence of pro-transglutaminase derived from Streptoverticillium cinnamoneum IFO12852 in order to construct the fusion gene with the transglutaminase derived from Streptoverticillium cinnamoneum IFO12852.

(SEQ ID NO: 46)
5'-TAC GAA TTC GAG CTC GGT ACC-3'

(SEQ ID NO: 47)
5'-CCC CTT CTC TTC CCC ATC GCC TGC CGT TGC CAC AGG TGC GGC C-3'

<Sequence Listing Free Text>
SEQ ID NO: 46 and SEQ ID NO:47: PCR Primers

The fragment of the heterologously fused prepro-transglutaminase gene, which was ligated to the signal sequence of the cell surface protein SlpA of C. ammoniagenes and the 5'-upstream region comprising the promoter region of PS2 gene, was amplified by performing cross-over PCR with SEQ ID NO: 46 and SEQ ID NO: 45 using the mixture comprising 1 μl of PCR solution of the amplified region encoding the gene for the pro-transglutaminase derived from C. cinnamoneum IFO12852 and 1 μl of PCR solution of the amplified 5'-upstream region containing the promoter region of the PS2 gene and the amplified region comprising the signal sequence of the cell surface protein SlpA of C. ammoniagenes, as the templates.

The amplified fragment of about 1.8 kb was detected by agarose electrophoresis.

This fragment was digested with EcoRI and BamHI, and then recovered from the agarose gel and inserted into EcoRI-BamHI site of the pUC19 to obtain pUKSPTG2'. The sequence of the inserted fragment was determined according to the aforementioned method and it was confirmed that the fusion gene was constructed as expected. This pUKSPTG2' was digested with EcoRI and blunt-ended with Blunting Kit (Takarashuzo Co. Ltd.), and XbaI linker (Takarashuzo Co. Ltd.) having the sequence 5'-CTCTAGAG-3' wherein 5'-terminal was phosphorylated was then inserted and re-cyclized to construct pUKSPTG2. The fused preprotransglutaminase gene of about 1.8 kb (the protransglutaminase gene was derived from *S. cinnamoneum* IFO12852) was excised by digesting pUKSPTG2 with XbaI and was recovered using agarose electrophoresis. These fragments were inserted into XbaI site of pPK4 described previously to construct pPK-SPTG2.

The preprotransglutaminase having a chimeric pro-structure part, wherein the N-terminal of the pro-structure part was partially replaced by the pro-structure part of *S. mobaraense*, was constructed (the mature transglutaminase gene and the part of the pro-structure part were derived from *S. cinnamoneum* IFO12852).

Firstly, the fragment of about 1.8 kb containing the preprotransglutaminase gene of EcoRI-BamHI was excised from the plasmid pPKSPTG1 (for the expression of the pro-transglutaminase derived from *S. mobaraense* IFO13819) which was constructed in Example 4(2), and the fragment was inserted into EcoRI-BamHI site of pUC19 (pUKSPTG1). The fragment of about 1.2 kb was excised by digesting pUKSPTG1 with AatII, and pUKSPTG2' was also digested with AatII to prepare the fragment of about 3.3 kb removing the fragment of about 1.2 kb. This fragment of about 3.3 kb was ligated to the AatII fragment of about 1.2 kb derived from pUKSPTG1, and clones wherein the AatII fragment was inserted were selected according to the conventional genetic engineering techniques. In order to determine which orientation the AatII fragment was inserted into the clones, they were serially sequenced and the clones wherein the fragment was inserted in the desired orientation were selected (pUKSPTG3'). Moreover the EcoRI site of pUKSOTG3' was also blunt-ended as with pUKSPTG2' and XbaI linker was inserted to construct pUKSPTG3. Further the 1.8 kb XbaI fragment excised from pUKSPTG3 was inserted into XbaI site of pPK4 to construct pPKSPTG3.

(2) Secretion of the Pro-transglutaminase Derived from *Streptoverticillium cinnamoneum* IFO12852 Using the Signal Sequence of the Cell Surface Protein from *C. ammoniagenes*

*C. glutamicum* ATCC13869 was transformed using the plasmid pPKSPTG2 or pPKSPTG3, and the strains which grew on the CM2S agar medium described above comprising 25 mg/l of kanamycin were selected. The selected *C. glutamicum* ATCC13869 harboring pPKSPTG2 or pPKSPTG3 was then cultured respectively in MMTG liquid culture medium (60 g of glucose, 0.4 g of magnesium sulfate heptahydrate, 30 g of ammonium sulfate, 1 g of potassium dihydrogenphosphate, 0.01 g of ferrous sulfate heptahydrate, 0.01 g of manganese(II) sulfate pentahydrate, 450 µg of thiamine hydrochloride, 450 µg of biotin, 0.15 g of DL-methionine, 50 g of calcium carbonate per liter of distilled water, adjusted to pH 7.5) containing 25 mg/l of kanamycin at 30° C. for 3 days. After the incubation was finished, 10 µl of the supernatant of the culture was subjected to SDS-PAGE and then Western blot analysis was performed according to the conventional method with anti-transglutaminase antibody as described previously. The antibody is an antibody for the transglutaminase derived from *S. mobaraense*, but it also showed the reactivity to the transglutaminase derived from *S. cinnamoneum*. Consequently the secretion of the transglutaminase having the pro-structure part derived from *S. cinnamonieum* IFO12852 was confirmed (about 30 to 50 mg/l).

Example 7

Secretory Production of Transglutaminase by Replacing the Pro-Structure Part of the Pro-transglutaminase Derived from *S. mobaraense* IFO13819 by the Pro-Structure Part Derived from *S. cinnamoneum* IFO12852 (Generation of the Hybrid)

Primers shown in SEQ ID NO: 14 and SEQ ID NO: 48 were synthesized and the 5'-upstream region comprising the promoter region of PS2 gene of *C. glutamicum* ATCC13869 and the region coding the signal sequence of the cell surface protein of *C. ammoniagenes* and also the pro-structure part of the transglutaminase derived from *S. cinnamoneum* IFO12852 were amplified from pPKSPTG2 or pPKSPTG3 using PCR method, respectively.

The primer shown in SEQ ID NO: 48 also comprises the sequence encoding the N-terminal amino acid sequence of the mature transglutaminase derived from *S. mobaraense* IFO13819 in order to construct the fusion gene which contained the 5'-upstream region containing the promoter region of the PS2 gene of *C. glutamicum* ATCC13869, the signal sequence of the cell surface protein (SlpA) of *C. ammoniagenes* and the gene for the mature transglutaminase derived from *S. mobaraense* IFO13819 having the pro-structure part of the transglutaminase derived from *Streptoverticillium cinnamoneum* IFO 12852

(SEQ ID NO: 14)
5'-AAATTCCTGTGAATTAGCTGATTTAG3'

(SEQ ID NO: 48)
5'-GGG GTG ACC CTG TCG TCG GAG TCG GGG GCC CGG GAG GGC GCG CTG G-3'

<Sequence Listing Free Text>
SEQ ID NO: 48: PCR Primer

On the other hand, primers shown in SEQ ID NO: 8 and SEQ ID NO: 9 were synthesized based on the sequence of the transglutaminase gene derived from *S. mobaraense* determined in Example 1(1) and the gene region of the mature transglutaminase derived from *S. mobaraense* was amplified using PCR method from pUITG which had been obtained in Example 1(1).

5'-GACTCCGACGACAGGGTCACCCCTCCCGCC-3' (SEQ ID NO: 8)

5'-CGCTCACATCACGGCCAGCCCTGCTTTACC-3' (SEQ ID NO: 9)

<Sequence Listing Free Text>
SEQ ID NO:8 and 9: PCR Primers

Then the fragment for the fusion gene of the mature transglutaminase gene derived from *S. mobaraense* IFO13819, which had the 5'-upstream region containing the promoter region of PS2 gene of *C. glutamicum* ATCC13869, the signal sequence of the cell surface protein of *C. ammoniagenes* and the pro-structure part of the protransglutaminase derived from *Streptoverticillium cinnamoneum* IF12852, was amplified using cross-over PCR with SEQ ID NO: 14 and SEQ ID NO: 9 using 1 µl of PCR solution of each amplified region comprising the 5'-upstream region containing the promoter region of the PS2 gene of *C. glutamicum* ATCC13869, the region encoding the signal sequence of the cell surface protein (SlpA) of *C. ammoniagenes* and the sequence encoding the pro-structure part of the transglutaminase derived from *S. cinnamoneum* IFO12852, and also 1 µl of PCR solution of the amplified gene region encoding the mature transglutaminase derived from *S. mobaraense* IFO13819, as the template. The amplified fragment of about 1.8 kb was detected by agarose electrophoresis. The fragment of about 800 bp, which was generated by digesting this fragment with ScaI and Eco065I, was recovered from agarose gel. The fragment excised from pKSPTG1, which had been constructed in Example 4(2), by the digestion with ScaI and Eco065I was replaced by this fragment to construct pPKSPTG4 and pPKSPTG5.

(SEQ ID NO: 14)
5'-AAATTCCTGTGAATTAGCTGATTTAG-3'

(SEQ ID NO: 9)
5'-CGCTCACATCACGGCCAGCCCTGCTTTACC-3'

(2) Secretion of the Transglutaminase Derived from *S. mobaraense* IFO13819 Using The Signal Sequence of the Cell Surface Protein of *C. ammoniagenes* and the Pro-Structure Part Derived from *S. cinnamoneum* IFO12852

*C. glutamicum* ATCC13869 was transformed with the constructed plasmids pPKSPTG4 or pPKSPTG5, and the strains which grew on the CM2S agar medium described above comprising 25 mg/l kanamycin were selected. Then the selected *C. glutamicum* ATCC13869 harboring pPKSPTG4 or pPKSPTG5 was cultured in MMTG culture medium, described above, comprising 25 mg/l kanamycin at 30° C. for 30 days, respectively. After the incubation was finished, 10 µl of the supernatant of the culture was subjected to SDS-PAGE and then Western blot analysis was performed with anti-transglutaminase antibody as described previously according to the conventional method. Consequently the secretion of the transglutaminase derived from *S. mobaraense* IFO13819 having the *S. cinnamoneum* IFO12582 derived pro-structure part was confirmed. Table 3 shows the amount of the production of pro-transglutaminase. pPKSPTG1 was used as a control and was genetically characterized in that the pro-part was derived from *S. mobaraense*. pPKSPTG4 was characterized in the genetic construction in that the pro-part was derived from *S. cinnamoneum*. pPKSPTG5 was characterized in the genetic construction in that the pro-structure had a chimeric pro-structure wherein the N-terminal 16 amino acids of the pro-structure part were derived from *S. mobaraense* and the C-terminal 40 amino acids was derived from *S. cinnamoneum*. Otherwise, the three had the common features. As a result, the significant difference in the amount of secretion was observed due to the difference of the amino acid sequence of the pro-structure part. The strain having the chimeric structure secreted the greatest amount of transglutaminase (ATCC13869/pPKSPTG5).

TABLE 3

Amount of the secretory production of protransglutaminase by the difference of the pro-structure part

| plasmid | protransglutaminase mg/l |
|---|---|
| pPKSPTG1 | 235 mg/l |
| pPKSPTG4 | 130 |
| pPKSPTG5 | 270 |

Example 8

Cloning of the Serine Protease (SAMP45) Gene, and the Generation and Evaluation of Expression Plasmids (1) Construction of the Serine Protease (SAMP45) Gene Having the Pro-Structure Part and the Signal Sequence of the Cell Surface Protein of *C. ammoniagenes* (Heterologously Fused Prepro-serine Protease (SAMP45) Gene)

The sequence of the gene of SAMP45 which is a serine protease produced by *S. albogriseolus* [J. Bacteriol., 179, 430-438 (1997)] has been already determined. Primers shown in SEQ ID NO: 49 and SEQ ID NO: 50 were synthesized on referring to this sequence and the gene region comprising the N-terminal pro-structure part of SAMP45, mature SAMP45 and the C-terminal pro-structure part was amplified using PCR method according to the method described previously.

(SEQ ID NO: 49)
5'-AACGGGGAGAACAGCACGGCCGCCGG-3'

(SEQ ID NO: 50)
5'-GGCGAATTCTCCGGCGGGCCGTCACCGGT-3'

<Sequence Listing Free Text>
SEQ ID NO: 49 and SEQ ID NO: 50: PCR Primers

The region comprising 5'-upstream region containing the promoter region of the gene of the cell surface protein PS2 from *C. glutamicum* and the signal sequence of the cell surface protein SlpA from *C. ammoniagenes* was similarly amplified using PCR method with the combination of SEQ ID NO: 51 and SEQ ID NO: 52 with pPKSPTG1 constructed in Example 4(2) as the template.

The primer shown in SEQ ID NO: 52 comprises the sequence encoding the N-terminal amino acids of pro-serine protease in order to construct the fusion gene containing the serine protease having the pro-structure part.

(SEQ ID NO: 51)
5'-GGCAAGCTTAAATTCCTGTGAATTAGCTGA-3'

(SEQ ID NO: 52)
5'-CGGCCGTGCTGTTCTCCCCGTTTGCCGTTGCCACAGGTGCGGCC-3'

<Sequence Listing Free Text>
SEQ ID NO: 51 and SEQ ID NO: 52: PCR Primers to Construct the Fused Pro-serine Protease Gene Then the gene fragment of the heterologously fused prepro-serine protease gene, which was ligated to the signal sequence of the cell surface protein SlpA of *C. ammoniagenes* and to the 5'-upstream region containing the promoter region of PS2 gene, was amplified by performing cross-over PCR with SEQ ID NO: 51 and SEQ ID NO: 50 using the mixture as the templates comprising 1 µl of PCR solution of the amplified region comprising the gene for the N-terminal pro-structure of SAMP45, mature SAMP45 and the C-terminal pro-structure, and 1 µl of PCR solution of the amplified region comprising the 5'-upstream region containing the promoter region of the PS2 gene and the signal sequence of the cell surface protein SlpA of *C. ammoniagenes*, respectively.

The amplified fragment of about 3.9 kb was detected by agarose electrophoresis.

The PCR product was digested with HindIII and EcoRI, then subjected to agarose gel electrophoresis, and the fragment of about 3.9 kb was recovered from agarose gel and inserted into HindIII-EcoRI site of the aforementioned pVC7 to obtain pVSS1, respectively. The sequence of the inserted fragment was determined according to the forementioned method and it was confirmed that the fusion gene was constructed as expected.

(2) Secretion of the Serine Protease Using the Signal Sequence of the Cell Surface Protein of C. ammoniagenes C. glutamicum ATCC13869 was transformed using the plasmid pVSS1 and the strains which grew on the CM2S agar medium described above comprising 5 mg/l chloramphenicol were selected. The selected C. glutamicum ATCC13869 harboring pVSS1 was then cultured in MMTG culture medium comprising 5 mg/l chloramphenicol at 30° C. for 70 hours. 1 ml of the culture medium was separate into the supernatant of the culture medium and the cells by centrifugation. The cell was suspended in 0.1 M sodium phosphate buffer (pH 7.0). The activity of the serine protease was determined as follows: 50 µl of the supernatant of the culture medium or the cell suspension was added to 20 mM sodium phosphate buffer (pH 7.0) containing 0.25 mM Bz-Phe-Val-Arg-pNA (Bachem Co. Ltd.) to give a total amount of 0.6 ml, which was maintained at 30° C. for 20 minutes. Thereafter the reaction was terminated upon the addition of 0.4 ml of 50% acetic acid. The absorbance was measured at 410 nm and the amount of p-NA (p-nitroanillide) released was measured to determine the activity. One unit of the enzyme was defined as the amount of enzyme which releases 1 µmol of pNA per one minute. As a result, the activity of serine protease was not detected in the supernatant of the culture medium, but was detected in the cell suspension. Calculating from the values of detected activity and the values of the specific activity reported in the literature [J. Bacteriol., 179, 430-438 (1997)], as much as about 9 mg/l of serine protease was confirmed to be expressed and secreted at the surface of the cell.

(3) Cleavage of the Pro-Structure Part of the Transglutaminase Having the Pro-Structure Part by Serine Protease which is Secreto-produced in C. glutamicum ATCC 13869

C. glutamicum ATCC13869 harboring the secretory expression plasmid pPKSPTG1 for the transglutaminase having the pro-structure part described in Example 4(2) was transformed with the constructed plasmid pVSS1 and the strains grown on the CM2S agar medium, described above, comprising 5 mg/l of chloramphenicol and 25 mg/l kanamycin were selected. Next the selected C. glutamicum ATCC13869 harboring pVSS1 and pPKSPTG1 was cultured in the MMTG culture medium, described above, comprising 5 mg/l chloramphenicol and 25 mg/l kanamycin at 30° C. for 70 hours. After the incubation was finished, 10 µl of the supernatant of the culture was subjected to SDS-PAGE and then Western blot analysis was performed with anti-transglutaminase antibody previously described according to the conventional method. As a result, it was confirmed that SAMP45 was normally expressed and secreted, and that the pro-structure part was cleaved from the transglutaminase having the pro-structure part which is also secreted, resulting in the secretion of the transglutaminase having the similar molecular weight to that of the naturally occurring mature transglutaminase.

The supernatant of the culture medium was investigated for transglutaminase activity by hydroxamate method previously described, which confirmed that it had the similar specific activity (about 20 U/mg) as that of the naturally occurring transglutaminase.

Further it was semi-dry blotted on polyvinylidene-difluoride (PVDF) membrane according to the method previously described after SDS-PAGE. After blotting, the PVDF membrane was stained with Coomassie Brilliant Blue, de-stained and air-dried. The portion containing the mature transglutaminase was excised and was analyzed for the N-terminal amino acid sequence using a protein sequencer. As a result, it was confirmed that it had the structure in which the 4 C-terminal amino acids of Phe-Arg-Ala-Pro from the pro-structure part was added to the naturally occurring mature transglutaminase derived from S. mobaraense shown in SEQ ID NO: 5.

Example 9

Cloning of the Proline Specific Peptidase (svPEP) Gene, and the Generation and Evaluation of Expression Plasmids (1) Purification of the Proline Specific Peptidase (SvPEP) Produced by S. mobaraense IFO13819

800 mL of ISP2 liquid culture medium (4 g of yeast extract, 10 g of malt extract, 4 g of glucose filled up to 1 L by water, adjusted to pH 7.3) was placed in a 5 L Sakaguchi flask and S. mobaraense IFO13819 was inoculated from the plate into the flask and cultured by shaking at 30° C. for 48 hours at 120 rpm.

The culture medium was centrifuged to remove the supernatant of the culture and the cells were harvested. After washing the cells with 20 mM Tris-HCl buffer containing 25 mg/l kanamycin, the resulting cells was suspended in 0.1 M sodium phosphate buffer (pH 7.0) containing 25 mg/l kanamycin. The suspension was shaken on ice for 4 hours and centrifuged to give the supernatant, which was collected. After the supernatant was filter-sterilized using nitrocellulose filter (0.22 µm poresized, Sartrius Co. Ltd.), the supernatant was passed through the Butyl-Sepharose 4FF (Amersham Pharmacia Co. Ltd.) column (1.6φ×10 cm), which had been pre-equilibrated with 1.5 M ammonium sulfate/50 mM phosphate buffer (pH 7.0), using FPLC (Amersham Pharmacia Co. Ltd.) and eluted by the linear gradient of ammonium sulfate 1.5 to 0 M in the same buffer. Fractions containing active components were pooled and passed through Phenyl-Sepharose HP column (1 mL, Amersham Pharmacia Co. Ltd.) under the same condition, and active fractions were pooled and dialyzed overnight against 50 mM sodium phosphate buffer (pH 7.0) at 4° C. to give partially purified enzyme solution.

The total weight, total activity, specific activity, yield of proteins at each step are presented in Table 4. The enzyme activity at each step was determined according to the method by Yoshimoto et al (Tsuru and Funatsu eds., Seibutsukagaku Jikkenhou, 31 Proteolytic enzyme II, Gakkai Shuppan Center (1993), p187) as follows:

The enzyme solution was added to 20 mM of sodium phosphate buffer containing 0.25 mM of Ala-Ala-Pro-pNA (Bachem Co. Ltd.) to give a total amount of 0.6 ml, which was maintained at 30° C. for 5 minutes. Thereafter the reaction was terminated upon the addition of 0.4 ml of 50% acetic acid. The absorbance was measured at 410 nm and the amount of p-NA released was calculated to determine the activity. One unit of the enzyme was defined as the amount of the enzyme which releases 1 µmol of pNA per one minute.

TABLE 4

Purification of proline specific peptidase derived from S. mobaraense

| Purification steps | volume (ml) | total activity (units) | total protein (mg) | specific activity (unit/mg) | yield (%) | purification level (fold) |
|---|---|---|---|---|---|---|
| crude extract | 550 | 308 | 385 | 0.80 | 100 | 1 |
| Butyl-Sepharose 4FF | 45.6 | 213 | 8.98 | 23.7 | 69 | 30 |
| Phenyl-Sepharose HP | 5.8 | 136 | 3.83 | 35.5 | 44 | 44 |

(2) Sequencing of the N-terminal Amino Sequence of the Proline Specific Peptidase (svPEP) Produced by *S. mobaraense* IFO13819

Partially purified enzyme solution was subjected to reversed phase chromatography for further purification. The condition of reversed phase chromatography was as follows:
HPLC device: pump: HITACHI L-6300, detector: L-4000H
column: PROTEIN C4 214TP5410(VYDAC Co. Ltd.)
elution: Elution was effected by a lineal gradient of acetonitrile 24-40%/0.1% trifluoroacetic acid (20 min) at room temperature
flow rate: 1.0 ml/min.
detection wavelength: 280 nm The enzyme samples which were purified under the condition describe above were transferred onto Polyvinylidene-difluoride (PVDF) membrane using Membrane Cartridge (Perkin Elmer Co. Ltd.) and the N-terminal amino acid sequence was analyzed using gas-phase Protein Sequencer PPSQ-10 (Shimazu Seisakusho Co., Ltd.). As a result, the N-terminal 20 amino acid residues were determined, which are shown in SEQ ID NO: 53.

```
                                    (SEQ ID NO: 53)
    Gln Ala Asp Ile Lys Asp Arg Ile leu Lys Ile Pro
     1               5                  10

Gly Met Lys Phe Val Glu Glu Lys
                15                  20
```

(3) Evaluation of the Properties of the Proline Specific Peptidase (svPEP) Produced by *S. mobaraense* IFO13819

Proline specific peptidase (svPEP) produced by *S. mobaraense* IFO13819 was evaluated for the following properties:
(i) Substrate Specificity (a) When a chromophore pNA-conjugated peptide were used as a substrate: Purified enzyme solution was added to 20 mM of sodium phosphate buffer (pH 6.5) containing 0.25 mmol of each of various peptides conjugated to pNA to give a total amount of 0.6 ml, which was maintained at 37° C. for 5 minutes. The reaction was terminated upon the addition of 0.4 ml of 50% acetic acid. The absorbance was measured at 410 nm to determine the cleaving activity.

(b) When a chromophoric group βNA(β-naphtylamido)-conjugated peptide was used as a substrate: Purified enzyme solution was added to 20 mM of sodium phosphate buffer (pH 6.5) containing 0.3 mmol of each of various peptides to give a total amount of 1.0 ml, which was maintained at 37° C. for 5 minutes. The reaction was terminated upon the addition of 0.4 ml of Fast garnet GBC solution (Fast garnet GBA was dissolved in 10% Triton X-100/1M sodium acetate (pH 4.0) to give 0.1%). The absorbance was measured at 550 nm to determine the cleaving activity.

(c) When a peptide were used as a substrate: Enzyme solution was added to the peptide solution, which was prepared to be 1 mg/ml, as a substrate and the reaction was performed at 30° C. for 1 hour. The cleaving activity was confirmed using HPLC under the following condition:
Column: YMC-PACK ODS-A 4.6×150 mm (YMC)
Eluent: 0.1% trifluoroasetic acid (TFA)-acetonitrile
Flow rate: 1 ml/min
Detection wavelength: UV 220 nm As a result, it was revealed that the enzyme was the enzyme which cleaves a peptide specifically at the carboxyl terminal side of proline residue, and that it preferably recognized Ala-Ala-Pro-pNA, Phe-Arg-Ala-Xaa (SEQ ID NO: 68) (wherein Xaa represents Pro-pNA and pNA represents p-nitroanilide), Ala-Phe-Pro-pNA in this order, and that it was most specifically reactive to the peptide which had proline at the 3rd or 4th position from the N-terminal. It was also revealed that the enzyme did not act on the peptide which had proline at the 2nd or 5th position from the N-terminal (Table 5).

TABLE 5

Specifity of svPEP

| Peptide substrate | relative activity (%) |
|---|---|
| p-pNA | 0.04 |
| DP-pNA | 0.00 |
| Z-GP-βNA | 0.04 |
| GP-βNA | 0.40 |
| AP-pNA | 0.53 |
| RP-pNA | 0.94 |
| Z-AGP-βNA | 0.78 |
| Z-GAP-βNA | 1.2 |
| Bz-FVR-pNA | 0.002 |
| AAF-pNA | 4.1 |
| AAA-pNA | 8.5 |
| AFP-pNA | 26.3 |
| AAP-pNA | 100 |
| AAPL-pNA | 0.3 |
| FRAP-pNA | 49.0 |
| Suc-AAPF-pNA | 0.01 |
| SFRAP-pNA | 1.23 |
| PSFRAP-pNA | 0.2 | pNA: p-nitroanilide,
βNA: β-naphtylamido

<Sequence Listing Free Text>
SEQ ID NO: 68: Substrate for svPEP
(ii) Optimum pH
  pH 4 to 6: 20 mM sodium phosphate buffer,
  pH 5.5 to 8: 20 mM sodium phosphate buffer, and
  pH 6.5 to 9.5: 20 mM tris-hydrochloride buffer
were used as a buffer, respectively. The enzyme was allowed to act on Ala-Ala-Pro-pNA as the substrate at 30° C. for 5 minutes. Relative activity of the enzyme in each buffer was calculated compared to the activity in 20 mM sodium phosphate buffer, pH6.5 as 100%. As a result, it was revealed that its optimum pH ranged from 6 to 6.5.
(iii) pH Stability
0.15 M GTA buffers (buffers composed of 3,3-dimethylglutaric acid, tris(hydroxymethyl)aminomethane, 2-amino-2-methyl-1,3-propanediol) ranging between pH 3 and pH10 were used. To 20 μl of purified enzyme solution, 40 μl of the buffer at each pH was added and the reaction mixtures were allowed to stand overnight at 4° C., then adjusted to pH 7.0 and the volume was made up to 120 μl. To 50 μl aliquots, Ala-Ala-Pro-pNA was added and the reaction was performed at 30° C. for 5 minutes. Relative amounts of substrate which the enzyme decomposed at each pH were considered to be the remaining activity compared to the activity of the enzyme as 100% when the enzyme was stored under the same condition as described above except for pH 7.0. As a result, it was revealed that the enzyme was stable at pH 4 to 9.

(iv) Optimum Temperature

To 50 µl of purified enzyme solution, 0.5 ml of 20 mM sodium phosphate buffer (pH 6.5) was added and Ala-Ala-Pro-pNA was added up to 0.25 mM and the mixture was maintained at 20° C.-60° C. for 5 minutes to effect decomposition reaction. Relative amount of substrate which the enzyme decomposed was considered to be the relative activity at each temperature, compared to the amount of substrate decomposition at 25° C. as 100% activity. As a result, it was revealed that its optimum temperature ranged from 25 to 30° C.

(v) Temperature Stability

To 50 µl of purified enzyme solution, 0.5 ml of 20 mM sodium phosphate buffer (pH 6.5) was added. The mixture was maintained at 4° C. or 20° C.-60° C. for 15 minutes and then cooled on ice. Ala-Ala-Pro-pNA was added up to 0.25 mM and the mixture was maintained at 30° C. for 5 minutes. The remaining activity was calculated assuming the activity of the enzyme which was treated at 4° C. to be 100%. As a result, it was revealed that the enzyme was stable below 20° C.

(vi) Inhibitors

To 20 mM sodium phosphate buffer (pH 6.5) containing each compound at the indicated concentration shown in Table 6, purified enzyme solution was added and the mixture was allowed to stand at room temperature for 10 minutes. Then Ala-Ala-Pro-pNA was added and the reaction was performed at 30° C. for 5 minutes. Assuming the activity of the enzyme to Ala-Ala-Pro-pNA in the absence of compounds to be 100%, relative amount of substrate decomposition in the presence of the compound was considered to be the relative activity. As a result, the enzyme was inhibited to some extent by chloromercuribenzoic acid, etc. which is the SH-enzyme inhibitors, but it was undergone the comparatively strong inhibition by phenyl methylsulfonylfluoride (Nakaraitesk Co., Ltd.) and aminoethylbenzenesulfonylfluoride hydrochloride (Boeringer Manheim Co., Ltd.) which were the serine protease inhibitors.

TABLE 6

Effects of inhibitors to the activity of proline specific peptidase derived from S. mobaraense

| Compounds | Concentration (mM) | relative activity (%) |
|---|---|---|
| None | 0 | 100 |
| Serine enzyme inhibitors | | |
| Phenylmethylsulfonylfluoride | 1 | 39.7 |
| Aminoethylbenzenesulfonylfluoride hydrochloride | 4 | 59.9 |
| Chymostatin | 1 | 84.9 |
| SH-enzyme inhibitors | | |
| p-Chloromercuribenzoic acid | 1 | 87.1 |
| N-Ethylmaleimide | 1 | 98.3 |
| Iodoacetamide | 1 | 87 |
| Asparagine enzyme inhibitor | | |
| Pepstatin | 1 | 165.7 |
| Metalloprotease inhibitors | | |
| EDTA | 10 | 105.2 |
| 1,10-Phenanthroline | 1 | 92.5 |

TABLE 6-continued

Effects of inhibitors to the activity of proline specific peptidase derived from S. mobaraense

| Compounds | Concentration (mM) | relative activity (%) |
|---|---|---|
| Aminopeptidese inhibitor | | |
| Bestatin | 1 | 97.6 |
| Reducing agent | | |
| Dithiothreitol | 10 | 102.5 |
| Prolylendopetidase inhibitors | | |
| Z-(S)Pro-(S)Prolinal | 1 | 111.2 |
| Z-Pro-(S)Prolinal | 1 | 105.8 |
| Z-Pro-Prolinal | 1 | 99.7 |

(3) Acquisition of the Proline Specific Peptidase (svPEP) Gene Derived from S. mobaraense IFO13819

The region having less degeneracy which is deduced from the determined N-terminal amino acid sequence of svPEP, Lys-Ile-Pro-Gly-Met-Lys-Phe-Val-Glu-Glu-Lys, was selected and the synthetic oligonucleotide shown in SEQ ID NO: 54 was generated. The chromosomal DNA prepared according to the conventional method was digested with various restriction enzymes which recognize 6-nucleotides sequence and then analyzed by Southern blot hybridization method using this synthetic oligonucleotide as the probe and thereby a single band of about 6 kb was detected by SacI cleavage. Accordingly, the chromosomal DNA of S. mobaraense IFO13819 prepared according to the forementioned method was digested with Sac I and the fragment of about 6 kb was recovered using agarose gel electrophoresis with EASYTRAP Ver. 2 (Takarashuzo Co. Ltd.). The recovered fragment was inserted in Sac I site of pUC18, which was introduced into the competent cell of Escherichia coli JM109 (Takarashuzo Co. Ltd.), thereby producing a library. The generated library in this way was screened for the strain which harbored the plasmid wherein the fragment of svPEP gene was cloned, by screening the library through colony hybridization using $^{32}$P-labelled synthetic oligonucleotide shown in SEQ ID NO: 54 as a probe to obtain the intended gene. The plasmid recovered from this strain was designated as pUMP1.

(SEQ ID NO: 54)
5'-AAGATCCCCGGGATGAAGTTCGTCGAGGAGAAG-3'

<Sequence Listing Free Text>
SEQ ID NO: 54: a Probe for svPEP

The nucleotide sequence of the fragment which was cloned as pUMP1 was determined. The nucleotide sequence of svPEP gene corresponding to svPEP is shown in SEQ ID NO: 41. The amino acid sequence encoded by this gene was deduced and the previously determined N-terminal amino acid sequence (20 residues) based on the enzyme protein was found, and the primary amino acid sequence of mature svPEP shown in SEQ ID NO:40 was determined. The entire primary amino acid sequence containing the putative signal sequence and the pro-structure part of svPEP was determined, which is shown in SEQ ID NO: 42.

Escherichia coli AJ13669 which was transformed with pUMP1 has been deposited in the National Institute of Bioscience and Human-Technology Agency of Industrial Science and Technology on May 15, 2000 as FERM BP-7160 under the Budapest Treaty.

(4) Construction of the Proline Specific Peptidase (svPEP) Gene Having the Pro-Structure Part with the Signal Sequence of the Cell Surface Protein of *C. ammoniagenes* (Heterologously Fused Prepro-proline Specific Peptidase (svPEP) Gene)

Primers shown in SEQ ID NO: 55 and SEQ ID NO: 56 were synthesized on referring to the sequence of svPEP determined in Example 9(3), and the gene region containing the pro-part of svPEP and mature svPEP were amplified by PCR method in the same manner as described previously using pUMP1 constructed in Example 9(3) as the template.

```
                                          (SEQ ID NO: 55)
5'-GAGGCGGCGTCGATCACCGCCCC-3'

(SEQ ID NO: 56)
5'-GCCAAGCTTGAAGCACCGGGCGGCGGCACCCGG-3'
```

<Sequence Listing Free Text>
SEQ ID NO: 55 and SEQ ID NO: 56: PCR Primers

Then the region, which comprises the 5'-upstream region containing the promoter region of PS2 gene which is the gene of the cell surface protein of *C. glutamicum* and the region containing the signal sequence of the cell surface protein SlpA of *C. ammoniagenes*, was amplified by PCR method from pPKSPTG1 constructed in Example 4(2) as the template using the combination of SEQ ID NO: 51 and SEQ ID NO: 57.

The primer shown in SEQ ID NO: 57 comprises the sequence encoding the N-terminal amino acids of svPEP in order to construct the fusion gene fused to the svPEP having the pro-structure part.

```
                                          (SEQ ID NO: 51)
5'-GGCAAGCTTAAATTCCTGTGAATTAGGCTGA-3'

(SEQ ID NO: 57)
5'-GGGGCGGTGATCGACGCCGCCTCTGCCGTTGCCACAGGTGCGGCCA-
3'
```

<Sequence Listing Free Text>
SEQ ID NO: 57: PCR Primer

The fragment of the heterologously fused gene of prepro-svPEP, which was ligated to the signal sequence of the cell surface protein SlpA of *C. ammoniagenes* and the 5'-upstream region containing the promoter region of PS2 gene, was then amplified by performing cross-over PCR with SEQ ID NO: 51 and SEQ ID NO: 56 using the mixture as the templates comprising 1 µl of each PCR solution of the region containing the gene encoding the pro-structure part of svPEP and the mature svPEP, which were amplified respectively, and 1 µl of PCR solution of the amplified region comprising 5'-upstream region containing the promoter region of the PS2 gene and the signal sequence of the cell surface protein SlpA of *C. ammoniagenes*.

```
                                          (SEQ ID NO: 51)
5'-GGCAAGCTTAAATTCCTGTGAATTAGCTTA-3'

(SEQ ID NO: 56)
5'-GCCAAGCTTGAAGCACCGGCGGCGGCACCCGG-3'
```

The amplified fragment of about 2.1 kb was detected by agarose electrophoresis.

The PCR fragment was digested with HindIII, and then subjected to agarose gel electrophoresis and the fragment of about 2.1 kb recovered from the agarose gel and inserted into the HindIII site of the pVSS1 described in Example 8(1) to obtain pVSSSP1, respectively. The sequence of the inserted fragment was determined according to the conventional method and it was confirmed that the expected fusion gene was constructed.

(5) Secretion of the Proline Specific Peptidase Using the Signal Sequence of the Cell Surface Protein of *C. ammoniagenes*

*C. glutamicum* ATCC13869 was transformed with the constructed plasmid pVSSSP1 and the strains which grew on the CM2S agar medium described above comprising 5 mg/l chloramphenicol were selected. The selected *C. glutamicum* ATCC13869 harboring pVSSSP1 was then cultured in MMTG culture medium, described above, comprising 5 mg/l chloramphenicol at 30° C. for 70 hours. 10 µl of the supernatant of the culture was separated by centrifugation into the supernatant of the culture medium and the cells. The cells were suspended in 0.1 M sodium phosphate buffer (pH7.0). The activity of svPEP was determined as follows: 50 µl of the supernatant of the culture medium or the cell suspension was added to 20 mM sodium phosphate buffer (pH 7.0) containing 0.25 mM Ala-Ala-Pro-pNA (Bachem Co. Ltd.) to give a total amount of 0.6 ml and the mixture was maintained at 30° C. for 20 minutes. Thereafter the reaction was terminated upon the addition of 0.4 ml of 50% acetic acid. The absorbance was measured at 410 nm and the amount of p-NA (p-nitroanillide) released was calculated to determine the activity. One unit of the enzyme is defined as the amount of enzyme which releases 1 µmol of pNA per 1 minute. As a result the activity of svPEP was not detected in the supernatant of the culture medium, but was detected in the cell suspension. Calculating from the values of the detected activity and the values of the specific activity described in Example 9(1), as much as about 50 mg/l of svPEP was confirmed to be expressed and secreted at the surface of the cell.

(6) Cleavage of the Pro-Structure Part by the Serine Protease and Proline Specific Protease Expressed and Secreted by *C. glutamicum* ATCC13869

*C. glutamicum* ATCC13869 harboring the secretory expression plasmid pPKSPTG1 for transglutaminase having the pro-structure part described in Example 4(2) was transformed with the constructed plasmid pVSSSP1, and the strains grown on the CM2S agar medium, described above, comprising 5 mg/l of chloramphenicol and 25 mg/l kanamycin were selected. Then the selected *C. glutamicum* ATCC13869 harboring pVSSSP1 and pPKSPTG1 was cultured in MMTG culture medium, described above, comprising 5 mg/l chloramphenicol and 25 mg/l kanamycin at 30° C. for 70 hours. After the incubation was finished, 10 µl of the supernatant of the culture was subjected to SDS-PAGE and then Western blot analysis was performed with anti-transglutaminase antibody previously described according to the conventional method. As a result, it was confirmed that SAMP45 and svPEP were normally expressed and secreted, and that the pro-structure part was cleaved from the transglutaminase having the pro-structure part which had been also secreted, thereby the secretion of the transglutaminase having the similar molecular weight to that of the naturally occurring mature transglutaminase was confirmed.

The transglutaminase activity was tested for the supernatant by the hydroxamate method previously described, which confirmed that it contained the similar specific activity (about 20 U/mg) to that of the naturally occurring transglutaminase.

Further it was semi-dry blotted onto polyvinylidene difluoride (PVDF) membrane according to the method previously described after SDS-PAGE. After blotting, the PVDF membrane was stained with Coomassie Brilliant Blue, de-stained and air-dried. The portion containing the mature transglutaminase was removed and analyzed for the N-terminal amino acid sequence using a protein sequencer. As a result, it was confirmed that it had the same sequence as the naturally occurring transglutaminase derived from *S. mobaraense* having Asp as the N-terminal amino acid, which is shown in SEQ ID NO: 5.

Example 10

Generation of the Partial Deletion Variant of the Pro-Structure of *S. mobaraense* ISO13819 Derived Pro-transglutaminase and the Secretory Production of Transglutaminase (1) Construction of the Gene for Partial Deletion Variants of the Pro-Structure of the Transglutaminase In order to generate the partial deletion form wherein the C-terminal amino acid residues of the pro-structure part were deleted, primers shown in SEQ ID NO: 8 and SEQ ID NO: 9 were synthesized based on the sequence of the transglutaminase gene determined in Example 1(1) and the gene region of the mature transglutaminase was amplified using pUITG obtained in Example 1(1) by the similar PCR method as described previously.

Then the gene region comprising the 5'-upstream region containing the promoter of the PS2 gene which was the cell surface protein of *C. glutamicum*, the region of the gene for the signal sequence of cell surface protein SlpA of *C. glutamicum* and the pro-structure part of transglutaminase was amplified with the combination of SEQ ID NO: 14 and SEQ ID NO: 58 or of SEQ ID NO: 14 and SEQ ID NO: 59 using pPKSPTG1 constructed in Example 4(2) as the template.

The primer shown in SEQ ID NO: 58 has the sequence which is defective of two C-terminal amino acids residues, Ala-Pro, of the pro-structure part of transglutaminase, and the primer shown in SEQ ID NO: 59 has the sequence which is defective of the C-terminal 4 amino acid residues, Phe-Arg-Ala-Pro, of the pro-structure part of the transglutaminase and further comprises the sequence encoding the N-terminal amino acid residues of the mature transglutaminase in order to construct the fusion gene with mature transglutaminase.

(SEQ ID NO: 14)
5'-AAATTCCTGTGAATTAGCTGATTTAG-3'

(SEQ ID NO: 58)
5'-GTG ACC CTG TCG TCG GAG TCC CGG AAC GAC GGG CCG GCG C-3'

(SEQ ID NO: 59)
5'-GTG ACC CTG TCG TCG GAG TCC GAC GGG CCG GCG CTC GAA G-3'

<Sequence Listing Free Text>
SEQ ID NO: 58 and SEQ ID NO: 59: PCR Primers

The gene fragment for the mature transglutaminase, which was ligated to the deletion form of the pro-structure of the transglutaminase, the signal sequence of the cell surface proteinSlpA of *C. ammoniagenes* and the 5'-upstream region containing the promoter region of the gene of PS2 which is the cell surface protein of *C. glutamicum*, was amplified respectively using cross-over PCR with SEQ ID NO: 14 and SEQ ID NO: 9 using as the template 1 µl of each PCR solution comprising the amplified 5'-upstream region containing the promoter region of PS2 gene which is the cell surface protein of *C. glutamicum*, the signal sequence of the cell surface proteinSlpA of *C. ammoniagenes* and each of the modified pro-structure part, and 1 µl of PCR solution of the amplified region encoding the mature transglutaminase.

(SEQ ID NO: 14)
5'-AAATTCCTGTGAATTAGCTGATTTAG-3'

(SEQ ID NO: 9)
5'-CGCTCACATCACGGCCAGCCCTGCTTTACC-3'

The amplified fragment of about 1.8 kb was detected by agarose electrophoresis.

The fragment of about 800 by which was generated by digesting this fragment with restriction enzymes ScaI and Eco065I was recovered from agarose gel and was replaced for the fragment cleaved from pPKSPTG1, which was constructed in Example 4(2), with ScaI and Eco065I to construct pPKSPTG1 ΔAP (Ala-Pro deletion type) and pPKSPTG1 ΔFRAP (Phe-Arg-Ala-Pro deletion type).

Then in order to generate the partial deletion form of the pro-part wherein the N-terminal amino acid residues of the pro-structure part were partially deleted, primers shown in SEQ ID NO: 60 and SEQ ID NO: 61 were synthesized based on the sequence of the gene of the transglutaminase determined in Example 1(1) and the regions of the mature transglutaminase gene were amplified using pUITG obtained in Example 1(1) by the same PCR with the combination of SEQ ID NO:60 and SEQ ID NO:9 or of SEQ ID NO: 61 and SEQ ID NO:9.

(SEQ ID NO: 60)
5'-AAT GGC GCG GGG GAA GAG ACG AAG TCC TAC GCC GAA ACC T-3'

(SEQ ID NO: 61)
5'-GAG ACG AAG TCC TAC GCC GAA ACC TAC CGC CTC ACG GCG G-3'

(SEQ ID NO: 9)
5'-CGCTCACATCACGGCCAGCCCTGCTTTACC-3'

<Sequence Listing Free Text>
SEQ ID NO: 60 and SEQ ID NO: 61: PCR Primers

Then the regions comprising the 5'-upstream region containing the promoter of the gene of PS2 which was the cell surface protein of *C. glutamicum* and the region for the signal sequence of cell surface protein SlpA of *C. glutamicum* were amplified with the combination of SEQ ID NO: 14 and SEQ ID NO: 62 or of SEQ ID NO: 14 and SEQ ID NO: 63 using pPKSPTG1 constructed in Example 4(2) as the template.

The primer shown in SEQ ID NO: 62 has the sequence defective of the N-terminal first amino acid residue, Asp, of the pro-part of the transglutaminase, the primer shown in SEQ ID NO: 63 has the sequence defective of the N-terminal 6 amino acid residues, Asp-Asn-Gly-Ala-Gly-Glu, and further they comprise the sequence encoding the C-terminal amino acid residues of the signal sequence of the cell surface proteinSlpA of *C. ammoniagenes* in order to construct the fusion gene fused with the signal sequence of the cell surface protein SlpA of *C. ammoniagenes*.

(SEQ ID NO: 14)
5'-AAATTCCTGTGAATTAGCTGATTTAG-3'

(SEQ ID NO: 62)
5'-GTC TCT TCC CCC GCG CCA TTT GCC GTT GCC ACA GGT GCG G-3'

-continued (SEQ ID NO: 63)
5'-TCG GCG TAG GAC TTC GTC TCT GCC GTT GCC ACA GGT GCG G-3'

<Sequence Listing Free Text>
SEQ ID NO: 62 and SEQ ID NO: 63: PCR Primers

The fragment of the mature transglutaminase gene, which is ligated to the partial deletion type for the pro-structural part of the transglutaminase, to the signal sequence of the cell surface proteinSlpA of *C. ammoniagenes* and also to the 5'-upstream region containing the promoter region of the gene of PS2 which is the cell surface protein of *C. glutamicum*, was amplified respectively using cross-over PCR with SEQ ID NO: 14 and SEQ ID NO: 9 using 1 μl of PCR solution for the 5'-upstream region containing the promoter region of the gene of PS2 which is the cell surface protein of *C. glutamicum* and the region encoding the region comprising the signal sequence of the cell surface protein-SlpA of *C. ammoniagenes* and 1 μl of PCR solution of the amplified region encoding the pro-transglutaminase wherein the N-terminal of the pro-structure part was partially deleted, as the template respectively.

(SEQ ID NO: 14)
5'-AAATTCCTGTGAATTAGCTGATTTAG-3'

(SEQ ID NO: 9)
5'-CGCTCACATCACGGCCAGCCCTGCTTTACC-3'

The amplified fragments of about 1.8 kb were detected by agarose electrophoresis. The fragments of about 800 by which were generated by digesting these fragments with restriction enzymes ScaI and Eco065I were recovered from agarose gel and were replaced for the fragment excised from pPKSPTG1 with ScaI and Eco065I, which was constructed in Example 4(2), to construct pPKSPTG1 ΔD (Asp deletion type) and pPKSPTG1 ΔDNGAGE (Asp-Asn-Gly-Ala-Gly-Glu deletion type).

(2) Secretion of the Transglutaminase Having the Partial Deletion Form of the Pro-Structure

*C. glutamicum* ATCC13869 was transformed with the constructed plasmid pPKSPTG1 ΔAP, pPKSPTG1 ΔFRAP, pPKSPTG1 ΔD or pPKSPTG1 ΔDNGAGE and the strains grown on the CM2S agar medium, described above, comprising 25 mg/l kanamycin were selected. The selected *C. glutamicum* ATCC13869 harboring pPKSPTG1 ΔAP, pPKSPTG1 ΔFRAP, pPKSPTG1 ΔD or pPKSPTG1 ΔDNGAGE was then cultured in MMTG culture medium, described above, comprising 25 mg/l kanamycin at 30° C. for 48 hours, respectively. After the incubation was finished, 10 μl of the supernatant of the culture was subjected to SDS-PAGE and then Western blot analysis was performed with anti-transglutaminase antibody previously described according to the conventional method. As a result, the secretion of the transglutaminase wherein the pro-structure part was partially deleted was confirmed. The transformant harboring pPKSPTG1 ΔAP, pPKSPTG1 ΔFRAP or pPKSPTG1 ΔD showed the secretion equivalent to that of the naturally occurring form (pPKSPTG1), respectively, but the transformant harboring pPKSPTG1 Δ DNGAGE showed about a half secretion relative to that of the naturally occurring form (pPKSPTG1).

(3) Cleavage of the Pro-Structure Part of the Protransglutaminase Having the Partial Deletion Form of the Pro-Structure by Serine Protease Secreto-produced by *C. glutamicum* ATCC13869

*C. glutamicum* ATCC13869 harboring the secretory expression plasmid pPKSPTG1 ΔAP, pPKSPTG1 ΔFRAP, pPKSPTG1 ΔD or pPKSPTG1 ΔDNGAGE for the protransglutaminase having the partial deletion form of the pro-structure, which were described in Example 10 (2), was transformed with the plasmid pVSS1 constructed in Example 8(1) and the strains grown on the CM2S agar medium, described above, comprising 5 mg/l of chloramphenicol and 25 mg/l kanamycin were selected. The selected *C. glutamicum* ATCC13869 harboring pVSS1 and pPKSPTG1 ΔAP, pPKSPTG1 ΔFRAP, pPKSPTG1 ΔD or pPKSPTG1 ΔDNGAGE was then cultured in the MMTG liquid culture medium, described above, comprising 5 mg/l chloramphenicol and 25 mg/l kanamycin at 30° C. for 70 hours. After the incubation was finished, 10 μl of the supernatant of the culture was subjected to SDS-PAGE and then western-blotted with anti-transglutaminase antibody previously described according to the conventional method.

As a result, SAMP45 was confirmed to be normally expressed and secreted, and that the pro-structure part of the similarly secreted pro-transglutaminase having the partial deletion form of the pro-structure was cleaved, resulting in the secretion of the transglutaminase having the similar molecular weight to that of the naturally occurring mature transglutaminase.

Further semi-dry blotted onto PVDF membrane was performed after SDS-PAGE, according to the same method as previously described. After the blotting, the PVDF membrane was stained with Coomassie Brilliant Blue, de-stained and air-dried. The portions containing the mature transglutaminase were removed and were analyzed for the N-terminal amino acid sequence using a protein sequencer.

As a result, it was confirmed that Phe-Arg was added to the N-terminal of the naturally occurring mature transglutaminase shown in SEQ ID NO: 5 in the transformant harboring pPKSPTG1 ΔAP, Ser-Ala-Gly-Pro-Ser was added to the N-terminal of the naturally occurring mature transglutaminase in the transformant harboring pPKSPTG1 ΔFRAP, and that Phe-Arg-Ala-Pro was added to the naturally occurring mature transglutaminase in the transformant harboring pPKSPTG1 ΔD or pPKSPTG1 ΔDNGAGE.

Example 11

Generation of the Variants for Pro-Structure Part of Transglutaminase Derived from *S. mobaraense* IFO13819 and Secretory Production of Transglutaminase (1) Construction of the Pro-Transglutaminase Genes Having the Variants for Pro-Structure Part Primers shown in SEQ ID NO: 8 and SEQ ID NO: 9 were synthesized based on the sequence of the gene of the transglutaminase determined in Example 1(1) and the region of the gene of mature transglutaminase was amplified from pUITG obtained in Example 1(1) using the PCR method.

Then the region, which comprises the 5'-upstream region containing the promoter of the gene of PS2 which was the cell surface protein of *C. glutamicum*, the region of the gene of the signal sequence of cell surface protein SlpA of *C. glutamicum* and the pro-structure part of transglutaminase, was amplified using PCR method with the combination of SEQ ID NO: 14 and SEQ ID NO: 64, or of SEQ ID NO: 14 and SEQ ID NO: 65, or of SEQ ID NO: 14 and SEQ ID NO: 66, or of SEQ ID NO: 14 and SEQ ID NO: 67 using pPKSPTG1 constructed in Example 4(2) as the template.

The primer shown in SEQ ID NO: 64 comprises the gene sequence wherein the C-terminal 3 amino acid residues of the pro-structure part of transglutaminase, Arg-Ala-Pro were converted into Gly-Pro-Lys, the primer shown in SEQ ID NO: 65 comprises the gene sequence wherein the C-terminal 3 amino acid residues of the pro-structure part of transglutaminase, Arg-Ala-Pro, were converted into Gly-Pro-Arg, the primer shown in SEQ ID NO: 66 comprises the gene sequence wherein the C-terminal 5 amino acid residues of the pro-structure part of transglutaminase, Ser-Phe-Arg-Ala-Pro were converted into only Lys, and the primer shown in SEQ ID NO: 67 comprises the gene sequence wherein Ser-Phe-Arg-Ala-Pro were converted to only Arg.

Further they comprises the sequence encoding the N-terminal amino acid residues of mature transglutaminase in order to construct the fusion gene fused with mature transglutaminase (SEQ ID NO: 14)
5'-AAATTCCTGTGAATTAGCTGATTTAG-3'

(SEQ ID NO: 64)
5'-GTG ACC CTG TCG TCG GAG TCC TGG CCG AAC GAC GGG C-3'

(SEQ ID NO: 65)
5'-GTG ACC CTG TCG TCG GAG TCG CGG GGG CCG AAC GAC GGG C G-3'

(SEQ ID NO: 66)
5'-GTG ACC CTG TCG TCG GAG TCC TCC GGG CCG GCG CTC GAA G-3'

(SEQ ID NO: 67)
5'-GTG ACC CTG TCG TCG GAG TCG CGC GGG CCG GCG CTC GAA G-3'

<Sequence Listing Free Text>
SEQ ID NO: 64, SEQ ID NO: 65, SEQ ID NO: 66 and SEQ ID NO: 67: PCR Primers The transglutaminase gene fragments, which were ligated to the modified pro-structure part of the transglutaminase having the modified pro-structure, the signal sequence of the cell surface protein SlpASlpA of *C. ammoniagenes* and the 5'-upstream region containing the promoter region of the gene of PS2 which is the cell surface protein of *C. glutamicum*, was amplified by cross-over PCR with SEQ ID NO: 14 and SEQ ID NO: 9 using 1 µl of PCR solution of the respectively amplified region comprising the genes encoding the 5'-upstream region comprising the promoter region of the gene of PS2 which is the cell surface protein of *C. glutamicum*, the signal sequence of the cell surface protein SlpASlpA of *C. ammoniagenes*, and the region encoding the region containing the modified pro-structure part, and 1 µl of PCR solution of the amplified region encoding the mature transglutaminase.

(SEQ ID NO: 14)
5'-AAATTCCTGTGAATTAGCTGATTTAG-3'

(SEQ ID NO: 9)
5'-CGCTCACATCACGGCCAGCCCTGCTTTACC-3'

The amplified fragments of about 1.8 kb were detected by agarose electrophoresis. The fragments of about 800 bp, which were generated by digesting these fragment with restriction enzymes ScaI and Eco065I, were recovered from agarose gel and were replaced for the fragment cleaved from pPKSPTG1 constructed in Example 4(2) with ScaI and Eco065I to construct pPKSPTG11 (Gly-Pro-Lys type modified variant) and pPKSPTG12 (Gly-Pro-Arg type modified variant), pPKSPTG13 (Δphe-Arg-Ala-Pro type and Lys insertion-variant) and pPKSPTG14 (Δphe-Arg-Ala-Pro type and Arg insertion-variant).

(2) Secretion of the Transglutaminase in the Modified Pro-Structure Part Form

*C. glutamicum* ATCC13869 was transformed with the constructed plasmids pPKSPTG11, pPKSPTG12, pPKSPTG13 or pPKSPTG14 and the strains grown on the CM2S agar medium, described above, comprising 25 mg/l kanamycin were selected. Then the selected *C. glutamicum* ATCC13869 harboring pPKSPTG11, pPKSPTG12, pPKSPTG13 or pPKSPTG14 was cultured in MMTG culture medium, described above, comprising 25 mg/l kanamycin at 30° C. for 48 hours, respectively.

After the incubation was finished, 10 µl of the supernatant of the culture was subjected to SDS-PAGE and then Western blot analysis was performed with the anti-transglutaminase antibody previously described according to the conventional method. As a result, the secretion of the transglutaminase having the pro-structure part was confirmed.

(3) Cleavage of the Pro-Structure Part of the Transglutaminase Having the Pro-Structure Part Variant with Serine Protease Produced by Secretory Production by *C. glutamicum* ATCC13869

*C. glutamicum* ATCC13869 harboring the secretory expression plasmid pPKSPTG11, pPKSPTG12, pPKSPTG13 or pPKSPTG14 for the transglutaminase having the pro-structure part variant, which was described in Example11 (2), was transformed with the plasmid pVSS1 constructed in Example 8(1) and the strains grown on the CM2S agar medium, described above, comprising 5 mg/l of chloramphenicol and 25 mg/l kanamycin were selected. The selected *C. glutamicum* ATCC13869 harboring pVSS1 and pPKSPTG11, pVSS1 and pPKSPTG12, pVSS1 and pPKSPTG13, or pVSS1 and pPKSPTG14 was then cultured in the MMTG liquid culture medium, described above, comprising 5 mg/l chloramphenicol and 25 mg/l kanamycin at 30° C. for 70 hours. After the incubation was finished, 10 µl of the supernatant of the culture was subjected to SDS-PAGE and then Western blot analysis was performed with anti-transglutaminase antibody previously described according to the conventional method. As a result, SAMP45 was confirmed to be normally expressed and secreted, the pro-structure variant of the transglutaminase having the pro-structure variant, which had been also secreted, was confirmed to be cleaved, and consequently the secretion of transglutaminase having the similar molecular weight to that of the naturally occurring mature transglutaminase was confirmed.

Further semi-dry blotting onto PVDF membrane was performed according to the same method as previously described after SDS-PAGE. After the blotting, the PVDF membrane was stained with Coomassie Brilliant Blue, de-stained and air-dried. The portions containing mature transglutaminase were excised and were analyzed for the N-terminal amino acid sequence using a protein sequencer. As a result, the sequence identical to that of the naturally occurring mature transglutaminase was confirmed for *C. glutamicum* ATCC13869 harboring pVSS1 and pPKSPTG11, or pVSS1 and pPKSPTG12, which had Asp as the N-terminal amino acid residue. In contrast, the sequence wherein Ser-Ala-Gly-Pro-Lys (SEQ ID NO: 69) or Ser-Ala-Gly-Pro-Arg (SEQ ID NO: 70) was found to be added to the sequence of the naturally occurring mature transglutaminase for *C. glutamicum* ATCC13869 harboring pVSS1 and pPKSPTG13, or pVSS1 and pPKSPTG14.

The transglutaminase activity was determined for the supernatant of the culture medium of the former which showed the same amino acid sequence as that of the naturally occurring mature transglutaminase, which confirmed that they had almost the same specific activity (about 20 U/mg) as that of the naturally occurring transglutaminase as determined by hydroxamate method previously described.

<Sequence Listing Free Text>

SEQ ID NO: 69, SEQ ID NO: 70: Sequence Added to the Sequence of the Naturally Occurring Transglutaminase According to the present invention it is possible to make a coryneform bacterium to produce and secrete a large amount of a useful protein, particularly transglutaminase extracellularly. Since the protein produced according to the present invention is released into the culture medium, the protein can be directly recovered from the culture medium more simply and in a larger scale by known appropriate methods.

What is claimed:

1. An isolated nucleic acid molecule encoding proline specific peptidase having the following properties:
   (1) reacts on at least one of the following proline containing peptides and cleaves it at the carboxyl terminal side of the proline residue:
      Ala-Ala-Pro-pNA, Ala-Phe-Pro-pNA, Phe-Arg-Ala-Pro-pNA
   wherein pNA represents p-nitroanilide;
   (2) has an optimum pH of 6.0-6.5;
   (3) is stable at pH4-9;
   (4) has the optimum temperature of 25-30° C.;
   (5) is stable below 20° C.;
   (6) its activity is inhibited by phenylmethylsulfonyl fluoride and aminoethylbenzenesulfonylfluoride hydrochloride;
   (7) has an isoelectric point of 10.2;
   (8) has a molecular weight of approximately 50,000; and
   (9) comprises amino acid sequence of SEQ ID NO: 40.

2. The nucleic acid molecule of claim 1, wherein the amino acid sequence consists of SEQ ID NO: 40.

3. A method of making a host cell comprising the nucleic acid of claim 1, comprising introducing the nucleic acid of claim 1 into a host cell.

4. A method of producing a proline specific peptidase, comprising introducing the nucleic acid of claim 1 into a host cell, expressing the nucleic acid in the host cell and isolating the proline specific peptidase.

* * * * *